United States Patent [19]
Sobol et al.

[11] Patent Number: 5,681,562
[45] Date of Patent: Oct. 28, 1997

[54] LYMPHOKINE GENE THERAPY OF CANCER

[75] Inventors: Robert E. Sobol; Fred H. Gage; Ivor Royston; Theodore Friedman, all of La Jolla; Habib Fakhrai, Oceanside, all of Calif.

[73] Assignee: Sidney Kimmel Cancer Center, San Diego, Calif.

[21] Appl. No.: 352,990

[22] Filed: Dec. 9, 1994

Related U.S. Application Data

[63] Continuation of Ser. No. 863,641, Apr. 3, 1992, abandoned, Continuation-in-part of Ser. No. 781,356, Oct. 25, 1991, abandoned, Continuation-in-part of Ser. No. 720,872, Jun. 25, 1991, abandoned.

[51] Int. Cl.$^6$ .......................... A61K 48/00; A61K 39/00; C12N 5/00
[52] U.S. Cl. ............................... 424/93.21; 435/240.2; 435/320.1; 435/172.3; 435/69.5; 424/184.1; 424/277.1
[58] Field of Search .............................. 435/69.1, 69.5, 435/69.51, 69.52, 69.3, 320.1, 240.2, 172.3, 7.2; 530/350, 351; 514/44, 2, 12; 424/85.1, 85.5, 85.2, 93.21, 93; 935/62, 52, 55, 57, 32, 66, 70, 71, 33, 34, 65

[56] References Cited

FOREIGN PATENT DOCUMENTS

WO92/05262  2/1992  European Pat. Off. ........ C12N 15/85

OTHER PUBLICATIONS

Rosenberg, Steven A. "The Immunotherapy and Gene Therapy of Cancer." *J. Clin. Oncology* 10:180–199 (1992).
Russell, Stephen J. "Lymphokine Gene Therapy for Cancer." *Immunology Today.* 11:196–200 (1990).
Wakabayashi et al. Cytoxic T–lymphocyte induced by syngeneic mouse melanoma cells recognize human melanomas. Nature 294, vol. 294, 748–750, 1981.
Gansbacher, Bernd et al., "Interleukin 2 Gene Transfer into Tumor Cells Abrogates Tumorigenicity and Induces Protective Immunity", J. Exp. Med. 90:1237–1224 (1990).
Gabrilove, Janice l. and Jakubowski, Ann "Hematopoietic Growth Factors: Biology and Clinical Application". J. of the National Cancer Inst. Monographs. 10:73–77 (1990).
Sarna, Gregory et al., "A Pilot Study of Intralymphatic Interleukin-2. II. Clinical and Biological Effects". J. Biol. Response Modifiers. 9:81–86 (1990).
Hoover, H.C. Jr. et al., "Delayed Cutaneous Hypersensitivity to Autologous Tumor Cells in Colorectal Cancer Patients Immunized With the Autologous Tumor Cell": *Bacillus calmette–Guerin Vaccine* Cancer Res. 44:1671–1676 (1984).
Bubenik, J. et al., "Immunotherapy of Cancer using Local Administration of Lymphpoid Cells Transformed by IL–2 cDNA and Constitutively Producing IL–2". Immunology Letters. 23:287–292 (1989/1990).
Borden, Ernest C., and Sondel, Paul m., "Lympokines and Cytokines as Cancer". 65:800–814 (1990).

Rosenberg, Steven A. et al., "New Approaches to the Immunotherapy of Cancer Using Interleukin–2". Annals of Internal Medicine. 108:853–864 (1988).
Li Xu, et al., "Factors Affecting Long–Term Stability of Moloney Murine Leukemia Virus–Based Vectors". Virology 171:331–341 (1989).
Gansbacher, Bernd, et al., "Retroviral Vector–Mediated τInterferon Gene Transfer into Tumor Cells Generates Potent and Antitumor Immunity." Cancer Research 50:7820–7825 (1990).
Fearon, Eric R. et al., "Interleukin–2 Production by Tumor Cells Bypasses T Helper Function in the Generation of an Antitumor Response." Cell 60:397–403 (1990).
Gandolfi, L. et al., "Intratumoral Echo–guided Injection of INterleukin–2 and Lymphokine–Activated Killer Cells in Hepatorcellular Carcinom." Hepato–gastroenterol 36:352–356 (1989).
Watanabe, Yoshihiko et al., "Exogenous Expression of Mouse Interferon τcDNA in Mouse Neuroblastoma C1300 Cells Results in Reduced Tumorigenicity by Augmented Anti–Tumor Immunity." Proc. Natl. Acad. Sci. USA. 86:9456–9460 (1989).
Pizza, G. et al., "Intra–Lymphatic Administration of Interleukin–2 (IL–2) in Cancer Patients: A Pilot Study." Lympokine Research 7:45–48 (1988).
Lotze, Michael T. et al., "High–Dose Recombinant Interleukin 2 in the Treatment of Patients with Disseminated Cancer." JAMA 256:3117–3124 (1986).
Lotze, Michael T. et al., "Mechanisms of Immunologic Antitumor Therapy: Lession from the Laboratory and Clinical Applications." Human Immunology 28:198–207 (1990).
Schreiber, Hans. "Tumor Immunology." *Fundamental Immunology, Second Edition.* 923–942 (1989).
Peace, David J. et al., "T Cell Recognition of Transforming Proteins Encoded by Mutated ras Proto–Oncogenes." J. Immunology. 146:2059–2065 (1991).
Bubenik, J. et al., "Local Administration of Cells Containing an Inserted IL–2 Gene and Producing IL–2 Inhibits Growth of Human Tumors in Nu/Nu Mice." Immunology Letters. 19:279–282 (1988).
Tepper, Robert L et al., "Murine Interleukia–4 Displays Potent Anti–tumor Activity on Vivo." Cell 57:503–512 (1989).

(List continued on next page.)

*Primary Examiner*—Jasemine C. Chambers
*Assistant Examiner*—Karen Marie Hauda
*Attorney, Agent, or Firm*—Campbell and Flores

[57] ABSTRACT

A novel method of tumor immunotherapy is described comprising the genetic modification of cells resulting in the secretion of cytokine gene products to stimulate a patient's immune response to tumor antigens. In one embodiment, autologous fibroblasts genetically modified to secrete at least one cytokine gene product are utilized to immunize the patient in a formulation with tumor antigens at a site other than an active tumor site. In another embodiment, cells genetically modified to express at least one tumor antigen gene product and to secrete at least one cytokine gene product are utilized in a formulation to immunize the patient at a site other than an active tumor site.

24 Claims, 15 Drawing Sheets

OTHER PUBLICATIONS

Borrelli, Emiliana, et al., "Targeting of an Inducible Toxic Phenotype in Animal Cells." Proc. Natl. Acad. Sci. USA. 85:7572–7576 (1988).

Lotze, Michael T. and Finn, Olivera J., "Recent Advances in Cellular Immunology: Implications for Immunity to Cancer." Immunotherapy Today 11:190–193 (1990).

Rosenberg, Steven et al., "Gene Transfer Into Humans–Immunotherapy of Patients with Advances Melanoma, Using Tumor–Infiltrating Lympocytes Modified by Retroviral Gene Transduction." New England J. Medicine. 323:570–578 (1990).

Ogura, Hiromi et al., "Implantation of Genetically Manipulated Fibroblasts into Mice as Antitumor α–Interferon Therapy." Cancer Research 50:5102–5106 (1990).

Cohen, J. Science 262:841–843 5 Nov. 1993.

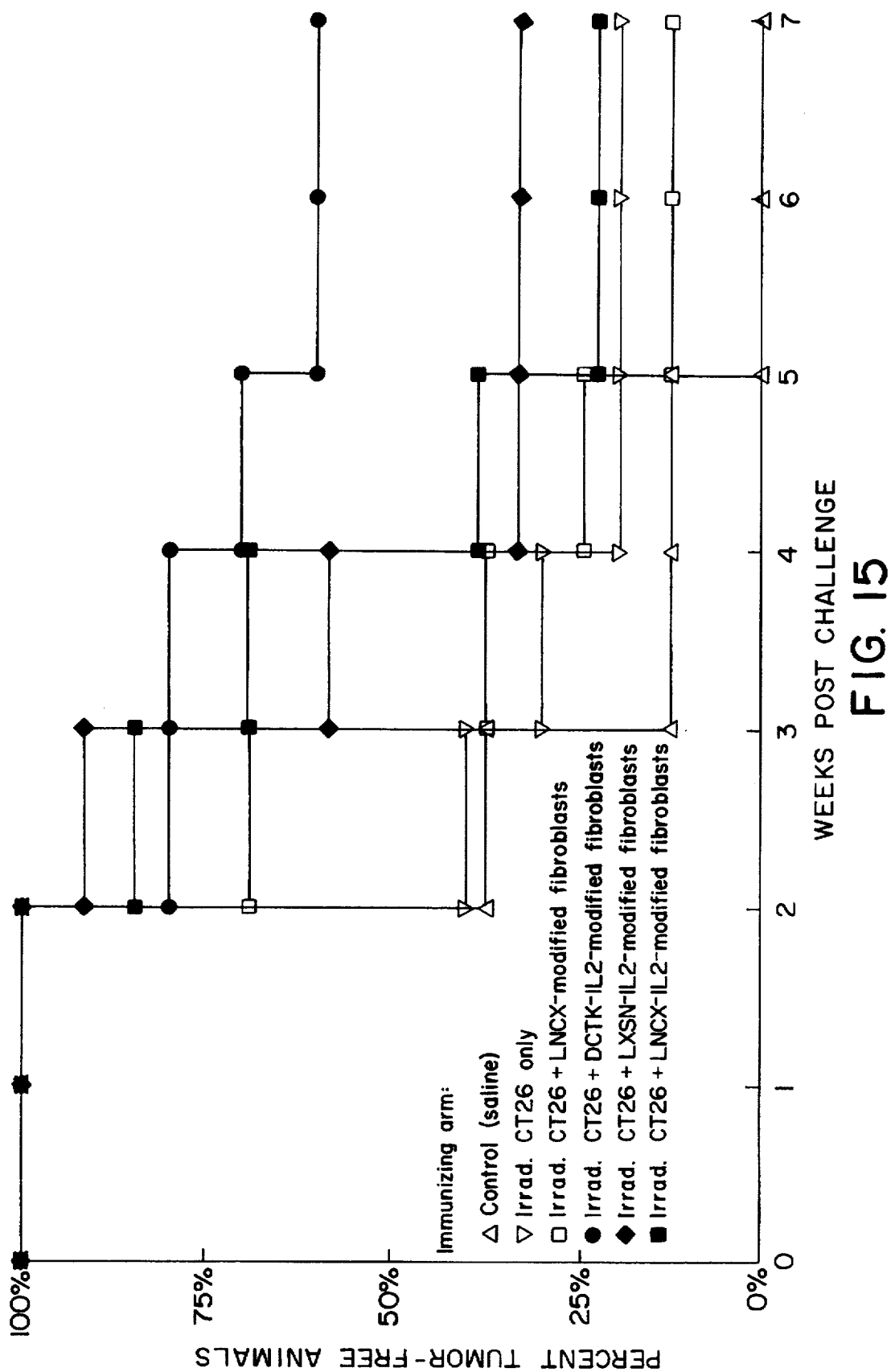

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6365 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: complement (1..6365)
        ( D ) OTHER INFORMATION: /note= "Complementary strand of pLXSN-RI- IL2"

( i x ) FEATURE:
        ( A ) NAME/KEY: CDS
        ( B ) LOCATION: 2557..3351

( x i ) SEQUENCE DESCRIPTION: SEQ ID NO:1:

```
TTTGAAAGAC  CCCACCCGTA  GGTGGCAAGC  TAGCTTAAGT  AACGCCACTT  TGCAAGGCAT      60

GGAAAAATAC  ATAACTGAGA  ATAGGAAAGT  TCAGATCAAG  GTCAGGAACA  AAGAAACAGC     120

TGAATACCAA  ACAGGATATC  TGTGGTAAGC  GGTTCCTGCC  CCGGCTCAGG  GCCAAGAACA     180
```

-continued

```
GATGAGACAG CTGAGTGATG GGCCAAACAG GATATCTGTG GTAAGCAGTT CCTGCCCCGG    240
 CTCGGGGCCA AGAACAGATG GTCCCCAGAT GCGGTCCAGC CCTCAGCAGT TTCTAGTGAA   300
TCATCAGATG TTTCCAGGGT GCCCCAAGGA CCTGAAAATG ACCCTGTACC TTATTTGAAC   360
TAACCAATCA GTTCGCTTCT CGCTTCTGTT CGCGCGCTTC CGCTCTCCGA GCTCAATAAA   420
AGAGCCCACA ACCCCTCACT CGGCGCGCCA GTCTTCCGAT AGACTGCGTC GCCCGGGTAC   480
CCGTATTCCC AATAAAGCCT CTTGCTGTTT GCATCCGAAT CGTGGTCTCG CTGTTCCTTG   540
GGAGGGTCTC CTCTGAGTGA TTGACTACCC ACGACGGGGG TCTTTCATTT GGGGCTCGT    600
CCGGGATTTG GAGACCCCTG CCCAGGGACC ACCGACCCAC CACCGGGAGG TAAGCTGGCC   660
AGCAACTTAT CTGTGTCTGT CCGATTGTCT AGTGTCTATG TTTGATGTTA TGCGCCTGCG   720
TCTGTACTAG TTAGCTAACT AGCTCTGTAT CTGGCGGACC CGTGGTGGAA CTGACGAGTT   780
CTGAACACCC GGCCGCAACC CTGGGAGACG TCCCAGGGAC TTTGGGGGCC GTTTTGTGG    840
CCCGACCTGA GGAAGGGAGT CGATGTGGAA TCCGACCCCG TCAGGATATG TGGTTCTGGT   900
AGGAGACGAG AACCTAAAAC AGTTCCCGCC TCCGTCTGAA TTTTTGCTTT CGGTTTGGAA   960
CCGAAGCCGC GCGTCTTGTC TGCTGCAGCA TCGTTCTGTG TTGTCTCTGT CTGACTGTGT  1020
TTCTGTATTT GTCTGAAAAT TAGGGCCAGA CTGTTACCAC TCCCTTAAGT TTGACCTTAG  1080
GTCACTGGAA AGATGTCGAG CGGATCGCTC ACAACCAGTC GGTAGATGTC AAGAAGAGAC  1140
GTTGGGTTAC CTTCTGCTCT GCAGAATGGC CAACCTTTAA CGTCGGATGG CCGCGAGACG  1200
GCACCTTTAA CCGAGACCTC ATCACCCAGG TTAAGATCAA GGTCTTTTCA CCTGGCCCGC  1260
ATGGACACCC AGACCAGGTC CCCTACATCG TGACCTGGGA AGCCTTGGCT TTTGACCCCC  1320
CTCCCTGGGT CAAGCCCTTT GTACACCCTA AGCCTCCGCC TCCTCTTCCT CCATCCGCCC  1380
CGTCTCTCCC CCTTGAACCT CCTCGTTCGA CCCCGCCTCG ATCCTCCCTT TATCCAGCCC  1440
TCACTCCTTC TCTAGGCGGG AATTCGTTAG CTTGGTAAGT GACCAGCTAC AGTCGGAAAC  1500
CATCAGCAAG CAGGTATGTA CTCTCCAGGG TGGGCCTGGC TTCCCCAGTC AAGACTCCAG  1560
GGATTTGAGG GACGCTGTGG GCTCTTCTCT TACATGTACC TTTTGCTAGC CTCAACCCTG  1620
ACTATCTTCC AGGTCATTGT TCCAACATGG CCCTGTGGAT CGACAGGATG CAACTCCTGT  1680
CTTGCATTGC ACTAAGTCTT GCACTTGTCA CAAACAGTGC ACCTACTTCA AGTTCTACAA  1740
AGAAAACACA GCTGCAACTG GAGCATTTAC TGCTGGATTT ACAGATGATT TTGAATGGAA  1800
TTAATAATTA CAAGAATCCC AAACTCACCC GCATGCTCAC ATTAAGTTT TACATGCCCA   1860
AGAAGGCCAC AGAACTGAAA CATCTGCAGT GTCTAGAAGA AGAACTCAAA CCTCTGGAGG  1920
AAGTGCTAAA TTTAGCTCAA AGCAAAAACT TTCACTTAAG GCCTAGGGAC TTAATCAGCA  1980
ATATCAACGT AATAGTTCTC GAGCTAAAGG GATCTGAAAC AACATTCATG TGTGAATATG  2040
CTGATGAGAC AGCCACCATT GTGGAATTTC TGAACAGATG GATTACCTTT TGTCAAAGCA  2100
TCATCTCAAC ACTAACTTGA TAATTAAGTG CTTCCCACTT AAAACATATC AGGATCCGCT  2160
GTGGAATGTG TGTCAGTTAG GGTGTGGAAA GTCCCCAGGC TCCCAGCAG GCAGAAGTAT   2220
GCAAAGCATG CATCTCAATT AGTCAGCAAC CAGGTGTGGA AAGTCCCCAG GCTCCCCAGC  2280
AGGCAGAAGT ATGCAAAGCA TGCATCTCAA TTAGTCAGCA ACCATAGTCC CGCCCCTAAC  2340
TCCGCCCATC CCGCCCCTAA CTCCGCCCAG TTCCGCCCAT TCTCCGCCCC ATGGCTGACT  2400
AATTTTTTTT ATTTATGCAG AGGCCGAGGC CGCCTCGGCC TCTGAGCTAT TCCAGAAGTA  2460
GTGAGGAGGC TTTTTTGGAG GCCTAGGCTT TTGCAAAAAG CTTGGGCTGC AGGTCGAGGC  2520
GGATCTGATC AAGAGACAGG ATGAGGATCG TTTCGC ATG ATT GAA CAA GAT GGA    2574
```

-continued

```
                                        Met  Ile  Glu  Gln  Asp  Gly
                                         1                    5
TTG  CAC  GCA  GGT  TCT  CCG  GCC  GCT  TGG  GTG  GAG  AGG  CTA  TTC  GGC  TAT      2622
Leu  His  Ala  Gly  Ser  Pro  Ala  Ala  Trp  Val  Glu  Arg  Leu  Phe  Gly  Tyr
               10                   15                        20

GAC  TGG  GCA  CAA  CAG  ACA  ATC  GGC  TGC  TCT  GAT  GCC  GCC  GTG  TTC  CGG      2670
Asp  Trp  Ala  Gln  Gln  Thr  Ile  Gly  Cys  Ser  Asp  Ala  Ala  Val  Phe  Arg
               25                   30                   35

CTG  TCA  GCG  CAG  GGG  CGC  CCG  GTT  CTT  TTT  GTC  AAG  ACC  GAC  CTG  TCC      2718
Leu  Ser  Ala  Gln  Gly  Arg  Pro  Val  Leu  Phe  Val  Lys  Thr  Asp  Leu  Ser
          40                   45                   50

GGT  GCC  CTG  AAT  GAA  CTG  CAG  GAC  GAG  GCA  GCG  CGG  CTA  TCG  TGG  CTG      2766
Gly  Ala  Leu  Asn  Glu  Leu  Gln  Asp  Glu  Ala  Ala  Arg  Leu  Ser  Trp  Leu
 55                        60                   65                        70

GCC  ACG  ACG  GGC  GTT  CCT  TGC  GCA  GCT  GTG  CTC  GAC  GTT  GTC  ACT  GAA      2814
Ala  Thr  Thr  Gly  Val  Pro  Cys  Ala  Ala  Val  Leu  Asp  Val  Val  Thr  Glu
                    75                   80                        85

GCG  GGA  AGG  GAC  TGG  CTG  CTA  TTG  GGC  GAA  GTG  CCG  GGG  CAG  GAT  CTC      2862
Ala  Gly  Arg  Asp  Trp  Leu  Leu  Leu  Gly  Glu  Val  Pro  Gly  Gln  Asp  Leu
               90                        95                       100

CTG  TCA  TCT  CAC  CTT  GCT  CCT  GCC  GAG  AAA  GTA  TCC  ATC  ATG  GCT  GAT      2910
Leu  Ser  Ser  His  Leu  Ala  Pro  Ala  Glu  Lys  Val  Ser  Ile  Met  Ala  Asp
          105                            110                      115

GCA  ATG  CGG  CGG  CTG  CAT  ACG  CTT  GAT  CCG  GCT  ACC  TGC  CCA  TTC  GAC      2958
Ala  Met  Arg  Arg  Leu  His  Thr  Leu  Asp  Pro  Ala  Thr  Cys  Pro  Phe  Asp
     120                      125                      130

CAC  CAA  GCG  AAA  CAT  CGC  ATC  GAG  CGA  GCA  CGT  ACT  CGG  ATG  GAA  GCC      3006
His  Gln  Ala  Lys  His  Arg  Ile  Glu  Arg  Ala  Arg  Thr  Arg  Met  Glu  Ala
135                      140                      145                      150

GGT  CTT  GTC  GAT  CAG  GAT  GAT  CTG  GAC  GAA  GAG  CAT  CAG  GGG  CTC  GCG      3054
Gly  Leu  Val  Asp  Gln  Asp  Asp  Leu  Asp  Glu  Glu  His  Gln  Gly  Leu  Ala
                         155                      160                      165

CCA  GCC  GAA  CTG  TTC  GCC  AGG  CTC  AAG  GCG  CGC  ATG  CCC  GAC  GGC  GAG      3102
Pro  Ala  Glu  Leu  Phe  Ala  Arg  Leu  Lys  Ala  Arg  Met  Pro  Asp  Gly  Glu
               170                      175                      180

GAT  CTC  GTC  GTG  ACC  CAT  GGC  GAT  GCC  TGC  TTG  CCG  AAT  ATC  ATG  GTG      3150
Asp  Leu  Val  Val  Thr  His  Gly  Asp  Ala  Cys  Leu  Pro  Asn  Ile  Met  Val
          185                      190                      195

GAA  AAT  GGC  CGC  TTT  TCT  GGA  TTC  ATC  GAC  TGT  GGC  CGG  CTG  GGT  GTG      3198
Glu  Asn  Gly  Arg  Phe  Ser  Gly  Phe  Ile  Asp  Cys  Gly  Arg  Leu  Gly  Val
     200                      205                      210

GCG  GAC  CGC  TAT  CAG  GAC  ATA  GCG  TTG  GCT  ACC  CGT  GAT  ATT  GCT  GAA      3246
Ala  Asp  Arg  Tyr  Gln  Asp  Ile  Ala  Leu  Ala  Thr  Arg  Asp  Ile  Ala  Glu
215                      220                      225                      230

GAG  CTT  GGC  GGC  GAA  TGG  GCT  GAC  CGC  TTC  CTC  GTG  CTT  TAC  GGT  ATC      3294
Glu  Leu  Gly  Gly  Glu  Trp  Ala  Asp  Arg  Phe  Leu  Val  Leu  Tyr  Gly  Ile
                    235                      240                      245

GCC  GCT  CCC  GAT  TCG  CAG  CGC  ATC  GCC  TTC  TAT  CGC  CTT  CTT  GAC  GAG      3342
Ala  Ala  Pro  Asp  Ser  Gln  Arg  Ile  Ala  Phe  Tyr  Arg  Leu  Leu  Asp  Glu
               250                      255                      260

TTC  TTC  TGAGCGGGAC  TCTGGGGTTC  GATAAAATAA  AAGATTTTAT  TTAGTCTCCA              3398
Phe  Phe
     265

GAAAAAGGGG  GGAATGAAAG  ACCCCACCTG  TAGGTTTGGC  AAGCTAGCTT  AAGTAACGCC              3458

ATTTTGCAAG  GCATGGAAAA  ATACATAACT  GAGAATAGAG  AAGTTCAGAT  CAAGGTCAGG              3518

AACAGATGGA  ACAGCTGAAT  ATGGGCCAAA  CAGGATATCT  GTGGTAAGCA  GTTCCTGCCC              3578

CGGCTCAGGG  CCAAGAACAG  ATGGAACAGC  TGAATATGGG  CCAAACAGGA  TATCTGTGGT              3638

AAGCAGTTCC  TGCCCCGGCT  CAGGGCCAAG  AACAGATGGT  CCCCAGATGC  GGTCCAGCCC              3698
```

```
TCAGCAGTTT CTAGAGAACC ATCAGATGTT TCCAGGGTGC CCCAAGGACC TGAAATGACC    3758
CTGTGCCTTA TTTGAACTAA CCAATCAGTT CGCTTCTCGC TTCTGTTCGC GCGCTTCTGC    3818
TCCCCGAGCT CAATAAAAGA GCCCACAACC CCTCACTCGG GGCGCCAGTC CTCCGATTGA    3878
CTGAGTCGCC CGGGTACCCG TGTATCCAAT AAACCCTCTT GCAGTTGCAT CCGACTTGTG    3938
GTCTCGCTGT TCCTTGGGAG GGTCTCCTCT GAGTGATTGA CTACCCGTCA GCGGGGGTCT    3998
TTCATTTGGG GGCTCGTCCG GGATCGGGAG ACCCCTGCCC AGGGACCACC GACCCACCAC    4058
CGGGAGGTAA GCTGGCTGCC TCGCGCGTTT CGGTGATGAC GGTGAAAACC TCTGACACAT    4118
GCAGCTCCCG GAGACGGTCA CAGCTTGTCT GTAAGCGGAT GCCGGGAGCA GACAAGCCCG    4178
TCAGGGCGCG TCAGCGGGTG TTGGCGGGTG TCGGGCGCA GCCATGACCC AGTCACGTAG    4238
CGATAGCGGA GTGTATACTG GCTTAACTAT GCGGCATCAG AGCAGATTGT ACTGAGAGTG    4298
CACCATATGC GGTGTGAAAT ACCGCACAGA TGCGTAAGGA GAAAATACCG CATCAGGCGC    4358
TCTTCCGCTT CCTCGCTCAC TGACTCGCTG CGCTCGGTCG TTCGGCTGCG GCGAGCGGTA    4418
TCAGCTCACT CAAAGGCGGT AATACGGTTA TCCACAGAAT CAGGGGATAA CGCAGGAAAG    4478
AACATGTGAG CAAAAGGCCA GCAAAAGGCC AGGAACCGTA AAAAGGCCGC GTTGCTGGCG    4538
TTTTTCCATA GGCTCCGCCC CCCTGACGAG CATCACAAAA ATCGACGCTC AAGTCAGAGG    4598
TGGCGAAACC CGACAGGACT ATAAAGATAC CAGGCGTTTC CCCCTGGAAG CTCCCTCGTG    4658
CGCTCTCCTG TTCCGACCCT GCCGCTTACC GGATACCTGT CCGCCTTTCT CCCTTCGGGA    4718
AGCGTGGCGC TTTCTCATAG CTCACGCTGT AGGTATCTCA GTTCGGTGTA GGTCGTTCGC    4778
TCCAAGCTGG GCTGTGTGCA CGAACCCCCC GTTCAGCCCG ACCGCTGCGC CTTATCCGGT    4838
AACTATCGTC TTGAGTCCAA CCCGGTAAGA CACGACTTAT CGCCACTGGC AGCAGCCACT    4898
GGTAACAGGA TTAGCAGAGC GAGGTATGTA GGCGGTGCTA CAGAGTTCTT GAAGTGGTGG    4958
CCTAACTACG GCTACACTAG AAGGACAGTA TTTGGTATCT GCGCTCTGCT GAAGCCAGTT    5018
ACCTTCGGAA AAAGAGTTGG TAGCTCTTGA TCCGGCAAAC AAACCACCGC TGGTAGCGGT    5078
GGTTTTTTTG TTTGCAAGCA GCAGATTACG CGCAGAAAAA AAGGATCTCA AGAAGATCCT    5138
TTGATCTTTT CTACGGGGTC TGACGCTCAG TGGAACGAAA ACTCACGTTA AGGGATTTTG    5198
GTCATGAGAT TATCAAAAAG GATCTTCACC TAGATCCTTT TAAATTAAAA ATGAAGTTTT    5258
AAATCAATCT AAAGTATATA TGAGTAAACT TGGTCTGACA GTTACCAATG CTTAATCAGT    5318
GAGGCACCTA TCTCAGCGAT CTGTCTATTT CGTTCATCCA TAGTTGCCTG ACTCCCCGTC    5378
GTGTAGATAA CTACGATACG GGAGGGCTTA CCATCTGGCC CCAGTGCTGC AATGATACCG    5438
CGAGACCCAC GCTCACCGGC TCCAGATTTA TCAGCAATAA ACCAGCCAGC CGGAAGGGCC    5498
GAGCGCAGAA GTGGTCCTGC AACTTTATCC GCCTCCATCC AGTCTATTAA TTGTTGCCGG    5558
GAAGCTAGAG TAAGTAGTTC GCCAGTTAAT AGTTTGCGCA ACGTTGTTGC CATTGCTGCA    5618
GGCATCGTGG TGTCACGCTC GTCGTTTGGT ATGGCTTCAT TCAGCTCCGG TTCCCAACGA    5678
TCAAGGCGAG TTACATGATC CCCCATGTTG TGCAAAAAAG CGGTTAGCTC CTTCGGTCCT    5738
CCGATCGTTG TCAGAAGTAA GTTGGCCGCA GTGTTATCAC TCATGGTTAT GGCAGCACTG    5798
CATAATTCTC TTACTGTCAT GCCATCCGTA AGATGCTTTT CTGTGACTGG TGAGTACTCA    5858
ACCAAGTCAT TCTGAGAATA GTGTATGCGG CGACCGAGTT GCTCTTGCCC GGCGTCAACA    5918
CGGGATAATA CCGCGCCACA TAGCAGAACT TTAAAAGTGC TCATCATTGG AAAACGTTCT    5978
TCGGGGCGAA AACTCTCAAG GATCTTACCG CTGTTGAGAT CCAGTTCGAT GTAACCCACT    6038
CGTGCACCCA ACTGATCTTC AGCATCTTTT ACTTTCACCA GCGTTTCTGG GTGAGCAAAA    6098
```

```
ACAGGAAGGC  AAAATGCCGC  AAAAAAGGGA  ATAAGGGCGA  CACGGAAATG  TTGAATACTC      6158

ATACTCTTCC  TTTTTCAATA  TTATTGAAGC  ATTTATCAGG  GTTATTGTCT  CATGAGCGGA      6218

TACATATTTG  AATGTATTTA  GAAAATAAA   CAAATAGGGG  TTCCGCGCAC  ATTTCCCCGA      6278

AAAGTGCCAC  CTGACGTCTA  AGAAACCATT  ATTATCATGA  CATTAACCTA  TAAAAATAGG      6338

CGTATCACGA  GGCCCTTTCG  TCTTCAA                                              6365
```

( 2 ) INFORMATION FOR SEQ ID NO:2:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ile Glu Gln Asp Gly Leu His Ala Gly Ser Pro Ala Ala Trp Val
 1           5                  10                      15

Glu Arg Leu Phe Gly Tyr Asp Trp Ala Gln Gln Thr Ile Gly Cys Ser
             20                  25                  30

Asp Ala Ala Val Phe Arg Leu Ser Ala Gln Gly Arg Pro Val Leu Phe
         35                  40                  45

Val Lys Thr Asp Leu Ser Gly Ala Leu Asn Glu Leu Gln Asp Glu Ala
     50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
             115                 120                 125

Ala Thr Cys Pro Phe Asp His Gln Ala Lys His Arg Ile Glu Arg Ala
         130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                 165                 170                 175

Arg Met Pro Asp Gly Glu Asp Leu Val Val Thr His Gly Asp Ala Cys
             180                 185                 190

Leu Pro Asn Ile Met Val Glu Asn Gly Arg Phe Ser Gly Phe Ile Asp
         195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260
```

LYMPHOKINE GENE THERAPY OF CANCER

This application is a continuation of application Ser. No. 07/863,641, filed Apr. 3, 1992, now abandoned, which is a continuation-in-part of U.S. patent application Ser. No. 07/781,356, filed on Oct. 25, 1991, now abandoned, which is a continuation-in-part of U.S. patent application Ser. No. 07/720,872, filed on Jun. 25, 1991, now abandoned, both of which are incorporated herein in their entirety.

BACKGROUND

Recent advances in our understanding of the biology of the immune system have lead to the identification of important modulators of immune responses, called cytokines (1–3). Immune system modulators produced by lymphocytes are termed lymphokines, a subset of the cytokines. These agents mediate many of the immune responses involved in anti-tumor immunity. Several of these cytokines have been produced by recombinant DNA methodology and evaluated for their anti-tumor effects. The administration of lymphokines and related immunomodulators has resulted in objective tumor responses in patients with various types of neoplasms (4–7). However, current modes of cytokine administration are frequently associated with toxicities that limit the therapeutic value of these agents.

For example, interleukin-2 (IL-2) is an important lymphokine in the generation of anti-tumor immunity (4). In response to tumor antigens, a subset of lymphocytes termed helper T-cells secrete small quantities of IL-2. This IL-2 acts locally at the site of tumor antigen stimulation to activate cytotoxic T-cells and natural killer cells which mediate systemic tumor cell destruction. Intravenous, intralymphatic and intralesional administration of IL-2 has resulted in clinically significant responses in some cancer patients (4–6). However, severe toxicities (hypotension and adema) limit the dose and efficacy of intravenous and intralymphatic IL- 2 administration (5–7). The toxicity of systemically administered lymphokines is not surprising as these agents mediate local cellular interactions and they are normally secreted in only very small quantities.

Additionally, other cytokines, such as interleukin-4 (IL-4), alpha interferon (α-INF) and gamma interferon (c-INF) have been used to stimulate immune responses to tumor cells. Like IL-2, the current modes of administration have adverse side effects.

To circumvent the toxicity of systemic cytokine administration, several investigators have examined intralesional injection of IL-2. This approach eliminates the toxicity associated with systemic IL-2 administration (8,9,10). However, multiple intralesional injections are required to optimize therapeutic efficacy (9,10). Hence, these injections are impractical for many patients, particularly when tumor sites are not accessible for injection without potential morbidity.

An alternative approach, involving cytokine gene transfer into tumor cells, has resulted in significant anti-tumor immune responses in several animal tumor models (11–14). In these studies, the expression of cytokine gene products following cytokine gene transfer into tumor cells has abrogated the tumorigenicity of the cytokine-secreting tumor cells when implanted into syngeneic hosts. The transfer of genes for IL-2 (11,12) c-INF (13) or interleukin-4 (IL-4) (14) significantly reduced or eliminated the growth of several different histological types of murine tumors. In the studies employing IL-2 gene transfer, the treated animals also developed systemic anti-tumor immunity and were protected against subsequent tumor challenges with the unmodified parental tumor (11,12). Similar inhibition of tumor growth and protective immunity was also demonstrated when immunizations were performed with a mixture of unmodified parental tumor cells and genetically modified tumor cells engineered to express the IL-2 gene. No toxicity associates with localized lymphokine transgene expression was reported in these animal tumor studies (11–14).

While the above gene-transfer procedure has been shown to provide anti-tumor immunity, it still retains practical difficulties. This approach is limited by the inability to transfer functional cytokine genes into many patients' tumor cells, as most patients' tumors cannot be established to grown in vitro and methods for human in vivo gene transfer are not available.

SUMMARY OF THE INVENTION

The present invention demonstrates a novel, more practical method of cytokine cancer immunotherapy. In one approach, selected cells from a patient, such as fibroblasts, obtained, for example, from a routine skin biopsy, are genetically modified to express one or more cytokines. Alternatively, patient cells which may normally serve as antigen presenting cells in the immune system such as macrophages, monocytes, and lymphocytes may also be genetically modified to express one or more cytokines. These modified cells are hereafter called cytokine-expressing cells, ore CE cells. The CE cells are then mixed with the patient's tumor antigens, for example in the form of irradiated tumor cells, or alternatively in the form of purified natural or recombinant tumor antigen, and employed in immunizations, for example subcutaneously, to induce systemic anti-tumor immunity.

The cytokines are locally expressed at levels sufficient to induce or augment systemic anti-tumor immune responses via local immunization at sites other than active tumor sites. Systemic toxicity related to cytokine administration should not occur because the levels of cytokine secreted by the CE cells should not significantly affect systemic cytokine concentrations.

As the amount of cytokine secreted by the CE cells is sufficient to induce anti-tumor immunity but is too low to produce substantial systemic toxicity, this approach provides the benefit of local cytokine administration. In addition, this novel method obviates the need for intralesional injections, which may produce morbidity. Furthermore, the continuous local expression of cytokine(s) at the sites of immunization may also augment anti-tumor immune responses compared to intermittent cytokine injections. This method also provides the advantage of local immunization with the CE cells, as opposed to cumbersome intravenous infusions. This method also eliminates the need for establishing tumor cell lines in vitro as well as transfer of genes into these tumor cells.

This invention also provides an alternative means of localized expression of cytokines to induce and/or increase immune responses to a patient's tumor through genetic modification of cellular expression of both cytokine(s) and tumor antigen(s). In this embodiment, selected cells from a patient are isolated and transduced with cytokine gene(s) as well as gene(s) coding for tumor antigen(s). The transduced cells are called "carrier cells." Carrier cells can include fibroblasts and cells which may normally serve as antigen presenting cells in the immune system such as macrophages, monocytes, and lymphocytes. Transduced carrier cells actively expressing both the cytokine(s) and the tumor antigen(s) are selected and utilized in local immunizations at a site other than active tumor sites to induce anti-tumor immune responses. As with the CE cells, these carrier cells should not produce substantial systemic toxicities, as the levels of cytokine(s) secreted by the carrier cells should not significantly affect systemic cytokine concentrations. This alternate embodiment is advantageous because it obviates the need to obtain samples of the tumor, which is sometimes difficult. However, carrier cells can be utilized in local immunizations in conjunction with tumor cells, tumor cell homogenates, purified tumor antigens, or recombinant tumor antigens to enhance anti-tumor immunity.

Additionally, this second embodiment retains the same advantages as the first embodiment in that the level of cytokine released by the carrier cells is sufficient to induce anti-tumor immunity but is too low to produce substantial systemic toxicity. In addition, as with the first embodiment, this method obviates the need for intralesional injections, and allows for continuous expression of cytokine(s). This method also eliminates the need for establishing continuous cultures in vitro of tumor cells as well as transfer of genes into these tumor cells, and provides the advantage of local immunization with the carrier cells, as opposed to cumbersome lengthy intravenous infusions.

These approaches may also find application in inducing or augmenting immune responses to other antigens of clinical significance in other areas of medical practice.

BRIEF DESCRIPTION OF THE DRAWINGS

FIG. 15 shows the effect of IL-2 modified fibroblasts on induction of systemic anti-tumor immunity and the time of tumor onset for the individual animal in each treatment group. Mice were immunized with $2 \times 10^6$ fibroblasts mixed with $2.5 \times 10^5$ irradiated CT26 tumor cells 14 days prior to challenge with $5 \times 10^4$ fresh tumor cells.

DETAILED DESCRIPTION

Figure 1:
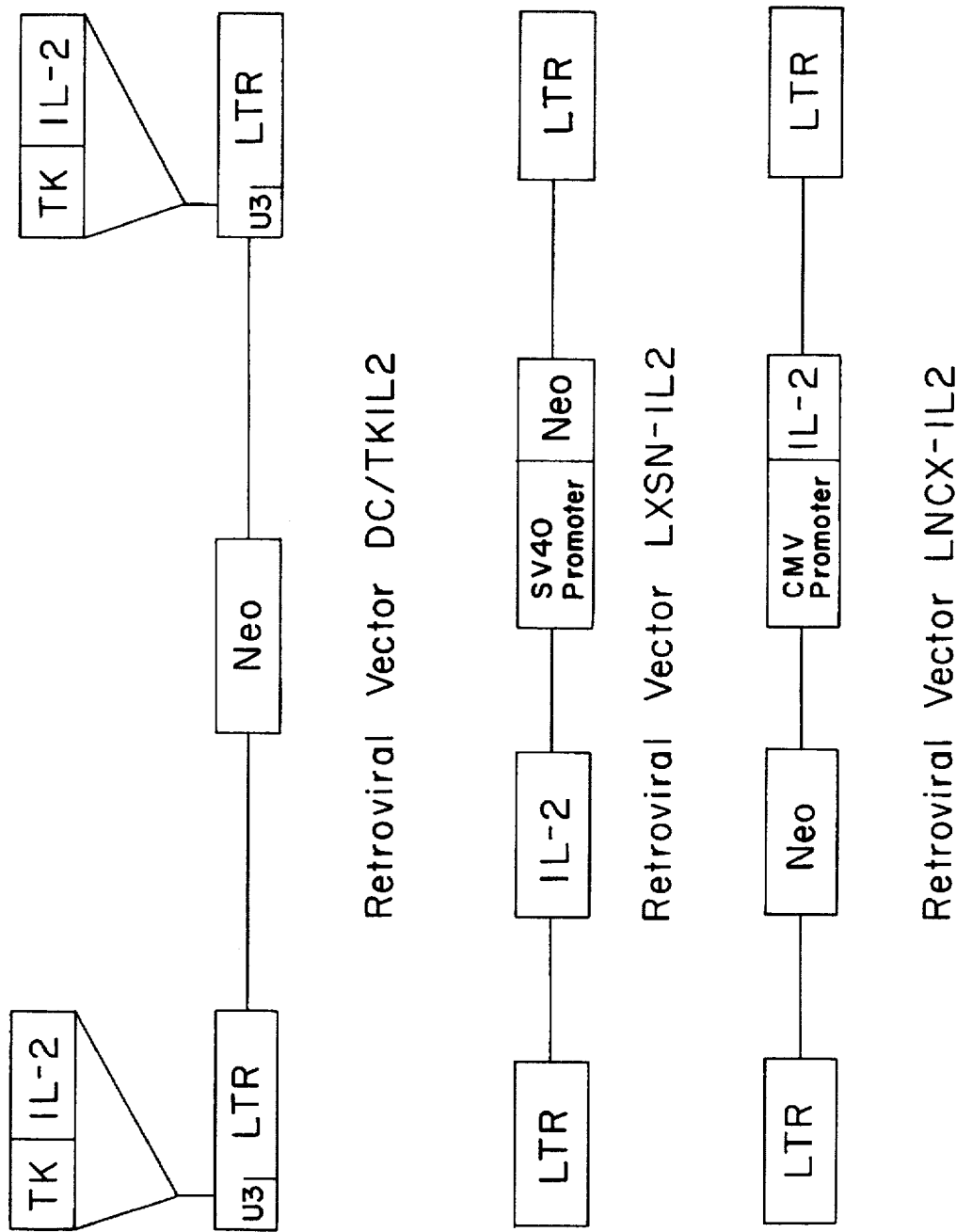
FIG. 1 shows schematic diagrams of retroviral vectors DC/TKIL2, LXSN-IL2, and LNCX-IL2.

A novel method of tumor immunotherapy is described comprising the genetic modification of cells resulting in the secretion of cytokine gene products to stimulate a patient's immune response to tumor antigens. "Gene" is defined herein to be a nucleotide sequence encoding the desired protein. In one embodiment, autologous fibroblasts genetically modified to secrete at least one cytokine gene product are utilized to immunize the patient in a formulation with tumor antigens at a site other than an active tumor site. In another embodiment, cells genetically modified to express at least one tumor antigen gene product and to secrete at least one cytokine gene product are utilized in formulation to immunize the patient at a site other than an active tumor site. Cytokines are preferably expressed in cells which efficiently secrete these proteins into the surrounding milieu. Fibroblasts are an example of such cells. Fibroblasts or other cells can be genetically modified to express and secrete one or more cytokines, as described later in this specification.

Tumor antigens can be provided by several methods, including, but not limited to the following: 1) CE cells can be transduced with gene(s) coding for tumor antigens. These "carrier cells" are then utilized in patient immunizations. 2) Cloned gene sequences coding for appropriate tumor antigens can be transferred into cells such as fibroblasts or antigen-presenting cells. These cells are then mixed with CE or carrier cells to immunize the patient. 3) Tumor antigens can be cloned in bacteria or other types of cells by recombinant procudures. These antigens are then purified and employed an immunization with CE and/or carrier cells. 4) Tumor antigens can be purified from tumor cells and used, along with CE or carrier cells, to immunize the patient. 5) Tumor cells may be irradiated or mechanically disrupted and mixed with CE and/or carrier cells for patient immunizations.

This invention encompasses the following steps: (A) isolation of appropriate cells for generation of CE cells or carrier cells; (B) isolation of cytokine genes or isolation of cytokine genes and tumor antigen genes, as well as appropriate marker and/or suicide genes; (C) transfer of the genes from (B) to produce the CE cells or carrier cells; (D) preparation of immunological samples of the patient's tumor antigens or other suitable tumor antigens for immunization with CE or carrier cells; (E) inactivation of the malignant potential of tumor cells if they are used as a source of tumor antigens for immunization; and (F) preparation of samples for immunization. Following are several embodiments contemplated by the inventors. However, it is understood that any means known by those in the art to accomplish these steps will be usable in this invention.

(A) Isolation of Cells to Generate CE and Carrier Cells

Cells to be utilized as CE cells and carrier cells can be selected from a variety of locations in the patient's body. For example, skin punch biopsies provide a readily available source of fibroblasts for use in generating CE cells, with a minimal amount of intrusion to the patient. Alternatively, these fibroblasts can be obtained from the tumor sample itself. Cells of hematopoietic origin may be obtained by venipuncture, bone marrow aspiration, lymph node biopsies, or from tumor samples. Other appropriate cells for the generation of CE or carrier cells can be isolated by means known in the art. Non-autologous cells similarly selected and processed can also be used.

(B) Isolation of Genes

Numerous cytokine genes have been cloned and are available for use in this protocol. The genes for IL-2, c-INF and other cytokines are readily available (1–5, 11–14). Cloned genes of the appropriate tumor antigens are isolated according to means known in the art.

Selectable marker genes such as neomycin resistance ($Neo^R$) are readily available. Incorporation of a selectable marker gene(s) allows for the selection of cells that have successfully received and express the desired genes. Other selectable markers known to those in the art of gene transfer may also be utilized to generate CE cells or carrier cells expressing the desired transgenes.

"Suicide" genes can be incorporated into the CE cells or carrier cells to allow for selective inducible killing after stimulation of the immune response. A gene such as the herpes simplex virus thymidine kinase gene (TK) can be used to create an inducible destruction of the CE cells or carrier cells. When the CE cells or carrier cells are no longer useful, a drug such as acyclovir or gancyclovir can be administered. Either of these drugs will selectively kill cells expressing TK, thus eliminating the implanted transduced cells. Additionally, a suicide gene may be a gene coding for a non-secreted cytotoxic polypeptide attached to an inducible promoter. When destruction of the CE or carrier cells is desired, the appropriate inducer of the promoter is administered so that the suicide gene is induced to produce cytotoxic polypeptide which subsequently kills the CE or carrier cell. However, destruction of the CE or carrier cells may not be required.

Genes coding for tumor antigen(s) of interest can be cloned by recombinant methods. The coding sequence of an antigen expressed by multiple tumors may be utilized for many individual patients.

(C) Transfer of Genes

Numerous methods are available for transferring genes into cultured cells (15). For example, the appropriate genes can be inserted into vectors such as plasmids or retroviruses and transferred into the cells. Electroporation, lipofection and a variety of other methods are known in the field and can be implemented.

One method for gene transfer is a method similar to that employed in previous human gene transfer studies, where tumor infiltrating lymphocytes (TILs) were modified by retroviral gene transduction and administered to cancer patients (16). In this Phase I safety study of retroviral mediated gene transfer, TILs were genetically modified to express the Neomycin resistance ($Neo^R$) gene. Following intravenous infusion, polymerase chain reaction analyses consistently found genetically modified cells in the circulation for as long as two months after administration. No infectious retroviruses were identified in these patients and no side effects due to gene transfer were noted in any patients (16). These retroviral vectors have been altered to prevent viral replication by the deletion of viral gag, pol and env genes.

When retroviruses are used for gene transfer, replication competent retroviruses may theoretically develop by recombination between the retroviral vector and viral gene sequences in the packaging cell line utilized to produce the retroviral vector. We will use packaging cell lines in which the production of replication competent virus by recombination has been reduced or eliminated. Hence, all retroviral vector supernatants used to infect patient cells will be screened for replication competent virus by standard assays such as PCR and reverse transcriptase assays (16). Furthermore, exposure to replication competent virus may not be harmful. In studies of subhuman primates injected with a large inoculum of replication competent murine retrovirus, the retrovirus was cleared by the primate immune system (17). No clinical illnesses or sequelae resulting from replication competent virus have been observed three years after exposure. In summary, it is not expected that patients will be exposed to replication competent murine retrovirus and it appears that such exposure may not be deleterious (17).

(D) Preparation of Immunological Samples of the Patient's Tumor Antigens or Purified Recombinant Tumor Antigens Tumor cells bearing tumor associated antigens are isolated from the patient. These cells can derive either from solid tumors or from leukemic tumors. For solid tumors, single-cell suspensions can be made by mechanical separation and washing of biopsy tissue (18).

Hematopoietic tumors may be isolated from peripheral blood or bone marrow by standard methods (19).

A second variant is the use of homogenates of tumor cells. Such homogenates would contain tumor antigens available for recognition by the patient's immune system upon stimulation by this invention. Either unfractionated cell homogenates, made, for example, by mechanical disruption or by freezing and thawing the cells, or fractions of homogenates preferably with concentrated levels of tumor antigens, can be used.

Likewise, purified tumor antigens, obtained for example by immunoprecipitation or recombinant DNA methods, could be used. Purified antigens would then be utilized for immunizations together with the CE cells and/or carrier cells described above to induce or enhance the patient's immune response to these antigens.

In the embodiments employing carrier cells, tumor antigens are available through their expression by the carrier cells. These carrier cells can be injected alone or in conjunction with other tumor antigen preparations or CE cells. Likewise, when CE cells are used, purified recombinant tumor antigen, produced by methods known in the art, can be used.

If autologous tumor cells are not readily available, heterologous tumor cells, their homogenates, their purified antigens, or carrier cells expressing such antigens could be used.

(E) Inactivation of Tumor Cells

When viable tumor cells are utilized in immunizations as a source of tumor antigens, the tumor cells can be inactivated so that they do not grow in the patient. Inactivation can be accomplished by several methods. The cells can be irradiated prior to immunization (18). This irradiation will be at a level which will prevent their replication. Such viable calls can then present their tumor antigens to the patient's immune system, but cannot multiply to create new tumors.

Alternatively, tumor cells that can be cultured may be transduced with a suicide gene. As described above, a gene such as the herpes simplex thymidine kinase (TK) gene can be transferred into tumor cells to induce their destruction by administration of acyclovir or gancyclovir. After immunization, the TK expressing tumor cells can present their tumor antigens, and are capable of proliferation. After a period of time during which the patients's immune response is stimulated, the cells can be selectively killed. This approach might allow longer viability of the tumor cells utilized for immunizations, which may be advantageous in the induction or augmentation of anti-tumor immunity.

(F) Preparation of Samples for Immunization

CE cells and/or carrier cells and tumor cells, and/or homogenates of tumor cells and/or purified tumor antigen (s), are combined for patient immunization. Approximately $10^7$ tumor cells will be required. If homogenates of tumor cells or purified or non-purified fractions of tumor antigens are used, the tumor dose can be adjusted based on the normal number of tumor antigens usually present on $10^7$ intact tumor cells. The tumor preparation should be mixed with numbers of CE or carrier cells sufficient to secrete cytokine levels that induce anti-tumor immunity (11-12) without producing substantial systemic toxicity which would interfere with therapy.

The cytokines should be produced by the CE cells or the carrier cells at levels sufficient to induce or augment immune response but low enough to avoid substantial systemic toxicity. This prevents side effects created by previous methods' administration of greater than physiological levels of the cytokines.

These mixtures, as well as carrier cells that are utilized alone, will be formulated for injection in any manner known in the art acceptable for immunization. Because it is important that at least the CE cells and carrier cells remain viable, the formulations must be compatible with cell survival. Formulations can be injected subcutaneously, intramuscularly, or in any manner acceptable for immunization.

Contaminants in the preparation which may focus the immune response on undesired antigens should be removed prior to the immunizations.

The following examples are provided for illustration of several embodiments of the invention and should not be interpreted as limiting the scope of the invention.

EXAMPLE I

Immunization with Fibroblasts Expressing IL-2 Mixed with Irradiated Tumor Cells

1) Isolation of Autologous Fibroblasts for Use in Generating IL-2 Secreting CE Cells Skin punch biopsies will be obtained from each patient under sterile conditions. The biopsy tissue will be minced and placed in RPMI 1640 media containing 10% fetal calf serum (or similar media) to establish growth of the skin fibroblasts in culture. The cultured fibroblasts will be utilized to generate IL-2 secreting CE cells by retroviral mediated IL-2 gene transfer.

2) Retrovital Vector Preparation and Generation of IL-2 Secreting CE Cells

The cultured skin fibroblasts will then be infected with a retroviral vector containing the IL-2 and Neomycin resistance ($Neo^R$) genes. An N2 vector containing the $Neo^R$ gene will be used, and has been previously utilized by a number of investigators for in vitro and in vivo work, including investigations with human subjects (16). The IL-2 vector will be generated from an N2-derived vector, LLRNL, developed and described by Friedmann and his colleagues (20). It will be made by replacement of the luciferase gene of LLRNL with a full-length cDNA encoding human IL-2. Retroviral vector free of contaminating replication-competent virus is produced by transfection of vector plasmid constructions into the helper-free packaging cell line PA317. Before infection of patients' cells, the vector will have been shown to be free of helper virus. In the event that helper virus is detected, the vector will be produced in the GP+envAM12 packaging cell line in which the viral gag and pol genes are separated from the env, further reducing the likelihood of helper virus production.

3) Transduction Protocol

The cultured primary fibroblasts will be incubated with supernatant from the packaging cell line as described (20). Supernatant from these cells will be tested for adventitious agents and replication competent virus as described (16) and outlined in Table 1. The fibroblasts are washed and then grown in culture media containing G418, (a neomycin analogue) to select for transduced cells expressing the $Neo^R$ gene. The G418-resistant cells will be tested for expression of the IL-2 gene by measuring the concentration of IL-2 in the culture supernatant by an enzyme linked immunosorbent assay (ELISA) (12). G418-resilient cells expressing IL-2 will be stored at −70° C. until required for subsequent use in immunizations.

TABLE 1

Adventitious Agents and Safety Testing

1. Sterility
2. Mycoplasma
3. General Safety
4. Viral Testing
   LCM Virus
   Thymic agent
   S+/L– eco
   S+/L– xeno
   S+/L– ampho
   3T3 amplification
   MRC-5/Vero 4) Preparation of Irradiated Tumor Cells Tumors obtained form clinically indicated surgical resections or from superficial lymph node or skin metastases will be minced into 2–3 mm pieces and treated with collagenase and DNAse to facilitate separation of the tumor into a single cell suspension. The collected cells will be centrifuged and washed in RPMI 1640 media and then cryopreserved in a solution containing 10% dimethyl sulphoxide and 50% fetal calf serum in RPMI 1640 media. The cells will be stored in liquid nitrogen until the time of administration. Prior to their use in subcutaneous immunizations, the cells will be thawed, washed in media free of immunogenic contaminants, and irradiated with 4,000 rads per minute for a total of 20,000 rads in a cesium irradiator.

5) Patient Selection

Patients will have a histologically confirmed diagnosis of cancer. Patients with tumors that must be resected for therapeutic purposes or with tumors readily accessible for biopsy are most appropriate for this embodiment of the invention.

6) Pretreatment Evaluation

The following pretreatment evaluations will be performed:

1) History and physical examination including a description and quantification of disease activity.

2) Performance Status Assessment
   0=Normal, no symptoms
   1=Restricted, but ambulatory
   2=Up greater than 50% of waking hours, capable of self-care
   3=Greater than 50% of waking hours confined to bed or chair, limited self-care
   4=Bedridden 3) Pretreatment Laboratory:
   CBC with differential, platelet count, PT, PTT, glucose, BUN, creatinine, electrolytes, SGOT, SGPT, LDH, alkaline phosphatase, bilirubin, uric acid, calcium, total protein albumin.

4) Other Analyses:
   Urinalysis
   $CH_{50}$, $C_3$ and $C_4$ serum complement levels Immunophenotyping of peripheral blood B cell and T cell subsets
   Assays for detectable replication-competent virus in peripheral blood cells
   PCR assays of peripheral blood leukocytes for $Neo^R$, IL-2 and viral env 5) Other Pretreatment Evaluation:
   Chest X-ray and other diagnostic studies including computerized tomography (CT), magnetic resonance imaging (MRI) or radionuclide scans may be performed to document and quantify the extent of disease activity.

Follow-up evaluations of these assessments at regular intervals during the course of therapy (approximately every 1 to 3 months) will be useful in determining response to therapy and potential toxicity, permitting adjustments in the number of immunizations administered.

7) Restrictions on Concurrent Therapy

For optimal effects of this treatment, patients should receive no concurrent therapy which is known to suppress the immune system.

8) Final Formulation

Each patient will receive subcutaneous immunizations with a mixture if irradiated tumor cells and autologous fibroblast CE cells genetically modified to secrete IL-2. Approximately $10^7$ tumor cells will be mixed with $10^7$ fibroblasts known to secrete at least 20 units/ml of IL-2 in tissue culture when semi-confluent (12). The irradiated tumor cells and genetically modified fibroblasts will be placed in a final volume of 0.2 ml normal saline for immunization.

9) Dose Adjustments

At least two subcutaneous immunizations will be administered, two weeks apart, with irradiated tumor cells and autologous fibroblasts genetically modified to secrete IL-2. If no toxicity is observed, subsequent booster immunizations may be administered periodically (at least one week apart) to optimize the anti-tumor immune response.

J) Treatment of Potential Toxicity

Toxic side effects are not expected to result from these immunizations. However, potential side effects of these immunizations are treatable in the following manner:

If massive tumor cell lysis results, any resulting uric acid nephropathy, adult respiratory distress syndrome, disseminated intravascular coagulation or hyperkalemia will be treated using standard methods.

Local toxicity at the sites of immunization will be treated with either topical steroids and/or surgical excision of the injection site as deemed appropriate.

Hypersensitivity reactions such as chills, fever and/or rash will be treated symptomatically with antipyretics and antihistamines. Patients should not be treated prophylactically. Should arthralgias, lymphadenopathy or renal dysfunction occur, treatment with corticosteroids and/or antihistamines will be instituted. Anaphylaxis will be treated by standard means such as administration of epinephrine, fluids, and steroids.

EXAMPLE II

A. Retroviral IL-2 Gene Transfer and Expression in Fibroblasts

Retroviral vectors were employed to transfer and express IL-2 and neomycin phosphotransferase genes in murine and primary human fibroblasts. The retroviral vector DC/TKIL2 produced by Gilboa and co-workers (Gansbacher, et al., J. Exp. Med. 172:1217–1223, 1990, which is incorporated herein by reference) was utilized to transduce murine fibroblasts for application in an animal tumor model (see Section B below). Human fibroblasts were transduced with the retroviral vector LXSN-RI-IL2 (SEQ ID NO:1). Schematic diagrams of the structure of these retroviral vectors are provided in FIG. 1. A more complete description of the LXSN-RI-IL2 vector, including its nucleotide sequence, is provided in Example III and in Tables 2, 3, 4, 5 and 6 (SEQ ID NO:1).

Figure 2:
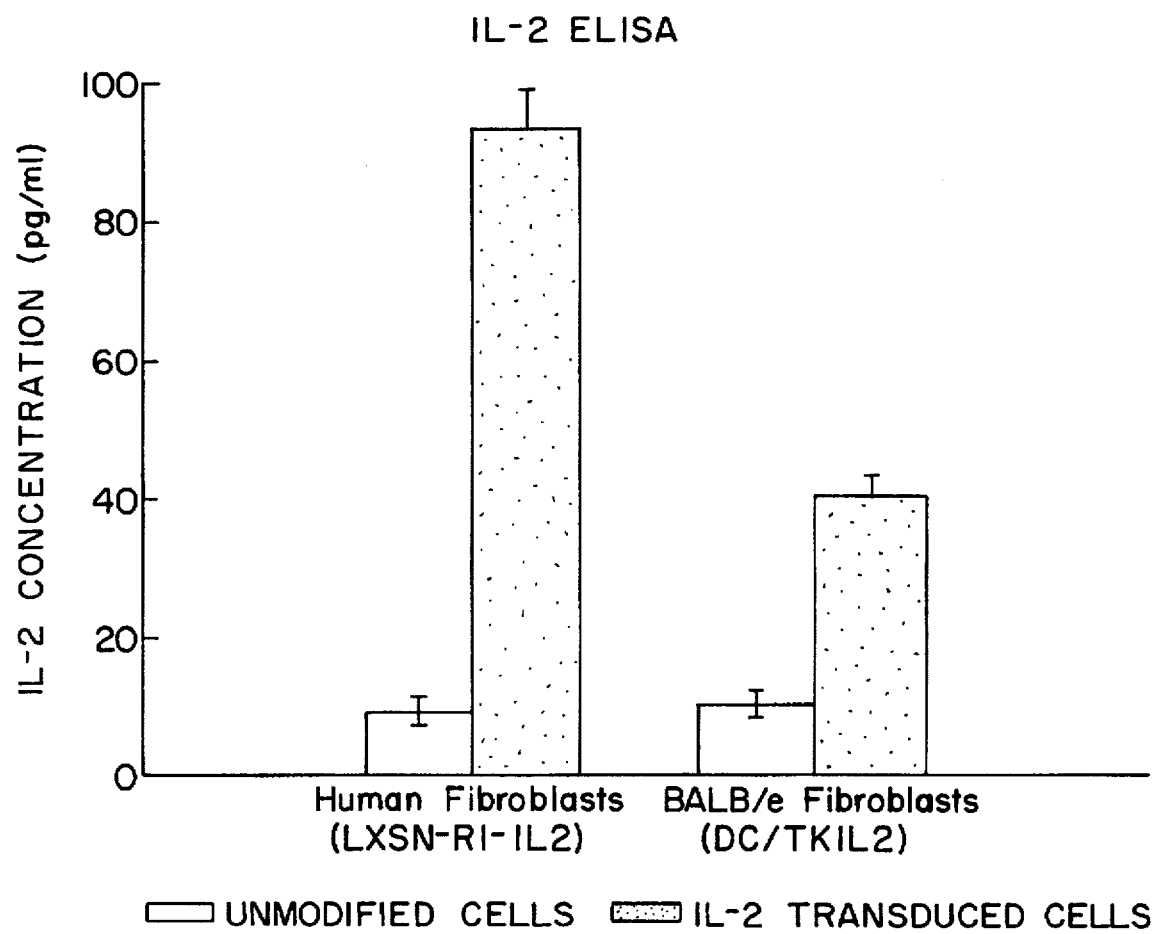
FIG. 2 shows a mean IL-2 concentration of triplicate supernatant samples measured by ELISA. Supernatants were harvested from overnight cultures of approximately $1.5 \times 10^6$ semi-confluent fibroblasts.

Following infection with the described vectors and selection for 2–3 weeks in growth media containing the neomycin analogue G418, Balb/c and human embryonic fibroblast culture supernatants were harvested and tested for IL-2 by an enzyme-linked immunosorbent assay (ELISA). FIG. 2 depicts the levels of IL-2 secreted by the transduced fibroblasts.

These results can be confirmed using negative control fibroblasts infected with an N2-derived retroviral vector expressing an irrelevant gene such as luciferase or β-galactosidase and studies with adult human fibroblasts.

Figure 3:
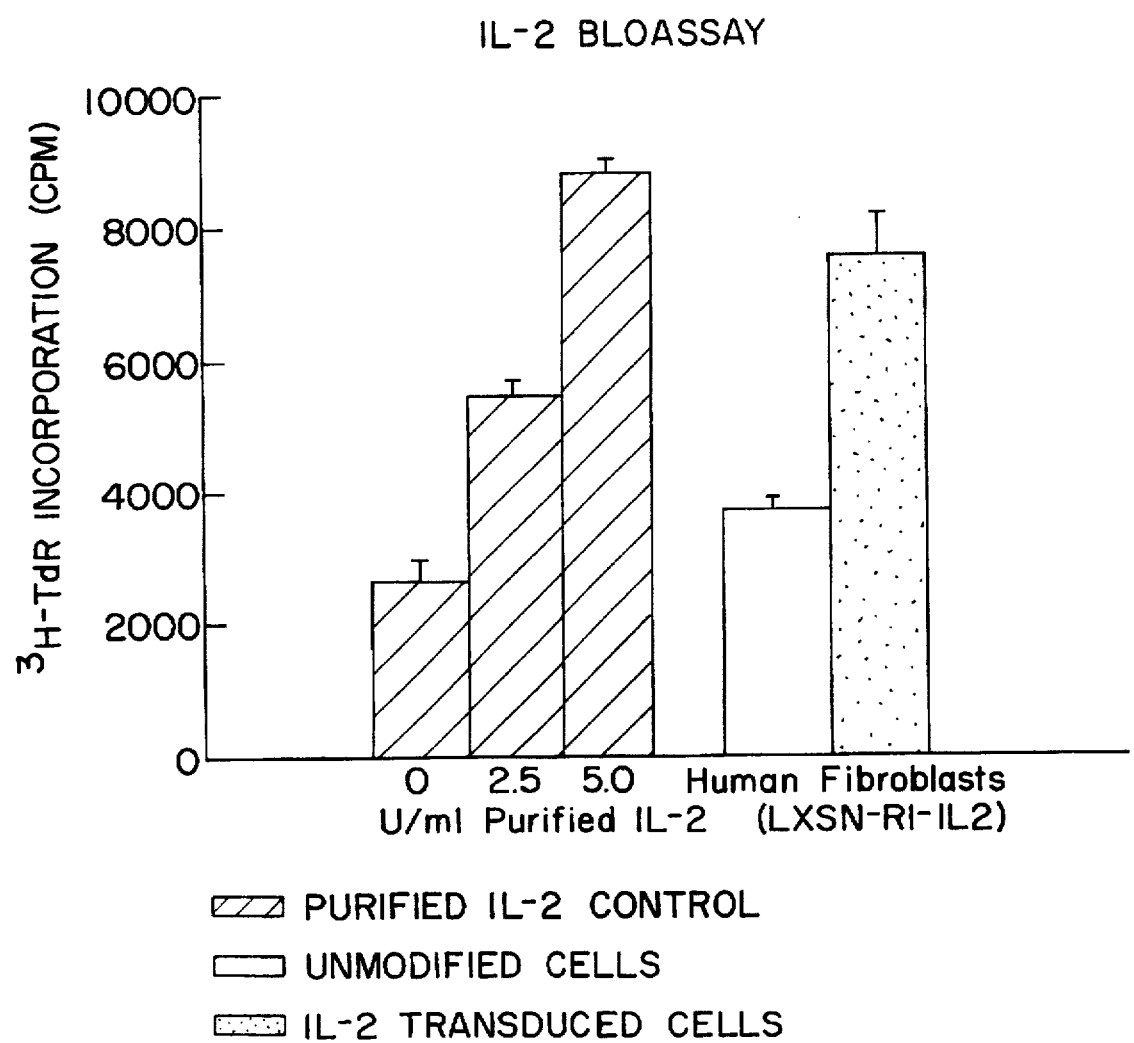
FIG. 3 shows biological activity of the IL-2 secreted by the transduced fibroblasts was demonstrated by measuring mean $^3$H-TdR incorporation of an IL-2 dependent T-cell line incubated with triplicate samples of supernatants. Supernatants were harvested from overnight cultures of approximately $1.5 \times 10^6$ semi-confluent fibroblasts.

Biological activity of the IL-2 expressed by the transduced human fibroblasts was confirmed by a cell proliferation bioassay employing an IL-2 dependent T cell line. In this assay, supernatant from the transduced fibroblasts and control unmodified fibroblasts were incubated with the IL-2 dependent T cell line CTLL-2. Incorporation of $^3$H-thymidine was measured as an indicator of cell proliferation and IL-2 activity (FIG. 3).

B. Efficacy of Transduced Fibroblasts in an Animal Tumor Model

Figure 4:
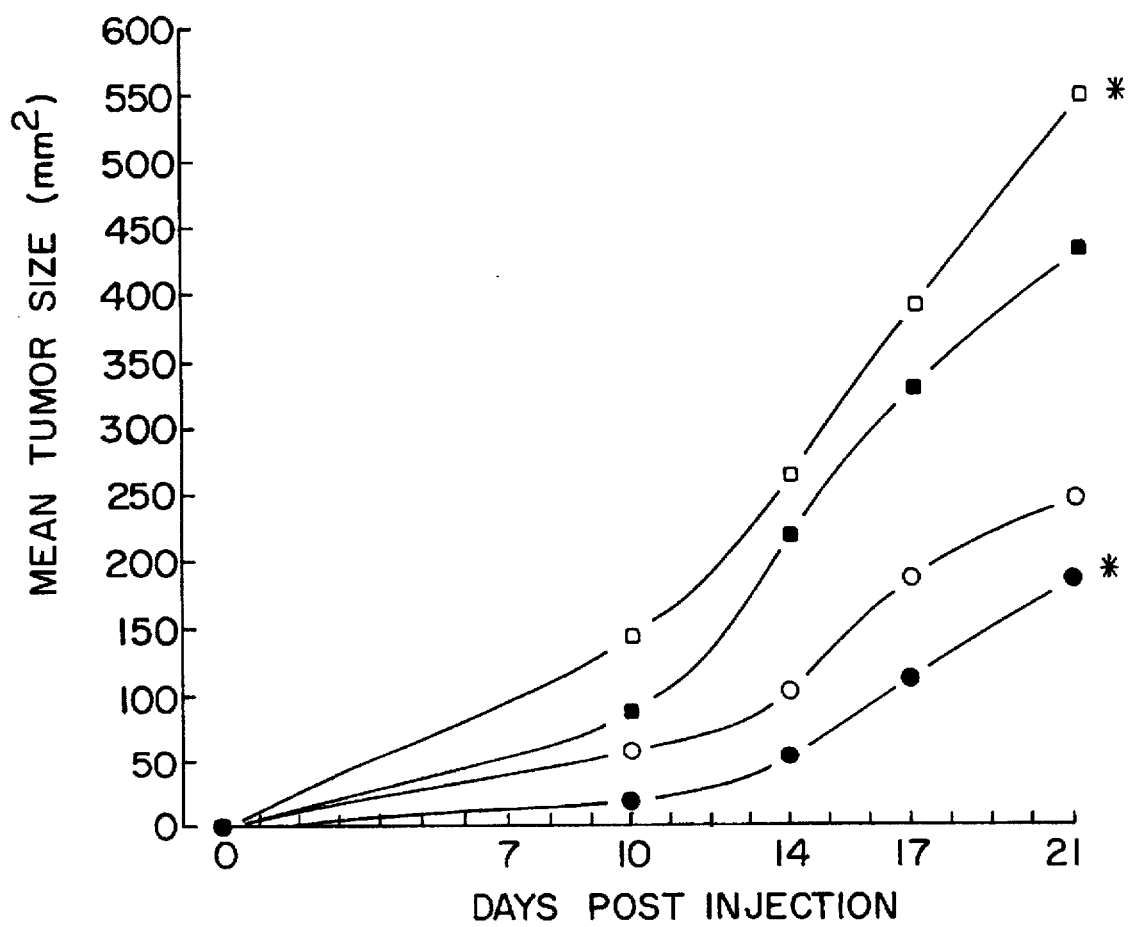
FIG. 4 shows comparisons between animals injected with $10^5$ CT26 tumor cells alone (□); $10^5$ CT26 tumor cells and $2 \times 10^6$ unmodified BALB/C fibroblasts (■); $10^5$ CT26 tumor cells and $2 \times 10^6$ IL-2 transduced BALB/C fibroblasts (●); and $10^5$ CT26 tumor cells and $1 \times 10^6$ transduced BALB/C fibroblasts (○). Tumor measurements are the mean products of the cross-sectional diameter of the tumors from four animals in each treatment group. The (*) indicates statistically significant difference (P<0.05) in tumor growth curves.
Figure 5:
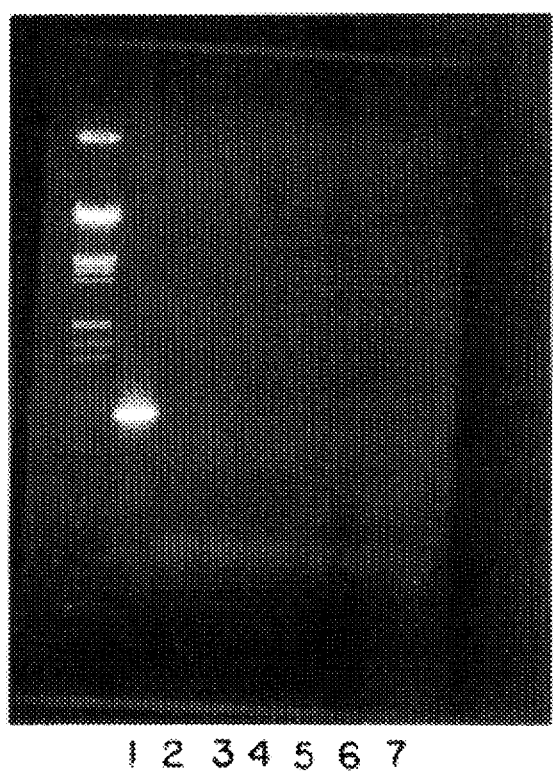
FIG. 5 shows PCR analysis of neomycin phosphotransferase DNA sequences. Lane 1—positive control pLXSN-RI-IL2. Lanes 2 through 4 tests genomic DNA; Lanes 5 and 6 ovary genomic DNA; Lane 7 negative control, no DNA. Identical results were obtained with liver, spleen and lung genomic DNA (data not shown).

The efficacy of fibroblasts genetically modified to secrete IL-2 was tested in an animal model of colorectal carcinoma. In these studies, the Balb/c CT26 tumor cell line was injected subcutaneously with Balb/c fibroblasts transduced to express IL-2. Control groups included animals injected with 1) a mixture of CT26 tumor cells and unmodified fibroblasts; 2) CT26 tumor cells without fibroblasts and 3) transduced fibroblasts alone. No tumors were detected in ⅜ animals treated with transduced fibroblasts and CT26 cells. In contrast, all untreated control animals (8/8) injected with CT26 tumor cells developed palpable tumors. No tumors were detected in the animals inoculated with transduced fibroblasts without CT26 tumor cells. The mean CT26 tumor size in Balb/c mice injected with the IL-2 secreting fibroblasts was considerably smaller compared to the control groups (FIG. 4). A multivariate non-parametric statistical procedure (Koziol, et al., Biometries 37:383–390, 1981 and Koziol, et al., Computer Prog. Biomed. 19:69–74, 1984, which is incorporated herein by reference) was utilized to evaluate differences in tumor growth among the treatment groups. The tumor growth curves for the four treatment groups presented in FIG. 4 were significantly different (p=0.048). Subsequent comparisons between treatment groups revealed a significant difference (p<0.05) in tumor growth between animals injected with CT26 tumor cells alone and animals treated with 2×10⁶ transduced fibroblasts and CT26 tumor cells (FIG. 4).

EXAMPLE III

A. Project Overview

Lymphokine gene therapy of cancer will be evaluated in cancer patients who have failed conventional therapy. An N2-derived vector containing the neomycin phosphotransferase gene will be used. This vector has been employed by a number of investigators for in vitro and in vivo studies including recently approved investigations with human subjects (Rosenberg et al., N. Eng. J. Med., 323:570–578, 1990). The lymphokine vectors used in this investigation will be generated from the N2-derived vector, LXSN, developed and described by Miller et al., Mol. Cell Biol. 6:2895, 1986 and Miller et al., BioTechniques 7:980, 1989, which are incorporated herein by reference. The vector LXSN-RI-IL2 contains human IL-2 cDNA under the control of the retroviral 5' LTR promoter and the neomycin phosphotransferase gene under the control of the SV40 promoter (see FIG. 1). The normal human IL-2 leader sequence has been replaced with a chimeric sequence containing rat insulin and human IL-2 leader sequences (see Tables 2, 3, 4, 5 and 6 (SEQ ID NO:1)). This chimeric leader sequence enhances IL-2 gene expression.

To construct the LXSN-RI-IL2 vector, the bacterial plasmid pBC12/CMV/IL2 (Cullen, B. R., DNA 7:645–650, 1988, which is incorporated herein by reference) containing the full-length IL-2 cDNA and chimeric leader sequence was digested with HindIII and the ends were blunted using Klenow polymerase. IL-2 cDNA was subsequently released from the plasmid by digestion with BamHI. The IL-2 fragment was purified by electrophoresis in a 1% agarose gel and the appropriate band was extracted utilizing a glass powder method. Briefly, the gel slice was dissolved in 4M NaI at 55°. After cooling to room temperature, 4 µl of oxidized silica solution (BIO-101, La Jolla, Calif.) was added to adsorb the DNA. The silica was then washed with a cold solution of 50% ethanol containing 0.1M NaCl in TE buffer. The DNA was eluted from the silica by heating at 55° in distilled H₂O. The purified IL-2 cDNA was then directionally ligated into the HpaI-BamHI cloning sites of the pLXSN vector. A more complete description of the pLXSN-RI-IL2 vector and its partial nucleotide sequence are provided in Tables 2, 3, 4, 5 and 6 (SEQ ID NO:1).

TABLE 2

| | Description of the LXSN-RI-IL2 from position 1 to 6365 |
|---|---|
| Bases | Description |
| 1–589 | Moloney murine sarcoma virus 5' LTR |
| 659–1458 | The sequence of the extended packaging signal |
| 1469–2151 | IL-2 cDNA with chimeric leader sequence |
| 1469–1718 | IL-2 chimeric leader sequence |
| 1647–1718 | coding region of the signal peptide |
| 1719–2151 | Mature IL-2 coding sequence |
| 2158–2159 | Mo mu sarcoma virus end/SV 40 start |
| 2159–2503 | Simian virus 40 early promoter |
| 2521–2522 | Simian virus DNA end/Tn5 DNA start |
| 2557–3351 | Neomycin phosphotransferase |
| 3370–3371 | Tn5 DNA end/Moloney murine leukemia virus start |
| 3411–4004 | Moloney murine leukemia virus 3' LTR |
| 4073–4074 | Moloney murine leukemia DNA end/pBR322 DNA start |
| 4074–6365 | Plasmid backbone |

TABLE 3

| Enzyme | (# Cuts) | Position(s) |
|---|---|---|
| Aat1 | (2) | 1961, 2481 |
| Aat2 | (2) | 811, 6295 |
| Acc1 | (1) | 4252 |
| Acc2 | (19) | 392, 394, 445, 969, 971, 1193, 2751, 3052, 3084, 3807, 3809, 4081, 4083. 4186, 4527, 5108, 5438, 5931, 6263 |
| Acy1 | (5) | 808, 2685, 3860, 5910, 6292 |
| Afl1 | (13) | 260, 273, 328, 626, 756, 1277, 3201, 3676, 3689, 3744, 4041, 5511, 5733 |
| Afl2 | (4) | 34, 1064, 1955, 3446 |
| Afl3 | (2) | 1592, 4480 |
| Aha1 | (20) | 161, 237, 473, 474, 602, 644, 789, 2689, 2849, 3578, 3653, 3888, 3889, 4017, 4059, 4126, 4161, 4860, 5556, 5907 |
| Aha2 | (5) | 808, 2685, 3860, 5910, 6292 |
| Aha3 | (3) | 5239, 5258, 5950 |
| Alu1 | (33) | 29, 33, 119, 190, 411, 654, 734, 742, 1470, 1486, 1751, 1935, 2003, 2446, 2500, 2791, 3249, 3441, 3445, 3532, 3607, 3826, 4069, 4122, 4141, 4422, 4648, 4738, 4784, 5041, 5562, 5662, 5725 |
| Alw1 | (20) | 1110, 1414, 1665, 2018, 2147, 2160, 2529, 2553, 2864, 2929, 3110, 4027, 5041, 5127, 5129, 5225, 5226, 5689, 6006, 6010 |
| AlwN1 | (4) | 231, 3572, 3647, 4896 |
| Aoc1 | (2) | 847, 1076 |
| Aoc2 | (19) | 323, 413, 426, 597, 1583, 1721, 2631, 2724, 2798, 2988, 3050, 3739, 3828, 3841, 4012, 4300, 4798, 5959, 6044 |
| Aos1 | (2) | 2787, 5595 |
| ApaL1 | (4) | 1717, 4296, 4794, 6040 |
| Apy1 | (22) | 315, 623, 801, 814, 1227, 1252, 1275, 1295, 1325, 1526, 1536, 1558, 1630, 2196, 2251, 2268, 3072, 3731, 4038, 4508, 4629, 4642 |
| Aqu1 | (6) | 241, 472, 1998, 3821, 3854, 3887 |
| Ase1 | (2) | 1801, 5545 |
| Asp700 | (1) | 5972 |
| Asp718 | (2) | 476, 3891 |
| AspA1 | (1) | 1145 |
| Asu1 | (29) | 169, 200, 245, 260, 273, 328, 626, 756, 826, 839, 1043, 1254, 1277, 1532, 1649, 3201, 3541, 3586, 3616, 3661, 3676, 3689, 3744, 4041, 5415, 5494, 5511, 5733, 6349 |
| Ava1 | (6) | 241, 472, 1998, 3821, 3854, 3887 |
| Ava2 | (13) | 260, 273, 328, 626, 756, 1277, 3201, 3676, 3689, 3744, 4041, 5511, 5733 |
| Ava3 | (2) | 2232, 2304 |
| Avr2 | (2) | 1962, 2482 |
| Bal1 | (3) | 658, 1169, 2767 |
| BamH1 | (1) | 2152 |
| Ban1 | (9) | 318, 476, 1200. 2684, 2719, 3734, 3859, 3891, 5321 |
| Ban2 | (8) | 413, 426, 597, 1583, 3050, 3828, 3841, 4012 |
| Bbe1 | (2) | 2688, 3863 |
| Bbv1 | (22) | 969, 997, 1738, 2493, 2632, 2758, 2800, 2816, 2909, 3321, 4060, 4131, 4228, 4372, 4390, 4809, 4899, 4902, 5108, 5411, 5600, 5802 |
| Bcl1 | (1) | 2526 |
| Bgl1 | (2) | 2435, 5493 |
| Bsp1286I | (19) | 323, 413, 426, 597, 1583, 1721, 2631, 2724, 2798, 2988, 3050, 3739, 3828, 3841, 4012, 4300, 4798, 5959, 6044 |
| BspH1 | (3) | 5200, 6208, 6313 |
| BspM1 | (4) | 1501, 2500, 2572, 2953 |
| BssH2 | (4) | 392, 443, 3082, 3807 |
| BstE2 | (1) | 1145 |
| BstN1 | (22) | 315, 623, 801, 814, 1227, 1252, 1275, 1295, 1325, 1526, 1536, 1558, 1630, 2196, 2251, 2268, 3072, 3731, 4038, 4508, 4629, 4642 |
| BstU1 | (19) | 392, 394, 445, 969, 971, 1193, 2751, 3052, 3084, 3807, 3809, 4081, 4083, 4186, 4527, 5108, 5438, 5931, 6263 |
| BstX1 | (1) | 2060 |
| BstY1 | (11) | 2010, 2152, 2521, 2856, 3102, 5121, 5132, 5218, 5230, 5998, 6015 |
| Bsu36I | (2) | 847, 1076 |
| Ccr1 | (1) | 1998 |
| Cfo1 | (31) | 394, 396, 445, 447, 714, 971, 2679, 2687, 2751, 2788, 3054, 3084, 3086, 3314, 3809, 3811, 3862, 4083, 4186, 4216, 4357, 4390, 4660, 4727, 4827, 5001, 5110, 5503, 5596, 5933, 6265 |
| Cfr1 | (9) | 656, 790, 1167, 1188, 2591, 2765, 3156, 3183, 5761 |
| Cfr10I | (3) | 3004, 3185, 5453 |
| Cfr13X | (29) | 169, 200, 245, 260, 273, 328, 626, 756, 826, 839, 1043, 1254, 1277, 1532, 1649, 3201, 3541, 3586, 3616, 3661, 3676, 3689, 3744, 4041, 5415, 5494, 5511, 5733, 6349 |
| Cvn1 | (2) | 847, 1076 |
| Dde1 | (23) | 75, 165, 191, 282, 553, 847, 1076, 1348, 1692, 2442, 3348, 3487, 3582, 3657, 3698, 3879, 3967, 4290, 4755, 5164, 5330, 5870, 6296 |
| Dpn1 | (30) | 95, 1104, 1236, 1421, 1659, 2012, 2154, 2523, 2528, 2547, |

TABLE 3-continued

| Enzyme | (# Cuts) | Position(s) |
|---|---|---|
| | | 2858, 2936, 3017, 3026, 3104, 3507, 4021, 5048, 5123, 5134, 5142, 5220, 5232, 5337, 5678, 5696, 5742, 6000, 6017, 6053 |
| Dra1 | (3) | 5239, 5258, 5950 |
| Dra2 | (4) | 328, 1277, 3744, 6349 |
| Eae1 | (9) | 656, 790, 1167, 1108, 2591, 2765, 3156, 3183, 5761 |
| Eag1 | (2) | 790, 2591 |
| Eco47I | (13) | 260, 273, 328, 626, 756, 1277, 3201, 3676, 3689, 3744, 4041, 5511, 5733 |
| Eco52I | (2) | 790, 2591 |
| Eco81X | (2) | 847, 1076 |
| EcoN1 | (2) | 850, 1450 |
| Eco0109I | (4) | 328, 1277, 3744, 6349 |
| EcoR1 | (1) | 1460 |
| EcoR1* | (14) | 938, 1037, 1460, 1798, 1805, 1928, 2064, 2121, 2236, 2308, 2400, 5240, 5546, 5801 |
| EcoR2 | (22) | 313, 621, 799, 812, 1225, 1250, 1273, 1293, 1323, 1524, 1534, 1556, 1628, 2194, 2249, 2266, 3070, 3729, 4036, 4506, 4627, 4640 |
| EcoR5 | (4) | 137, 213, 3554, 3629 |
| EcoT22I | (2) | 2232, 2304 |
| Fdi2 | (2) | 2787, 5595 |
| Fnu4H1 | (41) | 793, 967, 983, 986, 1191, 1752, 2430, 2507, 2594, 2646, 2657, 2747, 2752, 2789, 2830, 2917, 2920, 2923, 3159, 3255, 3296, 3310, 4074, 4120, 4217, 4270, 4386, 4404, 4407, 4525, 4680, 4823, 4888, 4891, 5097, 5425, 5614, 5764, 5791, 5886, 6115 |
| FnuD2 | (9) | 392, 394, 445, 969, 971, 1193, 2751, 3052, 3084, 3807, 3809, 4081, 4083, 4186, 4527, 5108, 5438, 5931, 6263 |
| Fok1 | (13) | 498, 1198, 1358, 1679, 2333, 2552, 3009, 3034, 3912, 4168, 5339, 5520, 5807 |
| Fsp1 | (2) | 2787, 5595 |
| Hae2 | (4) | 2688, 3863, 4358, 4728 |
| Hae3 | (35) | 171, 202, 247, 658, 792, 828, 840, 1045, 1169, 1190, 1255, 1534, 1650, 1866, 1961, 2423, 2429, 2438, 2481, 2593, 2767, 3158, 3185, 3543, 3588, 3618, 3663, 4495, 4506, 4524, 4958, 5416, 5496, 5763, 6350 |
| Hap2 | (30) | 161, 237, 473, 601, 643, 789, 2590, 2667, 2689, 2717, 2848, 2938, 3005, 3186, 3578, 3653, 3888, 4016, 4058, 4126, 4160, 4687, 4834, 4860, 5050, 5454, 5488, 5555, 5665, 5907 |
| Hga1 | (8) | 455, 707, 960, 1580, 4175, 4591, 5169, 5899 |
| HgiA1 | (9) | 413, 1721, 2798, 2988, 3828, 4300, 4798, 5959, 6044 |
| Hha1 | (31) | 394, 396, 445, 447, 714, 971, 2679, 2687, 2751, 2788, 3054, 3084, 3086, 3314, 3809, 3811, 3862, 4083, 4186, 4216, 4357, 4390, 4660, 4727, 4827, 5001, 5110, 5503, 5596, 5933, 6265 |
| HinP1 | (31) | 392, 394, 443, 445, 712, 969, 2677, 2685, 2749, 2786, 3052, 3082, 3084, 3312, 3807, 3809, 3860, 4081, 4184, 4214, 4355, 4388, 4658, 4725, 4825, 4999, 5108, 5501, 5594, 5931, 6263 |
| Hinc2 | (1) | 5914 |
| Hind2 | (1) | 5914 |
| Hind3 | (1) | 2498 |
| Hinf1 | (14) | 298, 517, 857, 868, 1553, 1814, 3170, 3304, 3356, 3881, 4380, 4455, 4851, 5368 |
| Hpa2 | (30) | 161, 237, 473, 601, 643, 789, 2590, 2667, 2689, 2717, 2848, 2938, 3005, 3186, 3578, 3653, 3888, 4016, 4058, 4126, 4160, 4687, 4834, 4860, 5050, 5454, 5488, 5555, 5665, 5907 |
| Hph1 | (11) | 1214, 1240, 1817, 2863, 4102, 4111, 5216, 5443, 5859, 6065, 6100 |
| Kpn1 | (2) | 480, 3895 |
| Mae1 | (15) | 30, 293, 689, 727, 739, 1452, 1606, 1893, 1963, 2483, 3442, 3709, 4975, 5228, 5563 |
| Mae2 | (11) | 808, 1139, 1180, 1987, 2801, 2988, 4233, 5183, 5599, 5972, 6292 |
| Mae3 | (20) | 38, 1052, 1080, 1145, 1289, 1478, 1706, 2805, 3111, 3450, 4134, 4229, 4836, 4899, 5015, 5298, 5629, 5687, 5840, 6028 |
| Mbo1 | (30) | 93, 1102, 1234, 1419, 1657, 2010, 2152, 2521, 2526, 2545, 2856, 2934, 3015, 3024, 3102, 3505, 4019, 5046, 5121, 5132, 5140, 5218, 5230, 5335, 5676, 5694, 5740, 5998, 6015, 6051 |
| Mbo2 | (17) | 444, 1145, 1356, 1575, 1617, 1908, 1911, 3046, 3256, 3336, 4351, 5142, 5213, 5968, 6046, 6155, 6351 |
| Mn11 | (54) | 291, 444, 508, 534, 560, 639, 841, 939, 1227, 1330, 1363, 1369, 1372, 1378, 1408, 1411, 1426, 1433, 1449, 1559, 1620, 1909, 1921, 2412, 2418, 2443, 2449, 2455, 2458, 2470, 2508, 2535, 2599, 2735, 3092, 3286, 3707, 3859, 3878, 3923, 3948, 3974, 4054, 4087, 4117, 4379, 4587, 4662, 4911, 5311, 5392, 5540, 5746, 6339 |
| Mse1 | (22) | 35, 1065, 1177, 1207, 1231, 1801, 1843, 1956, 1971, 2124, 2139, 3447, 4261, 5186, 5238, 5243, 5257, 5310, 5545, 5584, 5949, 6321 |
| Msp1 | (30) | 161, 237, 473, 601, 643, 789, 2590, 2667, 2689, 2717, 2848, 2938, 3005, 3186, 3578, 3653, 3888, 4016, 4058, 4126, 4160, 4687, 4834, 4860, 5050, 5454, 5488, 5555, 5665, 5907 |

TABLE 3-continued

| Enzyme | (# Cuts) | Position(s) |
| --- | --- | --- |
| Mst1 | (2) | 2787, 5595 |
| Mst2 | (2) | 847, 1076 |
| Mva1 | (22) | 315, 623, 801, 814, 1227, 1252, 1275, 1295, 1325, 1526, 1536, 1558, 1630, 2196, 2251, 2268, 3072, 3731, 4038, 4508, 4629, 4642 |
| Nae1 | (1) | 3187 |
| Nar1 | (2) | 2685, 3860 |
| Nci1 | (20) | 161, 237, 473, 474, 602, 644, 789, 2689, 2849, 3578, 3653, 3888, 3889, 4017, 4059, 4126, 4161, 4860, 5556, 5907 |
| Nco1 | (2) | 2389, 3117 |
| Nde1 | (1) | 4303 |
| Nde2 | (30) | 93, 1102, 1234, 1419, 1657, 2010, 2152, 2521, 2526, 2545, 2856, 2934, 3015, 3024, 3102, 3505, 4019, 5046, 5121, 5132, 5140, 5218, 5230, 5335, 5676, 5694, 5740, 5998, 6015, 6051 |
| Nhe1 | (3) | 29, 1605, 3441 |
| Nla3 | (26) | 61, 1263, 1596, 1649, 1835, 1856, 2030, 2230, 2302, 2393, 2559, 2904, 3090, 3121, 3147, 3473, 4119, 4224, 4484, 5204, 5695, 5705, 5783, 5819, 6212, 6317 |
| Nla4 | (28) | 153, 246, 262, 320, 478, 627, 758, 827, 959, 1202, 1279, 2154, 2200, 2272, 2686, 2721, 3678, 3736, 3861, 3893, 4042, 4512, 4551, 5323, 5417, 5458, 5669, 6259 |
| Nsi1 | (2) | 2232, 2304 |
| Nsp(7524)1 | (8) | 1596, 1835, 1856, 2230, 2302, 3090, 4119, 4484 |
| Nsp(7524)2 | (19) | 323, 413, 426, 597, 1583, 1721, 2631, 2724, 2798, 2988, 3050, 3739, 3828, 3841, 4012, 4300, 4798, 5959, 6044 |
| NspB2 | (12) | 119, 190, 1751, 2158, 2791, 3532, 3607, 3989, 4192, 4822, 5067, 6008 |
| NspH1 | (8) | 1596, 1835, 1856, 2230, 2302, 3090, 4119, 4484 |
| PaeR7I | (1) | 1998 |
| Pal1 | (35) | 171, 202, 247, 658, 792, 828, 840, 1045, 1169, 1190, 1255, 1534, 1650, 1866, 1961, 2423, 2429, 2438, 2481, 2593, 2767, 3158, 3185, 3543, 3588, 3618, 3663, 4495, 4506, 4524, 4958, 5416, 5496, 5763, 6350 |
| Ple1 | (7) | 865, 1547, 3350, 3889, 4374, 4859, 5362 |
| PpuM1 | (3) | 328, 1277, 3744 |
| Pss1 | (4) | 331, 1280, 3747, 6352 |
| Pst1 | (6) | 987, 1163, 1888, 2511, 2738, 5618 |
| Pvu1 | (1) | 5743 |
| Pvu2 | (6) | 119, 190, 1751, 2791, 3532, 3607 |
| Rsa1 | (10) | 347, 478, 725, 1342, 1519, 1597, 2991, 3893, 4288, 5853 |
| Rer2 | (1) | 3201 |
| Sac1 | (2) | 413, 3828 |
| Sau1 | (2) | 847, 1076 |
| Sau3A1 | (30) | 93, 1102, 1234, 1419, 1657, 2010, 2152, 2521, 2526, 2545, 2856, 2934, 3015, 3024, 3102, 3505, 4019, 5046, 5121, 5132, 5140, 5218, 5230, 5335, 5676, 5694, 5740, 5998, 6015, 6051 |
| Sau96I | (29) | 169, 200, 245, 260, 273, 328, 626, 756, 826, 839, 1043, 1254, 1277, 1532, 1649, 3201, 3541, 3586, 3616, 3661, 3676, 3689, 3744, 4041, 5415, 5494, 5511, 5733, 6349 |
| Sca1 | (1) | 5853 |
| ScrF1 | (42) | 161, 237, 315, 473, 474, 602, 623, 644, 789, 801, 814, 1227, 1252, 1275, 1295, 1325, 1526, 1536, 1558, 1630, 2196, 2251, 2268, 2689, 2849, 3072, 3578, 3653, 3731, 3888, 3889, 4017, 4038, 4059, 4126, 4161, 4508, 4629, 4642, 4860, 5556, 5907 |
| Sdu1 | (19) | 323, 413, 426, 597, 1583, 1721, 2631, 2724, 2798, 2988, 3050, 3739, 3828, 3841, 4012, 4300, 4798, 5959, 6044 |
| Sec1 | (38) | 159, 235, 314, 324, 472, 536, 621, 622, 760, 799, 800, 812, 813, 1225, 1294, 1303, 1323, 1324, 1525, 1557, 1962, 2194, 2266, 2389, 2424, 2433, 2482, 2848, 3117, 3576, 3651, 3730, 3740, 3887, 3950, 4036, 4037, 4640 |
| SfaN1 | (23) | 258, 520, 997, 1657, 2107, 2239, 2311, 2643, 2898, 2984, 3048, 3114, 3323, 3674, 3934, 4146, 4281, 4317, 4357, 4577, 5629, 5820, 6069 |
| Sfi1 | (1) | 2435 |
| Sma1 | (2) | 474, 3889 |
| Spe1 | (1) | 726 |
| Sph1 | (4) | 1835, 2230, 2302, 3090 |
| Ssp1 | (1) | 6177 |
| Sst1 | (2) | 413, 3828 |
| Stu1 | (2) | 1961, 2481 |
| Sty1 | (9) | 324, 536, 1303, 1962, 2389, 2482, 3117, 3740, 3950 |
| Taq1 | (15) | 860, 1096, 1407, 1418, 1660, 1999, 2514, 2798, 2954, 2978, 3014, 3176, 3367, 4580, 6024 |
| Tha1 | (19) | 392, 394, 445, 969, 971, 1193, 2751, 3052, 3084, 3807, 3809, 4081, 4083, 4186, 4527, 5108, 5438, 5931, 6263 |
| Tth111I | (6) | 465, 877, 1275, 2803, 3880, 4227 |
| Xba1 | (2) | 1892, 3708 |
| Xho1 | (1) | 1998 |

TABLE 3-continued

| Enzyme | (# Cuts) | Position(s) |
|---|---|---|
| Xho2 | (11) | 2010, 2152, 2521, 2856, 3102, 5121, 5132, 5218, 5230, 5998, 6015 |
| Xma1 | (2) | 472, 3887 |
| Xma3 | (2) | 790, 2591 |
| Xmn1 | (1) | 5972 |
| Xor2 | (1) | 5743 |

TABLE 4 enzymes which do not cut LXSNRIIL2:

| | | | | | |
|---|---|---|---|---|---|
| Acc3 | Bgl2 | Cla1 | Hpa1 | Nru1 | SnaB1 |
| Apa1 | Bsm1 | Dra3 | Mlu1 | PflM1 | Spl1 |
| Asu2 | BspM2 | Eco47III | Mro1 | Sac2 | Sst2 |
| Ban3 | BstB1 | Esp1 | Not1 | Sal1 | |

TABLE 5

From 1 to 6365. Numbered from position 1.

```
LXSNRILL2 ------1000+------2000+------3000+------4000+------5000+------6000+
Mo-MuSV 5' long ter  -------->
-(Split)                      >
1 to 683 of RIII.2                    ========>
neomycin phosphotra                           -------->
Mo-MuLV 3' long ter
signal                1                     1
```

| Enzyme | Sites |
|---|---|
| Aat1 | ------------------------1------1---------------------------------+---------- |
| Aat2 | ------------1-+----------------------------------------+---------------+--1- |
| Acc1 | ---------------+---------------+---------------+---------------+----------- |
| Acc2 | --21--2-1-+-----------+---------1--+2-------2-+21-----------1+-------1+---1- |
| Acy1 | ---------1-+---------------+---------1-+-----1-+---------------+---------1- |
| Afl1 | ---3--11-+-------1-+-------------+--------1--21-+1----------1-+---------1-- |
| Afl2 | 1---------+1--------------+-------1-+---------------+--------1--+---------- |
| Afl3 | ------------+------------1--+---------------+---------1-+---------------+-- |
| Aha1 | -11--2-2-1-+-----------+--------11--+------11--2112--------1-+----------1-- |
| Aha2 | -----------1-+---------------+--------1-+---------1-+---------------+---1-- |
| Aha3 | ---------------+---------------+---------------+-------2---+------1+------- |
| Alu1 | 211--1-12-+----2-1--2--2---1-+--1112-1-+12-1--12-1+---111-+---- |
| Alw1 | ------1--1--1-+--+12---2---2+-1--------1-+---------2-+---------1--2---- |
| AlwN1 | ---1-----------+---------------+-------11-------+------1-+-----------+---- |
| Aoc1 | ---------1+1---+---------------+---------------+-1+---------------+------- |
| Aoc2 | -111-1----+-1-1-+----111-11---+---12-1--1---+---1--+---11--+------- |
| Aos1 | ---------------+---------------+---------1-+--------1-+-----------1+------ |
| ApaLi | -----------1-+-----------+---1-+---------------+---------1-+---------1+--- |
| Apy1 | ---1--1-2-+-23--31---+--3------+1----1-+1--1-2-+------1+------- |
| Aqu1 | -1--1-+-------1-+---------------+---21+---------------+---------+---1----- |
| Ase1 | ---------------+---------1-+---------------+---------------+------1-+----- |
| Asp700 | ---------------+---------------+---------------+---------------+---------1- |

TABLE 5-continued

From 1 to 6365. Numbered from position 1.

```
         LXSNRIIL2  ----------1000+---------2000+---------3000+---------4000+---------5000+---------6000+
Mo-MuSV 5' long ter  ---------->
- (Split)                          >
1 to 683 of RIIL2                  ==========>
neomycin phosphotra                             ---------->
Mo-MuLV 3' long ter                                                                              ---------->
signal                             1                      1

Asp718       ----------+---------+---------+---------+---------+----1----+----------+
AspA1        ----------+--+1-----+---------+---------+---------+---------+
Asu1         --33---112-+1--11---11-----+---------+--1--241--+1---------+---12--1---+----1
Ava1         ---1--1---+---------+---------+---------+----21---+---------+
Ava2         ---3--11--+--+--1---+---------+---1--+---------+--1--21---+1--------+----1--1-+
Ava3         ----------+--+------+----11---+---------+---------+---------+
Avr2         ----------+---------+-----1---+---------+---------+---------+
Ball         ----1--+1-+---------+---------+---1-----+---------+---------+
BamH1        ----------+---------+---------+-----1---+---------+---------+
Bbe1         ----------+---------+---------+----1----+---------+---------+
Bbv1         ----------+--2------+-----1--+-+--1121+--1-------+111-2---12+1--1--1-1-+
Bcl1         ----------+---------+-----1---+---------+---------+---------+
Bgl1         ----------+---------+---------+---------+---------+----1----+
Bsp1286I     ---111-1--+---------+---1-----+-111-11--+---12-1--+-1---1---+-----11--+
BspH1        ----------+---------+---------+---------+---------+----+1---+-1----1-1
BspM1        ----21----+--2--1---+---1---+-+--11---1-+---------+---------+---1-----+---1------+
BssH2        ----11----+---------+----11--+-+--+1----+---------+---------+
BstE2        ----------+--+--1---+---------+---------+---------+---------+
BstN1        ---1--1-2-+--23--31-+---+--3---+-----1---+--1+1---1+-2-------+
BstU1        ----21----+--2--1---+---1---+-+--11---1-+-2-+21----+---1----1+---1-----+---1------+
BstX1        ----------+---------+----+1---+---------+---------+---------+
BstY1        ----------+---------+-1--1--1-+1---------+---------+---+112--+2---------+
Bsu36I       ----------+--1+1----+---------+---------+---------+---------+
```

TABLE 5-continued

From 1 to 6365. Numbered from position 1.

```
LXSNRILL2 ------1000+------2000+------3000+------4000+------5000+------6000+------
Mo-MuSV 5' long ter   ------->
- (Split)                    >
1 to 683 of RILL2                    ========>
neomycin phosphotra
Mo-MuLV 3' long ter                                                              ------>
signal                       1                                    1
```

| | |
|---|---|
| Ccr1 | `-------------------+-------------------+-------1---------+-----------------+------------------+-------------------+-------` |
| Cfo1 | `----22--1--1----+--1----------------+---211-+3--1------+---3-+11111--11----11--1-+--1-` |
| Cfr1 | `---------1-1-+-11----+-----------------+-1-1--+2-------+--------------+------1--------+----1-+` |
| Cfr10I | `-------------------+-------------------+---1-1----------+-----------------+-----1----------+-------------------+-` |
| Cfr13I | `--33----112-+1-11-11---+-------1-------+--1--241-+1----+-12--1-+--1` |
| Cvn1 | `------------1-+1----+-----------------+-------1-+-------+-----------------+-------------------+-` |
| Dde1 | `1111--1--1+1----+----1---1-----1-+--1-----1---1-+-1111-11---1-+-1--1---1-+--1-+-` |
| Dpn1 | `-1----------+-111-1--1---1-+---3--212---1-+----1-----+---+2221--21--21--` |
| Dra1 | `-------------------+-----------1-+-+------------------+-----------------+-------------------+--1-+` |
| Dra2 | `---1--------------+-----1----+-----------------+-----------------+-------+2-----1-+-` |
| Eae1 | `----------1-1-+11----+--1----1--1----+--1----1-1111-11-+-1--1-+-1-+-` |
| Eag1 | `-------------------+-----------------+-----------------+-----------------+------1-+-` |
| Ecc47I | `-3---11--+----1-+---1----1--1--+-1--+2-1-+-1--1--1-+-` |
| Eco52I | `-----------1-+-+-----------------+-----------------+------21-+1-----------------+-1+` |
| Eco8II | `-------1+1----+-----------------+-----------------+-1-----------------+-1+` |
| EcoN1 | `------1+----+-----1-+-----------------+-----------------+-----------------+-1+` |
| EcoO109I | `---1-----------1-+-----------------+-----------------+-----1-+-----------------+-1+` |
| EcoR1 | `-----------------+-----------------+-----------------+-----------------+-----------------+-1+` |
| EcoR1* | `------11---1--21+111111-+----------+-----1--1-+-1-+-1-1-+` |
| EcoR2 | `-1--1-2--23-31--+--3-----+-----1--1-2---+-1-+-1-1-+` |
| EcoR5 | `-11-----+----------------+-----------------+--11-+----------------+-----1+` |
| EcoT22I | `-------------------+-11-----+-----------------+-----------------+-----------------+-+` |
| Fdi2 | `-------------------+-----------------+-----1-+-----------------+------1-+------1-+` |

TABLE 5-continued

From 1 to 6365. Numbered from position 1.

```
         ----------1000+---------2000+---------3000+---------4000+---------5000+---------6000+----
LXSNRIIL2
Mo-MuSV 5' long ter ------>
- (Split)
1 to 683 of RIIL2          >   ========>
neomycin phosphotra                    -------->
Mo-MuLV 3' long ter                              >
signal             1                  1
```

|  | | | | | | |
|---|---|---|---|---|---|---|
| Fnu4H1 | ----------------------1-3--1----+-----------1---+------1112223+-112------+112-31-1-12+1---1--1-2-1+1--- |
| FnuD2 | ------21-----2-1------------+----------------+---1---+2-----------2+21---------1----1------1+---1--- |
| Fok1 | ---------1---------2--1-1-----+--1-1---1----1---+---11---------1+-----1-----+------1-1----1+------- |
| Fsp1 | ------------+------------------+----------------+---------------+-----------+--------------+------- |
| Hae2 | -----1-----------+-----------+------------------+----------1-----+-----------+--------1-----+------- |
| Hea3 | --3-----1-3-+1112----------1-11+---221-1---11-----+--221-----22---+-----3-----+----1--1-1-1--+---1--- |
| Hap2 | -11--1-2-1-+----------------+------+---112111-1----11-1112---+---1-2-+1--1111--1+--- |
| Hga1 | -----1--1-1-----+--------1---+----------------+---------------+--+1--1-+-1+----1+----- |
| HgiA1 | --------1--------+-------------+-----1-----+--------1--------1+-------1--1+------1------1+------- |
| Hha1 | --22--1--1----+-----------1-----+---211-+3--1-----+-----3-+11111-111--11----11----1+1---1+------- |
| HinP1 | --22--1--1----+-----------------+---211-+3--1-----+-----3-+11111-111--11----11----1+1---1+------- |
| Hinc2 | -----------+------------------+------------+--------1-+----+------1----1+------- |
| Hind2 | -----------+------------------+------------+--------1-+----+------1----1+------- |
| Hind3 | -----------+-----------------+------------+------------+--------1+------- |
| Hinf1 | ----1--1----2+----1-1----1-11----1+-----------1--+---+1-2----------1+-------1-----+-----1-1----1-+------- |
| Hpa2 | -11--1-2-1-+-----------+------+--112111-1----11--1112-+---1-2-+1--1111--1+------- |
| Hph1 | --------+------1-1-----2-----1--+-----1-----+---1---+1----1------1+-----2+------- |
| Kpn1 | -----1-+--------+-----------+-----------+------------+------+------- |
| Mae1 | 1--1---3-+-----------+-----------1-+---------1+------+-------1-----1-1-+------- |
| Mae2 | -----1-+11-----------+-----------------+---1----1--+-----1----+-------1----1+---1--- |
| Mae3 | 1------+21-1-1------+-----1----+------1-+----11-----111--1--2-1-1----+------- |
| Mbo1 | -1----+11-1-1---1-+------3--1121---1-+-----1-+----1----+2221--21-21--+------- |
| Mae1 | 1------+1-3------2-2-2-+------------+------+----1-+---131-2--1+---1 |

TABLE 5-continued

From 1 to 6365. Numbered from position 1.

TABLE 5-continued

From 1 to 6365. Numbered from position 1.

```
              ---------1000+---------2000+---------3000+---------4000+---------5000+---------6000+
LXSNRIIL2
Mo-MuSV 5' long ter  --------->
- (Split)                        >
1 to 683 of RIIL2                 ----------->
neomycin phosphotra                        ========>
Mo-MuLV 3' long ter                                                                      ------->
signal                1

Pst1        ----------------------------1+--------1-1--------------------+-------------1---------------+----
Pvu1        -----------------------------+---------+------------------------+--------------+-----1-----+----
Pvu2        -11-------------------------1-+---------+-----------2-----------+--------------+----------+----
Rsa1        ---11-1----+----11-----+-1-11----+-------1-+--1-+-------------1-+--------------+-----1----1-+--
Rsr2        -------------+----------+--------+-------1-+-----+------1-------+--------------+----------+----
Sac1        ----1--------+----------+--------+---------+-----+---1---------+--------------+----------+----
Sau1        -------1+1---+----------+--------+---------+-----+-------------+--------------+----------+----
Sau3A1      -1-------------+--11-1--+-1-----3--1121----+---1-+------1------+---+2221---21--21---------+----
Sau96I      --33---+112-+-1-11--11--+----------+--241--+1------+----12--1--+-----+----------+----------1
Sca1        -------------+----------+--------+---------+-----+-------------+--------------+----1-+-----+--
ScrF1       -111-2-3-3-+--23--31---+-----3----11--+1---111-2122-1-2-1--+----1----1---------+-----------1---
Sdu1        ---111-1----+----------+---1-1---+----------111-11-----12-1--1-+-----1---------+----------+----
Sec1        --112-112-5-+--14--2---1--2-31----1-+-1----112-112------1-+--------------+-----------------+----
SfaN1       ---1-1----1-------1+--+----1+1111--1-1111-1--1-1+-112---1-+----1-1+-1--+--------1-1--1----1+----
Sfi1        -------------+----------+---1-----+---------+-----+-------------+--------------+----------+----
Sma1        ----1--------+----------+--------+--------1+-----+-------------+--------------+----------+----
Spe1        -------------+----------+--------+---------+-----+-------------+--------------+----------+----
Sph1        ------------+-1----11---+-------+------+-1----+-------------+--------------+----------+----
Ssp1        -------------+----------+--------+---------+-----+-------------+--------------+-----1----+----
Sst1        ----1--------+----------+--------+---------+-----+-------1-----+--------------+----------+----
Stu1        -------------1----------1--------+---------+-----+-------------+--------------+----------+----
Sty1        ---1---+----1-----+-----+-----11--+--1--+--1-+--1---------+------+----------+----1-----+----
Tag1        ---------+-1-1--2-1-----1-1-----1-3-1---1---+-----+----1-----+--------------+------1----1-----
```

Pst1
Pvu1
Pvu2
Rsa1
Rsr2
Sac1
Sau1
Sau3A1
Sau96I
Sca1
ScrF1
Sdu1
Sec1
SfaN1
Sfi1
Sma1
Spe1
Sph1
Ssp1
Sst1
Stu1
Sty1
Tag1

TABLE 5-continued

From 1 to 6365. Numbered from position 1.

```
LXSNRIIL2 ------1000+------2000+------3000+------4000+------5000+------6000+---
Mo-MuSV 5' long ter  ------>
- (Split)
1 to 683 of RIIL2          ------>    ========>
neomycin phosphotra                              ------>
Mo-MuLV 3' long ter
signal                           1

Tha1       ---21-----2--1-------+-------------1--+2------2-+21---1-----+1---1-----1+---1-
Tth111I    --------1---1-+------+--------1-+------1-+---1------+--------+--------+-----
Xba1       --------------1+------1+-------------+-------1---------+--------+--------+-----
Xho1       ---------------+------+-------------1---------+--------+--------+--------+-----
Xho2       ---------------+------+------1--1---1--1+-------+-----+112------2--------+-----
Xma1       ---1-----------+------+-------------+---------1+-------+--------+--------+-----
Xma3       ---------------+------+------1------+---------+--------+--------+-----1--+-----
Xmn1       ---------------+------+-------------+---------+--------+--------+-----1--+-----
Xor2       ---------------+------+-------------+---------+--------+-----1--+--------+-----
```

TABLE 6
from 1 to 6365. Numbered from position 1.
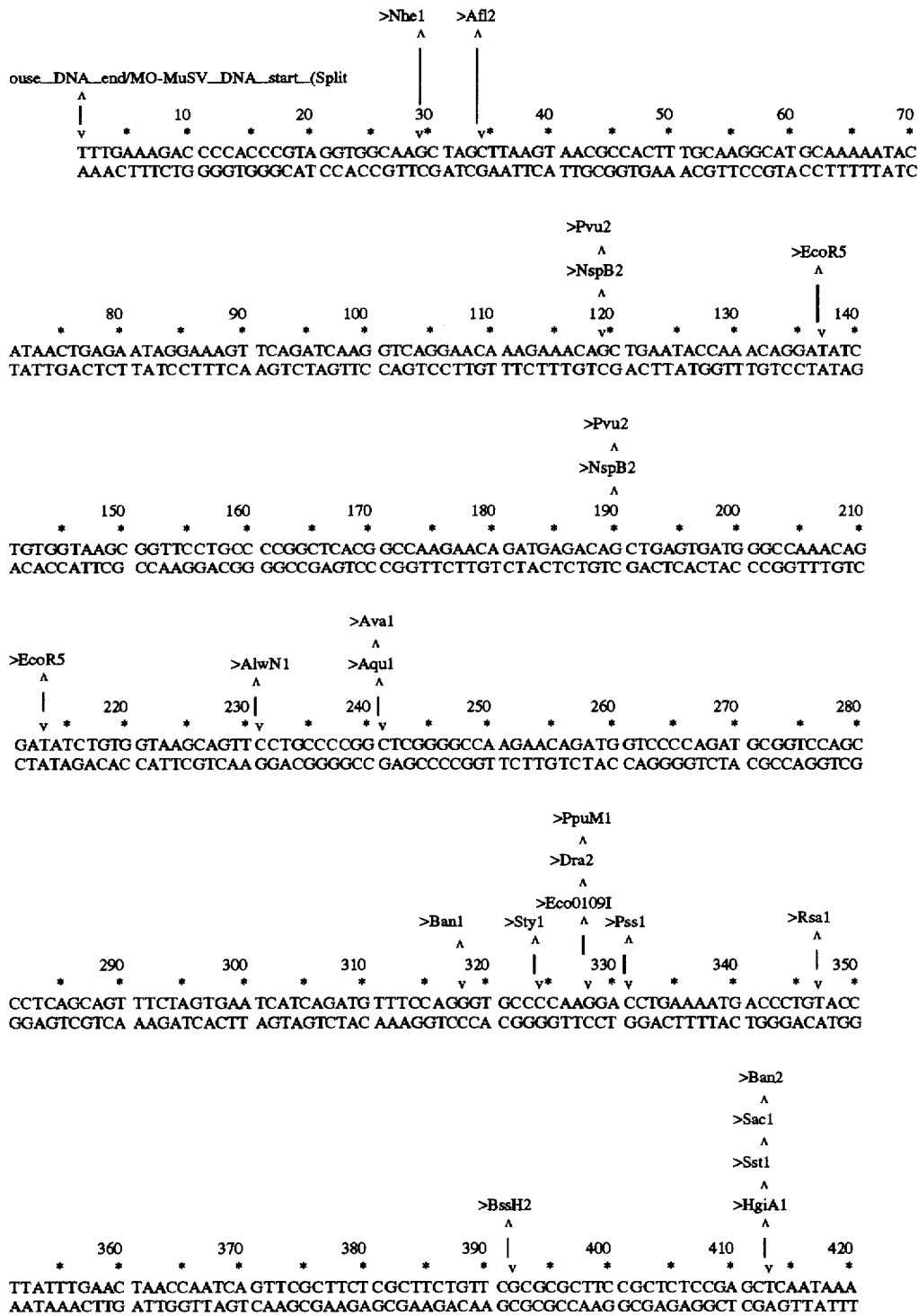

TABLE 6-continued
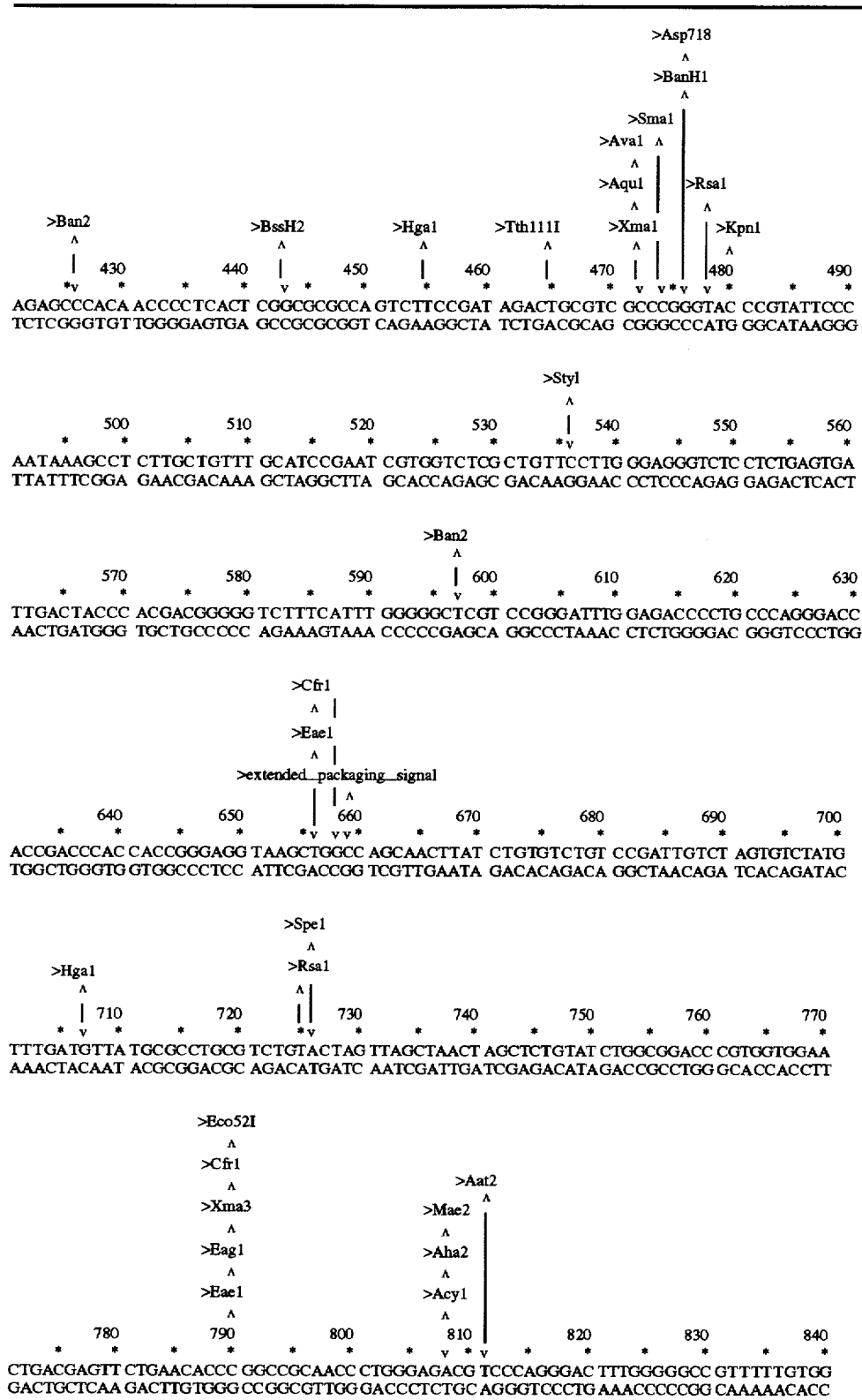

TABLE 6-continued

```
   >EcoN1
      ^
>Bsu36I
   ^
>Aoc1
   ^
>Sau1
   ^
>Eco8I
   ^
>Cvn1
   ^
>Mst2                    >Ple1          >Tth111I
   ^                        ^               ^
   | 850      860      | 870      | 880       890        900        910
   *  v  *    *   *    *   v  *   *  v  *    *     *    *     *    *     *
CCCGACCTGA GGAAGGGAGT CGATGTGGAA TCCGACCCCG TCAGGATATG TGGTTCTGGT AGGAGACGAG
GGGCTGGACT CCTTCCCTCA GCTACACCTT AGGCTGGGGC AGTCCTATAC ACCAAGACCA TCCTCTGCTC

>HgaI
                                                    ^
      920        930        940        950        960        970        980
   *     *    *     *    *     *    *     *    *     *    *     *    *     *
AACCTAAAAC AGTTCCCGCC TCCGTCTGAA TTTTTGCTTT CGGTTTGGAA CCGAAGCCGC GCGTCTTGTC
TTGGATTTTG TCAAGGGCGG AGGCAGACTT AAAAACGAAA GCCAAACCTT GGCTTCGGCG CGCAGAACAG

>PstI
   ^
   | 990       1000       1010       1020       1030       1040       1050
   *  v  *    *     *    *     *    *     *    *     *    *     *    *     *
TGCTGCAGCA TCGTTCTGTG TTGTCTCTGT CTGACTGTGT TTCTGTATTT GTCTGAAAAT TAGGGCCAGA
ACGACGTCGT AGCAAGACAC AACAGAGACA GACTGACACA AAGACATAAA CAGACTTTTA ATCCCGGTCT

> Aoc1
                          ^
                       > Sau1
                          ^
                       > Cvn1
                          ^
                       >Mst2
                          ^
                       >Bsu36I
                          ^
          >Afl2        >Eco81I
            ^             ^
   1060    | 1070       | 1080       1090       1100       1110       1120
   *  ' *   v  *    *   *v  *    *     *    *     *    *     *    *     *
CTGTTACCAC TCCCTTAAGT TTGACCTTAG GTCACTGGAA AGATGTCGAG CGGATCGCTC ACAACCAGTC
GACAATGGTG AGGGAATTCA AACTGGAATC CAGTGACCTT TCTACAGCTC GCCTAGCGAG TGTTGGTCAG

>Cfr1
                                                        ^
                                  >AspA1              >Eae1                  >Eae1
                                    ^                   ^                       ^
                     >Mae2 >BstE2              >PstI |>Ball       >Mae2       >Cfr1
                       ^    ^                    ^      ^           ^            ^
      1130        1140   | 1150       1160    |  1170       1180       1190
   *     *    *    v *    *     *    *     *    * v * v v *    *     *    * v  *
GGTAGATGTC AAGAAGAGAC GTTGGGTTAC CTTCTGCTCT GCAGAATGGC CAACCTTTAA CGTCGGATGG
CCATCTACAG TTCTTCTCTG CAACCCAATG GAAGACGAGA CGTCTTACCG GTTGGAAATT GCAGCCTACC >Ban1          >Hph1                    >Hph1
         ^              ^                        ^
      1200       1210 | 1220       1230       1240       1250       1260
   *     *    *     *   v *    *     *    *     *    *     *    *     *
CCGCGAGACG GCACCTTTAA CCGAGACCTC ATCACCCAGG TTAAGATCAA GGTCTTTTCA CCTGGCCCGC
GGCGCTCTGC CGTGGAAATT GGCTCTGGAG TAGTGGGTCC AATTCTAGTT CCAGAAAAGT GGACCGGGCG
```

TABLE 6-continued

```
                    >Pss1
         >Dra2       ^
          ^
      >Eco0109I
          ^
       >PpuM1
          ^
      >Tth111I                          >Sty1
          ^                               ^
    1270   |  | 1280    1290    1300    |   1310    1320    1330
    *   *  *  *v  *   *   *   *   *   *  v *   *   *   *   *   *
ATGGACACCC AGACCAGGTC CCCTACATCG TGACCTGGGA AGCCTTGGCT TTTGACCCCC CTCCCTGGGT
TACCTGTGGG TCTGGTCCAG GGGATGTAGC ACTGGACCCT TCGGAACCGA AAACTGGGGG GAGGGACCCA

>Rsa1
         ^
    1340  |   1350    1360    1370    1380    1390    1400
    *   * v *   *   *   *   *   *   *   *   *   *   *
CAAGCCCTTT GTACACCCTA AGCCTCCGCC TCCTCTTCCT CCATCCGCCC CGTCTCTCCC CCTTGAACCT
GTTCGGGAAA CATGTGGGAT TCGGAGGCGG AGGAGAAGGA GGTAGGCGGG GCAGAGAGGG GGAACTTGGA

>EcoN1      >EcoR1
                                                ^           ^
    1410    1420    1430    1440    1450    1460    1470
    *   *   *   *   *   *   *   *   *   *   *   *   *
CCTCGTTCGA CCCCGCCTCG ATCCTCCCTT TATCCAGCCC TCACTCCTTC TCTAGGCGGG AATTCGTTAG
GGAGCAAGCT GGGGCGGAGC TAGGAGGGAA ATAGGTCGGG AGTGAGGAAG AGATCCGCCC TTAAGCAATC

>BspM1              >Rsa1
                        ^                   ^
    1480    1490    1500 |   1510    1520    1530    1540
    *   *   *   *   *   *  v *   *   *   v*  *   *   *
CTTGGTAAGT GACCAGCTAC AGTCGGAAAC CATCAGCAAG CAGGTATGTA CTCTCCAGGG TGGGCCTGGC
GAACCATTCA CTGGTCGATG TCAGCCTTTG GTAGTCGTTC GTCCATACAT GAGAGGTCCC ACCCGGACCG

>Rsa1
                                                              ^
                                                           >NspH1
                                                             ^|
                                >Ban2         >Nsp(7524)1
                                  ^                ^
   >Ple1                   >Hga1        >Af13             >Nhe1
     ^                       ^            ^                ^
    1550    1560    1570    1580  |   1590  |      1600   |   1610
    * v *   *   *   *   *   *   * v *   *   *  v *vv *   *
TTCCCCAGTC AAGACTCCAG GGATTTGAGG GACGCTGTGG GCTCTTCTCT TACATGTACC TTTTGCTAGC
AAGGGGTCAG TTCTGAGGTC CCTAAACTCC CTGCGACACC CGAGAAGAGA ATGTACATGG AAAACGATCG 1620    1630    1640    1650    1660    1670    1680
    *   *   *   *   *   *   *   *   *   *   *   *   *
CTCAACCCTG ACTATCTTCC AGGTCATTGT TCCAACATGG CCCTGTGGAT CGACAGGATG CAACTCCTGT
GAGTTGGGAC TGATAGAAGG TCCAGTAACA AGGTTGTACC GGGACACCTA GCTGTCCTAC GTTGAGGACA

>HgiA1
                                ^
                    >ApaL1     |
                      ^
    1690    1700    1710    1720 |   1730    1740    1750
    *   *   *   *   *   * v * v *   *   *   *   *   *
CTTGCATTGC ACTAAGTCTT GCACTTGTCA CAAACAGTGC ACCTACTTCA AGTTCTACAA AGAAAACACA
GAACGTAACG TGATTCAGAA CGTGAACAGT GTTTGTCACG TGGATGAAGT TCAAGATGTT TCTTTTGTGT

>Pvu2
  ^
>NspB2                                     >Ase1         >Hph1
  ^                                          ^             ^
  |  1760    1770    1780    1790    1800 |   1810    1820
  *v *   *   *   *   *   *   *   *   *   *   *   *v *   *
GCTGCAACTG GAGCATTTAC TGCTGGATTT ACAGATGATT TTGAATGGAA TTAATAATTA CAAGAATCCC
CGACGTTGAC CTCGTAAATG ACGACCTAAA TGTCTACTAA AACTTACCTT AATTATTAAT GTTCTTAGGG
```

TABLE 6-continued

```
         >Sph1
          ^
  >Nap(7524)1              >NspH1
     ^                        ^
  >NspH1                   >Nsp(7524)1                                          >Pst1
     ^                        ^                                                   ^
    1830     |   1840      1850     |   1860       1870       1880       1890
     *   *    *    *    *    *    *v   *    *    *    *    *    *    *v   *
AAACTCACCC GCATGCTCAC ATTTAAGTTT TACATGCCCA AGAAGGCCAC AGAACTGAAA CATCTGCAGT
TTTGAGTGGG CGTACGAGTG TAAATTCAAA ATGTACGGGT TCTTCCGGTG TCTTGACTTT GTAGACGTCA

>Xba1                                                                        >Afl2
    ^                                                                            ^
    |     1900       1910       1920       1930       1940       1950      |   1960
    v  *    *    *    *    *    *    *    *    *    *    *    *    *    *    *
GTCTAGAAGA AGAACTCAAA CCTCTGGAGG AAGTGCTAAA TTTAGCTCAA AGCAAAAACT TTCACTTAAG
CAGATCTTCT TCTTGAGTTT GGAGACCTCC TTCACGATTT AAATCGAGTT TCGTTTTTGA AAGTGAATTC

>Ava1
                                          ^
                                        >Aqu1
   >Avr2                                  ^
     ^                                  >Cvr1
   >Sty1                                  ^
     ^                                  >PaeR7I      >Xho2
   >Stu1                                  ^            ^
    ^|                 >Mae2            >Xho1        >BstY1
   >Aat1                 ^                ^            ^
    ^|     1970       1980       1990       2000       2010       2020       2030
    ||  *    *    *    *    *    *    *    *    *    *    *    *    *    *
    vv                       v            v
GCCTAGGGAC TTAATCAGCA ATATCAACGT AATAGTTCTC GAGCTAAAGG GATCTGAAAC AACATTCATG
CGGATCCCTG AATTAGTCGT TATAGTTGCA TTATCAAGAG CTCGATTTCC CTAGACTTTG TTGTAAGTAC

>BstX1
                            ^
    2040       2050       2060       2070       2080       2090       2100
     *    *    *    *    *    *    *    *    *    *    *    *    *    *
TGTGAATATG CTGATGAGAC AGCCACCATT GTGGAATTTC TGAACAGATG GATTACCTTT TGTCAAAGCA
ACACTTATAC GACTACTCTG TCGGTGGTAA CACCTTAAAG ACTTGTCTAC CTAATGGAAA ACAGTTTCGT

>BamH1
                                                              ^
                                                            >BstY1
                                                              ^
                                                           >Xho2  >NspB2
                                                              ^    ^
                                                      >simian_virus_40_early_promoter
                                                              |    |
                                            >Mo-MuSV_DNA_end/simian_virus_40_DNA_start
                                                              ^    |
    2110       2120       2130       2140       2150    |   2160       2170
     *    *    *    *    *    *    *    *    *    *    *    *    *    *
                                                         v        vv*
TCATCTCAAC ACTAACTTGA TAATTAAGTG CTTCCCACTT AAAACATATC AGGATCCGCT GTGGAATGTG
AGTAGAGTTG TGATTGAACT ATTAATTCAC GAAGGGTGAA TTTTGTATAG TCCTAGGCGA CACCTTACAC >EcoT22I
                                                                        ^
                                                                      >Nsi1
                                                                        ^
                                                                      >Ava3
                                                                        ^
                                                                   >Nsp(7524)1
                                                                        ^ |
                                                                      >NspH1
                                                                        ^
                                                                      >Sph1
                                                                        ^
    2180       2190       2200       2210       2220       2230     |   2240
     *    *    *    *    *    *    *    *    *    *    *    *    *    *
                                                                     v
TGTCAGTTAG GGTGTGAAA GTCCCCAGGC TCCCCAGCAG GCAGAAGTAT GCAAAGCATG CATCTCAATT
ACAGTCAATC CCACACCTTT CAGGGGTCCG AGGGGTCGTC CGTCTTCATA CGTTTCGTAC GTAGAGTTAA
```

TABLE 6-continued

```
                                                                              >Nsi1
                                                                               ^
                                                                              >Ava3
                                                                               ^
                                                                              >EcoT22I
                                                                               ^
                                                                              >Nsp(7524)1
                                                                               ^ |
                                                                              >NspH1
                                                                               ^ |
                                                                              >Sph1
                                                                               ^ |
          2250       2260       2270       2280       2290       2300       |  | 2310
           *          *          *          *          *          *       v  v*
      AGTCAGCAAC CAGGTGTGGA AAGTCCCCAG GCTCCCCAGC AGGCAGAAGT ATGCAAAGCA TGCATCTCAA
      TCAGTCGTTG GTCCACACCT TTCAGGGGTC CGAGGGGTCG TCCGTCTTCA TACGTTTCGT ACGTAGAGTT 2320       2330       2340       2350       2360       2370       2380
           *          *          *          *          *          *          *
      TTAGTCAGCA ACCATAGTCC CGCCCCTAAC TCCGCCCATC CCGCCCCTAA CTCCGCCCAG TTCCGCCCAT
      AATCAGTCGT TGGTATCAGG GCGGGGATTG AGGCGGGTAG GGCGGGGATT GAGGCGGGTC AAGGCGGGTA

>Nco1                                               >Sfi1
         ^                                                   ^
        >Sty1                                               >Bgl1
         ^                                                   ^
          2390       2400       2410       2420       2430      | 2440       2450
           * v*        *          *          *          *          *          *
      TCTCCGCCCC ATGGCTGACT AATTTTTTTT ATTTATGCAG AGGCCGAGGC CGCCTCGGCC TCTGAGCTAT
      AGAGGCGGGG TACCGACTGA TTAAAAAAAA TAAATACGTC TCCGGCTCCG GCGGAGCCGG AGACTCGATA

>Sty1
                             ^
                            >Avr2
                             ^
                            >Stu1            >BspM1
                             ^ |              ^
                            >Aat1            >Hind3     >Pst1
                             ^ |              ^ |        ^
          2460       2470       2480 | |  2490       2500       2510  |    2520
           *          *          *    vv     *          * v        *     v    *
      TCCAGAAGTA GTGAGGAGGC TTTTTTGGAG GCCTAGGCTT TTGCAAAAAG CTTGGGCTGC AGGTCGAGGC
      AGGTCTTCAT CACTCCTCCG AAAAAACCTC CGGATCCGAA AACGTTTTC GAACCCGACG TCCAGCTCCG >Bcl1
                ^
      >Xho2    |
       ^       |
      >BstY1   |
       ^       |
      mian_virus_DNA_end/Tn5_DNA_start                              >BspM1
       ^       |                                                     ^
       |       | 2530       2540       2550       2560       2570  |      2580
       v     *v    *          *          *          *  *          * v        *
      GGATCTGATC AAGAGACAGG ATGAGGATCG TTTCGC ATG ATT GAA CAA GAT GGA TTG CAC GCA GGT TCT
      CCTAGACTAG TTCTCTGTCC TACTCCTAGC AAAGCG TAC TAA CTT GTT CTA CCT AAC GTG CGT CCA AGA
                                             Met Ile Glu Gln Asp Gly Leu His Ala Gly Ser>

>Eco52I
       ^
      >Eag1
       ^
      >Eae1
       ^
      >Cfr1
       ^
      >Xma3
       ^
      2590|       2600       2610       2620       2630       2640       2650
        *v          *          *          *          *          *          *
      CCG GCC GCT TGG GTG GAG AGG CTA TTC GGC TAT GAC TGG GCA CAA CAG ACA ATC GGC TGC TCT
      GGC CGG CGA ACC CAC CTC TCC GAT AAG CCG ATA CTG ACC CGT GTT GTC TGT TAG CCG ACG AGA
      Pro Ala Ala Trp Val Glu Arg Leu Phe Gly Tyr Asp Trp Ala Gln Gln Thr Ile Gly Cys Ser>
```

TABLE 6-continued

```
                                              >Hae2
                                                ʌ
                                              >Bbe1
                                                ʌ
                                              >Nar1
                                                ʌ
                                              >Acy1
                                                ʌ
                                              >Aha2
                                                ʌ
                                              >Ban1
                                                ʌ
        2660        2670        2680    |   | 2690        2700        2710
         *           *           *      v   v *           *           *
       GAT GCC GCC GTG TTC CGG CTG TCA GCG CAG GGG CGC CCG GTT CTT TTT GTC AAG ACC GAC CTG
       CTA CGG CGG CAC AAG GCC GAC AGT CGC GTC CCC GCG GGC CAA GAA AAA CAG TTC TGG CTG GAC
       Asp Ala Ala Val Phe Arg Leu Ser Ala Gln Gly Arg Pro Val Leu Phe Val Lys Thr Asp Leu>

>Bal1
                                                                                ʌ
                                                                         >Cfr1
                                                                           ʌ
                                                                         >Eae1
      >Ban1                            >Pst1                               ʌ
        ʌ                                ʌ
        2720        2730        2740        2750        2760       |   | 2770
      v  *           *           * v         *           *         *   v *           *
       TCC GGT GCC CTG AAT GAA CTG CAG GAC GAC GCA GCG CGG CTA TCG TGG CTG GCC ACG ACG GGC
       AGG CCA CGG GAC TTA CTT GAC GTC CTG CTG CGT CGC GCC GAT AGC ACC GAC CGG TGC TGC CCG
       Ser Gly Ala Leu Asn Glu Leu Gln Asp Glu Ala Ala Arg Leu Ser Trp Leu Ala Thr Thr Gly>

>Fsp1
                    ʌ
                  >Aos1
                    ʌ                                >Tth111I
                  >Fdi2    >Pvu2    >HgiA1             ʌ
                    ʌ        ʌ        ʌ
                  >Mst1    >NspB2      >Mae2
                    ʌ        ʌ          ʌ
        2780       | 2790 |          2800 |             2810        2820        2830        2840
         *         * v   * v            *  v            *           *           *           *
       GTT CCT TGC GCA GCT GTG CTC GAC GTT GTC ACT GAA GCG GGA AGG GAC TGG CTG CTA TTG GGC
       CAA GGA ACG CGT CGA CAC GAG CTG CAA CAG TGA CTT CGC CCT TCC CTG ACC GAC GAT AAC CCG
       Val Pro Cys Ala Ala Val Leu Asp Val Val Thr Glu Ala Gly Arg Asp Trp Leu Leu Leu Gly>

>BstY1
                 ʌ
               >Xho2        >Hph1
                 ʌ            ʌ
        2850   |  2860    |   2870        2880        2890        2900
         *     *    * v    *  v *           *           *           *
       GAA GTG CCG GGG CAG GAT CTC CTG TCA TCT CAC CTT GCT CCT GCC GAG AAA GTA TCC ATC ATG
       CTT CAC GGC CCC GTC CTA GAG GAC AGT AGA GTG GAA CGA GGA CGG CTC TTT CAT AGG TAG TAC
       Glu Val Pro Gly Gln Asp Leu Leu Ser Ser His Leu Ala Pro Ala Glu Lys Val Ser Ile Met>

>BspM1
                                                                    ʌ
        2910        2920        2930        2940        2950    |   2960
         *           *           *           *           *      v *           *
       GCT GAT GCA ATG CGG CGG CTG CAT ACG CTT GAT CCG GCT ACC TGC CCA TTC GAC CAC CAA GCG
       CGA CTA CGT TAC GCC GCC GAC GTA TGC GAA CTA GGC CGA TGG ACG GGT AAG CTG GTG GTT CGC
       Ala Asp Ala Met Arg Arg Leu His Thr Leu Asp Pro Ala Thr Cys Pro Phe Asp His Gln Ala>

>Rsa1
                                ʌ
                      >HgiA1
                        ʌ
                      >Mae2                    >Cfr10I
                        ʌ                        ʌ
        2970        2980        2990   |    3000        3010   |    3020        3030
         *           *           * v     *v    *           *   v *           *           *
       AAA CAT CGC ATC GAG CGA GCA CGT ACT CGG ATG GAA GCC GGT CTT GTC GAT CAG GAT GAT CTG
       TTT GTA GCG TAC CTC GCT CGT GCA TGA GCC TAC CTT CGG CCA GAA CAG CTA GTC CTA CTA GAC
       Lys His Arg Ile Glu Arg Ala Arg Thr Arg Met Glu Ala Gly Leu Val Asp Gln Asp Asp Leu>
```

TABLE 6-continued

```
                                                                    >Sph1
                                                                      ʌ
                                                                 >Nsp(7524)1
                                                                      ʌ
       >Ban2                                            >BssH2    >NspH1
         ʌ                                                 ʌ         ʌ
    3040       3050       3060       3070       3080         3090
     *    *    *    *    *    *    *    *    *    * v  *    *
GAC GAA GAG CAT CAG GGG CTC GCG CCA GCC GAA CTG TTC GCC AGG CTC AAG GCG CGC ATG CCC
CTG CTT CTC GTA GTC CCC GAG CGC GGT CGG CTT GAC AAG CGG TCC GAG TTC CGC GCG TAC GGG
Asp Glu Glu His Gln Gly Leu Ala Pro Ala Glu Leu Phe Ala Arg Leu Lys Ala Arg Met Pro>

>Xho2            >Nco1                                              >Cfr1
         ʌ                ʌ                                                  ʌ
       >BstY1           >Sty1                                              >Eae1
         ʌ                ʌ                                                  ʌ
    3100 |      3110   | 3120       3130       3140       3150           |
     *    * v  *    *    * v  *    *    *    *    *    *    *    *    * v
GAC GGC GAG GAT CTC GTC GTG ACC CAT GGC GAT GCC TGC TTG CCG AAT ATC ATG GTG GAA AAT
CTG CCG CTC CTA GAG CAG CAC TGG GTA CCG CTA CGG ACG AAC GGC TTA TAG TAC CAC CTT TTA
Asp Gly Glu Asp Leu Val Val Thr His Gly Asp Ala Cys Leu Pro Asn Ile Met Val Glu Asn>

>Cfr10I
                        >Cfr1    ʌ
                          ʌ
                        >Eae1   | >Nae1         >Rsr2
                          ʌ     |   ʌ             ʌ
    3160       3170       3180 |   | 3190    3200|       3210
     *    *    *    *    *    * v  * v  *    *    *    *    *
GGC CGC TTT TCT GGA TTC ATC GAC TGT GGC CGG CTG GGT GTG GCG GAC CGC TAT CAG GAC ATA
CCG GCG AAA AGA CCT AAG TAG CTG ACA CCG GCC GAC CCA CAC CGC CTG GCG ATA GTC CTG TAT
Gly Arg Phe Ser Gly Phe Ile Asp Cys Gly Arg Leu Gly Val Ala Asp Arg Tyr Gln Asp Ile>

3220       3230       3240       3250       3260       3270       3280
     *    *    *    *    *    *    *    *    *    *    *    *    *    *
GCG TTG GCT ACC CGT GAT ATT GCT GAA GAG CTT GGC GGC GAA TGG GCT GAC CGC TTC CTC GTG
CGC AAC CGA TGG GCA CTA TAA CGA CTT CTC GAA CCG CCG CTT ACC CGA CTG GCG AAG GAG CAC
Ala Leu Ala Thr Arg Asp Ile Ala Glu Glu Leu Gly Gly Glu Trp Ala Asp Arg Phe Leu Val>

3290       3300       3310       3320       3330       3340
     *    *    *    *    *    *    *    *    *    *    *    *
CTT TAC GGT ATC GCC GCT CCC GAT TCG CAG CGC ATC GCC TTC TAT CGC CTT CTT GAC GAG TTC
GAA ATG CCA TAG CGG CGA GGG CTA AGC GTC GCG TAG CGG AAG ATA GCG GAA GAA CTG CTC AAG
Leu Tyr Gly Ile Ala Ala Pro Asp Ser Gln Arg Ile Ala Phe Tyr Arg Leu Leu Asp Glu Phe>

>Ple1
   ʌ
   |        >Tn5_DNA_end/_Mo-MuLV_DNA_start
                             ʌ
    3350       3360       3370       3380       3390       3400       3410       3420
     *    *    *    *    *    *    *    *    *    *    *    *    *    *    *
TTC TGA GCGGGACTC TGGGGTTCGA TAAAATAAAA GATTTTATTT AGTCTCCAGA AAAAGGGGGG AATGAAAGAC
AAG ACT CGCCCTGAG ACCCCAAGCT ATTTTATTTT CTAAAATAAA TCAGAGGTCT TTTTCCCCCC TTACTTTCTG
Phe End>

>Afl2
                             ʌ
                 >Nhe1       |
                   ʌ         |
    3430       3440 |      | 3450       3460       3470       3480       3490
     *    *    *    * v  * v  *    *    *    *    *    *    *    *
CCCACCTGTA GGTTTGGCAA GCTAGCTTAA GTAACGCCAT TTTGCAAGGC ATGGAAAAAT ACATAACTGA
GGGTGGACAT CCAAACCGTT CGATCGAATT CATTGCGGTA AAACGTTCCG TACCTTTTTA TGTATTGACT

>NspB2
                                        ʌ
                                      >Pvu2                   >EcoR5
                                        ʌ                        ʌ
    3500       3510       3520       3530 |     3540       3550 |     3560
     *    *    *    *    *    *    *    * v  *    *    *    * v *    *
GAATAGAGAA GTTCAGATCA AGGTCAGGAA CAGATGGAAC AGCTGAATAT GGGCCAAACA GGATATCTGT
CTTATCTCTT CAAGTCTAGT TCCAGTCCTT GTCTACCTTG TCGACTTATA CCCGGTTTGT CCTATAGACA
```

TABLE 6-continued

```
                                        >NspB2
                                           ʌ
       >AlwN1                           >Pvu2                    >EcoR5
          ʌ                                ʌ                       ʌ
    3570      3580      3590      3600      3610      3620      3630
 *    *  v  *    *    *    *    *    *    *  v  *    *    *    *  v *
GGTAAGCAGT TCCTGCCCCG GCTCAGGGCC AAGAACAGAT GGAACAGCTG AATATGGGCC AAACAGGATA
CCATTCGTCA AGGACGGGGC CGAGTCCCGG TTCTTGTCTA CCTTGTCGAC TTATACCCGG TTTGTCCTAT

>AlwN1
                 ʌ
    3640      3650      3660      3670      3680      3690      3700
 *    *    *  v  *    *    *    *    *    *    *    *    *    *    *
TCTGTGGTAA GCAGTTCCTG CCCCGGCTCA GGGCCAAGAA CAGATGGTCC CCAGATGCGG TCCAGCCCTC
AGACACCATT CGTCAAGGAC GGGGCCGAGT CCCGGTTCTT GTCTACCAGG GGTCTACGCC AGGTCGGGAG

>Pss1
                                    ʌ
                                  >Dra2  |
                                    ʌ    |
                                >Eco0109I |
                                    ʌ    |
                         >Ban1   >PpuM1   |
    >Xba1                  ʌ   >Sty1  ʌ   |
       ʌ                   |     ʌ    |   |
    3710      3720      3730      3740      3750      3760      3770
 *  v  *    *    *    *    *  v *    *  v *    *    *    *    *    *
AGCAGTTTCT AGAGAACCAT CAGATGTTTC CAGGGTGCCC CAAGGACCTG AAATGACCCT GTGCCTTATT
TCGTCAAAGA TCTCTTGGTA GTCTACAAAG GTCCCACGGG GTTCCTGGAC TTTACTGGGA CACGGAATAA

>Sac1
                                                                ʌ
                                                              >HgiA1
                                                       >Aqu1    ʌ
                                                         ʌ    >Sst1
                                                       >Ava1    ʌ
                                    >BssH2               ʌ    >Ban2
                                      ʌ                  |      ʌ
    3780      3790      3800      3810      3820      3830      3840
 *    *    *    *    *    *    *  v *    *    *  v *  v *    *    *
TGAACTAACC AATCAGTTCG CTTCTCGCTT CTGTTCGCGC GCTTCTGCTC CCCGAGCTCA ATAAAAGAGC
ACTTGATTGG TTAGTCAAGC GAAGAGCGAA GACAAGCGCG CGAAGACGAG GGGCTCGAGT TATTTTCTCG

>Ban1
                                                        ʌ
                                                      >Asp718
                       >Hae2                            ʌ
                         ʌ                            >Ple1
                       >Bbe1                            ʌ
              >Nar1      ʌ                            >Sma1
                ʌ        |                              ʌ
              >Ban1                                   >Xma1
                ʌ                                       ʌ
                       >Acy1                          >Ava1
       >Aqu1    ʌ                                       ʌ   >Kpn1
         ʌ    >Aha2                                             ʌ
 >Ban2 >Ava1    ʌ                                     >Aqu1   >Rsa1
   ʌ     ʌ      |                >Tth111I               ʌ      ʌ
   |     |      |                   ʌ                   |      |
    3850      3860      3870      3880      3890      3900      3910
 *  v  *    *  v *  v *    *    *    *    *    *  v *  v *  v *    *
CCACAACCCC TCACTCGGGG CGCCAGTCCT CCGATTGACT GAGTCGCCCG GGTACCCGTG TATCCAATAA
GGTGTTGGGG AGTGAGCCCC GCGGTCAGGA GGCTAACTGA CTCAGCGGGC CCATGGCAC ATAGGTTATT

>Sty1
                         ʌ
    3920      3930      3940      3950      3960      3970      3980
 *    *    *    *    *    *    *    *    *    *    *    *    *    *
ACCCTCTTGC AGTTGCATCC GACTTGTGGT CTCGCTGTTC CTTGGGAGGG TCTCCTCTGA GTGATTGACT
TGGGAGAACG TCAACGTAGG CTGAACACCA GAGCGACAAG GAACCCTCCC AGAGGAGACT CACTAACTGA
```

TABLE 6-continued

```
          >NspB2                    >Ban2
          ^                         ^
          3990          4000        4010  |   4020         4030         4040         4050
        *    v *     *     *     *     * v  *     *     *     *     *     *     *     *
     ACCCGTCAGC GGGGGTCTTT CATTTGGGGG CTCGTCCGGG ATCGGGAGAC CCCTGCCCAG GGACCACCGA
     TGGGCAGTCG CCCCCAGAAA GTAAACCCCC GAGCAGGCCC TAGCCCTCTG GGGACGGGTC CCTGGTGGCT

>Nsp(7524)1
                                                                                *
                                                         >Hph1        >Hph1   >NspH1
          >Mo-MuLV_DNA_end/plasmid_pBR322_DNA_start       ^            ^      ^
                                            ^             |            |      |
          4060          4070  |   4080        4090        4100  |     4110 |  4120
        *    *     *     *   |   *     *     *     *     *     |  *   *  |  *     v *
     CCCACCACCG GGAGGTAAGC TGGCTGCCTC GCGCGTTTCG GTGATGACGG TGAAAACCTC TGACACATGC
     GGGTGGTGGC CCTCCATTCG ACCGACGGAG CGCGCAAAGC CACTACTGCC ACTTTTGGAG ACTGTGTACG >Hga1
                                                             ^
          4130          4140         4150         4160         4170  |   4180         4190
        *    *     *     *     *     *     *     *     *     *     *   |  *     *     *
     AGCTCCCGGA GACGGTCACA GCTTGTCTGT AAGCGGATGC CGGGAGCAGA CAAGCCCGTC AGGGCGCGTC
     TCGAGGGCCT CTGCCAGTGT CGAACAGACA TTCGCCTACG GCCCTCGTCT GTTCGGGCAG TCCCGCGCAG >NspB2                        >Tth111I   >Mae2                 >Acc1
     ^                             ^          ^                     ^
     |   4200          4210         4220  |   4230         4240   | 4250         4260
     v  *    *     *     *     *     *   v *  *     *     * v *   |  *     *     *
     AGCGGGTGTT GGCGGGTGTC GGGGCGCAGC CATGACCCAG TCACGTAGCG ATAGCGGAGT GTATACTGGC
     TCGCCCACAA CCGCCCACAG CCCCGCGTCG GTACTGGGTC AGTGCATCGC TATCGCCTCA CATATGACCG >HgiA1
                                               ^
                         >Rsa1      >ApaL1    | >Nde1
                         ^          ^         | ^
          4270          4280         4290  |   4300  |  4310         4320         4330
        *    *     *     *     *     *   v *  *  v  *  *     *     *     *     *     *
     TTAACTATGC GGCATCAGAG CAGATTGTAC TGAGAGTGCA CCATATGCGG TGTGAAATAC CGCACAGATG
     AATTGATACG CCGTAGTCTC GTCTAACATG ACTCTCACGT GGTATACGCC ACACTTTATG GCGTGTCTAC >Hae2               >Ple1
                              ^                   ^
          4340          4350         4360         4370  |   4380         4390         4400
        *    *     *     *     *     *     *   v *  *  v *  *     *     *     *     *
     CGTAAGGAGA AAATACCGCA TCAGGCGCTC TTCCGCTTCC TCGCTCACTG ACTCGCTGCG CTCGGTCGTT
     GCATTCCTCT TTTATGGCGT AGTCCGCGAG AAGGCGAAGG AGCGAGTGAC TGAGCGACGC GAGCCAGCAA 4410          4420         4430         4440         4450         4460         4470
        *    *     *     *     *     *     *     *     *     *     *     *     *     *
     CGGCTGCGGC GAGCGGTATC AGCTCACTCA AAGGCGGTAA TACGGTTATC CACAGAATCA GGGGATAACG
     GCCGACGCCG CTCGCCATAG TCGAGTGAGT TTCCGCCATT ATGCCAATAG GTGTCTTAGT CCCCTATTGC >Nsp(7524)1
          ^
          >NspH1
          ^
     >Afl3 |
     ^     |
     4480  |   4490         4500         4510         4520         4530         4540
     *    v *  *     *     *     *     *     *     *     *     *     *     *     *
     CAGGAAAGAA CATGTGAGCA AAAGGCCAGC AAAAGGCCAG GAACCGTAAA AAGGCCGCGT TGCTGGCGTT
     GTCCTTTCTT GTACACTCGT TTTCCGGTCG TTTTCCGGTC CTTGGCATTT TTCCGGCGCA ACGACCGCAA >Hga1
                                                             ^
          4550          4560         4570         4580         4590  |   4600         4610
        *    *     *     *     *     *     *     *     *     *     *   v  *     *     *
     TTTCCATAGG CTCCGCCCCC CTGACGAGCA TCACAAAAAT CGACGCTCAA GTCAGAGGTG GCGAAACCCG
     AAAGGTATCC GAGGCGGGGG GACTGCTCGT AGTGTTTTTA GCTGCGAGTT CAGTCTCCAC CGCTTTGGGC 4620          4630         4640         4650         4660         4670         4680
        *    *     *     *     *     *     *     *     *     *     *     *     *     *
     ACAGGACTAT AAAGATACCA GGCGTTTCCC CCTGGAAGCT CCCTCGTGCG CTCTCCTGTT CCGACCCTGC
     TGTCCTGATA TTTCTATGGT CCGCAAAGGG GGACCTTCGA GGGAGCACGC GAGAGGACAA GGCTGGGACG
```

TABLE 6-continued

```
                                                       >Hae2
                                                         ∧
     4690       4700       4710       4720       4730       4740       4750
   *    *    *    *    *    *    *    *    *    *  v *    *    *    *
CGCTTACCGG ATACCTGTCC GCCTTTCTCC CTTCGGGAAG CGTGGCGCTT TCTCATAGCT CACGCTGTAG
GCGAATGGCC TATGGACAGG CGGAAAGAGG GAAGCCCTTC GCACCGCGAA AGAGTATCGA GTGCGACATC

>HgiA1
                                                         ∧
                                            >ApaL1       |
                                              ∧          |
     4760       4770       4780       4790   |    4800       4810       4820
   *    *    *    *    *    *    *    *   v *  v *    *    *    *    *
GTATCTCAGT TCGGTGTAGG TCGTTCGCTC CAAGCTGGGC TGTGTGCACG AACCCCCCGT TCAGCCCGAC
CATAGAGTCA AGCCACATCC AGCAAGCGAG GTTCGACCCG ACACACGTGC TTGGGGGGCA AGTCGGGCTG

>NspB2                                  >Ple1
  ∧                                       ∧
  |    4830       4840       4850       4860       4870       4880       4890
  v *    *    *    *    *    *    *    v *    *    *    *    *    *
CGCTGCGCCT TATCCGGTAA CTATCGTCTT GAGTCCAACC CGGTAAGACA CGACTTATCG CCACTGGCAG
GCGACGCGGA ATAGGCCATT GATAGCAGAA CTCAGGTTGG GCCATTCTGT GCTGAATAGC GGTGACCGTC

>AlwN1
       ∧
       |    4900       4910       4920       4930       4940       4950       4960
     * v *    *    *    *    *    *    *    *    *    *    *    *    *
CAGCCACTGG TAACAGGATT AGCAGAGCGA GGTATGTAGG CGGTGCTACA GAGTTCTTGA AGTGGTGGCC
GTCGGTGACC ATTGTCCTAA TCGTCTCGCT CCATACATCC GCCACGATGT CTCAAGAACT TCACCACCGG 4970       4980       4990       5000       5010       5020       5030
   *    *    *    *    *    *    *    *    *    *    *    *    *    *
TAACTACGGC TACACTAGAA GGACAGTATT TGGTATCTGC GCTCTGCTGA AGCCAGTTAC CTTCGGAAAA
ATTGATGCCG ATGTGATCTT CCTGTCATAA ACCATAGACG CGAGACGACT TCGGTCAATG GAAGCCTTTT 5040       5050       5060       5070       5080       5090       5100
   *    *    *    *    *    *    * v *    *    *    *    *    *    *
AGAGTTGGTA GCTCTTGATC CGGCAAACAA ACCACCGCTG GTAGCGGTGG TTTTTTTGTT TGCAAGCAGC
TCTCAACCAT CGAGAACTAG GCCGTTTGTT TGGTGGCGAC CATCGCCACC AAAAAAACAA ACGTTCGTCG

>Xho2       >BstY1
                ∧           ∧
             >BstY1       >Xho2
                ∧           ∧                                         >Hga1
                                                                        ∧
     5110       5120 |    5130 |    5140       5150       5160       5170
   *    *    *    * v *    * v *    *    *    *    *    *    *    * v *
AGATTACGCG CAGAAAAAAA GGATCTCAAG AAGATCCTTT GATCTTTTCT ACGGGGTCTG ACGCTCAGTG
TCTAATGCGC GTCTTTTTTT CCTAGAGTTC TTCTAGGAAA CTAGAAAAGA TGCCCCAGAC TGCGAGTCAC

>BstY1
                                         ∧           >BstY1   >Dra1
                                       >Xho2           ∧       ∧
         Mae2           >BspH1         >Hph1 ∧       >Xho2   >Aha3
           ∧              ∧              ∧ |           ∧       ∧
     5180 |    5190       5200       5210 |    5220       5230       5240
   *    * v *    *    *    *    *    * v v *    *    *    *    * v *
GAACGAAAAC TCACGTTAAG GGATTTTGGT CATGAGATTA TCAAAAAGGA TCTTCACCTA GATCCTTTTA
CTTGCTTTTG AGTGCAATTC CCTAAAACCA GTACTCTAAT AGTTTTTCCT AGAAGTGGAT CTAGGAAAAT

>Dra1
         ∧
       >Aha3
         ∧
     5250       5260       5270       5280       5290       5300       5310
   *    *    * v *    *    *    *    *    *    *    *    *    *    *
AATTAAAAAT GAAGTTTTAA ATCAATCTAA AGTATATATG AGTAAACTTG GTCTGACAGT TACCAATGCT
TTAATTTTTA CTTCAAAATT TAGTTAGATT TCATATATAC TCATTTGAAC CAGACTGTCA ATGGTTACGA

>Ban1                                        >Ple1
         ∧                                            ∧
     5320 |    5330       5340       5350       5360 |    5370       5380
   *    * v *    *    *    *    *    *    *    *    * v *    *    *
TAATCAGTGA GGCACCTATC TCAGCGATCT GTCTATTTCG TTCATCCATA GTTGCCTGAC TCCCCGTCGT
ATTAGTCACT CCGTGGATAG AGTCGCTAGA CAGATAAAGC AAGTAGGTAT CAACGGACTG AGGGGCAGCA
```

TABLE 6-continued

```
                                                                              >Hph1
                                                                               ʌ
       5390       5400       5410       5420       5430       5440    |    5450
     *  *      *  *       *  *       *  *       *  *       *  *    v  *
GTAGATAACT ACGATACGGG AGGGCTTACC ATCTGGCCCC AGTGCTGCAA TGATACCGCG AGACCCACGC
CATCTATTGA TGCTATGCCC TCCCGAATGG TAGACCGGGG TCACGACGTT ACTATGGCGC TCTGGGTGCG

>Cfr10I                                         >Bgl1
 ʌ                                               ʌ
 |     5460       5470       5480       5490   |   5500       5510       5520
v  *       *  *       *  *       *  *       v  *       *  *       *  *
TCACCGGCTC CAGATTTATC AGCAATAAAC CAGCCAGCCG GAAGGGCCGA GCGCAGAAGT GGTCCTGCAA
AGTGGCCGAG GTCTAAATAG TCGTTATTTG GTCGGTCGGC CTTCCCGGCT CGCGTCTTCA CCAGGACGTT

>Ase1
                        ʌ
       5530       5540 |   5550       5560       5570       5580       5590
     *  *       *  *       *  *       *  *       *  *       *  *       *  *
C TTTATCCGC CTCCATCCAG TCTATTAATT GTTGCCGGGA AGCTAGAGTA AGTAGTTCGC CAGTTAATAG
GAAATAGGCG GAGGTAGGTC AGATAATTAA CAACGGCCCT TCGATCTCAT TCATCAAGCG GTCAATTATC

>Mae2
   >Aos1        ʌ
    ʌ
   >Fsp1
    ʌ
   >Fdi2
    ʌ
   >Mst1             >Pst1
    ʌ                 ʌ
    |   5600       5610       5620       5630       5640       5650       5660
    * v *       *  v  *       *  *       *  *       *  *       *  *       *  *
TTTGCGCAAC GTTGTTGCCA TTGCTGCAGG CATCGTGGTG TCACGCTCGT CGTTTCCTAT GGCTTCATTC
AAACGCGTTG CAACAACGGT AACGACGTCC GTAGCACCAC AGTGCGAGCA GCAAACCATA CCGAAGTAAG 5670       5680       5690       5700       5710       5720       5730
     *  *       *  *       *  *       *  *       *  *       *  *       *  *
AGCTCCGGTT CCCAACGATC AAGGCGAGTT ACATGATCCC CCATGTTGTG CAAAAAAGCG GTTAGCTCCT
TCGAGGCCAA GGGTTGCTAG TTCCGCTCAA TGTACTAGGG GGTACAACAC GTTTTTTCGC CAATCGAGGA

>Pvu1          >Eae1
             ʌ              ʌ
            >Xor2          >Cfr1
             ʌ              ʌ
       5740 |   5750       5760 |   5770       5780       5790       5800
     *  *       v  *       *  *       v       *  *       *  *       *  *
TCGGTCCTCC GATCGTTGTC AGAAGTAAGT TGGCCGCAGT GTTATCACTC ATGGTTATGG CAGCACTGCA
AGCCAGGAGG CTAGCAACAG TCTTCATTCA ACCGGCGTCA CAATAGTGAG TACCAATACC GTCGTGACGT

>Rsa1
                                                           ʌ
                                                          >Sca1       >Hph1
                                                           ʌ           ʌ
       5810       5820       5830       5840       5850  |   5860     |   5870
     *  *       *  *       *  *       *  *       *  *       v  *    v *   *  *
TAATTCTCTT ACTGTCATGC CATCCGTAAG ATGCTTTTCT GTGACTGGTG AGTACTCAAC CAAGTCATTC
ATTAAGAGAA TGACAGTACG GTAGGCATTC TACGAAAAGA CACTGACCAC TCATGAGTTG GTTCAGTAAG

>Hinc2
                                              ʌ
                                             >Hind2
                                              ʌ
                                    >Acy1
                                     ʌ
                       >Hga1        >Aha2
                        ʌ            ʌ
       5880       5890       5900       5910       |   5920       5930       5940
     *  *       *  *       *  *       v  *       v*       *  *       *  *       *  *
TGAGAATAGT GTATGCGGCG ACCGAGTTGC TCTTGCCCGG CGTCAACACG GGATAATACC GCGCCACATA
ACTCTTATCA CATACGCCGC TGGCTCAACG AGAACGGGCC GCAGTTGTGC CCTATTATGG CGCGGTGTAT
```

TABLE 6-continued

```
                    >Asp700
                    ∧
  >Aha3             >Mae2                        >BetY1
  ∧                 ∧                            ∧
  >Dra1    >HgiA1   >Xmn1                        >Xho2        >NspB2
  ∧        ∧        ∧                            ∧            ∧
  5950     5960     5970   |   5980     5990     6000         6010
  *    *   *    v* *    *  v *    *     *    *   *    v*      *   v *
```
GCAGAACTTT AAAAGTGCTC ATCATTGGAA AACGTTCTTC GGGGCGAAAA CTCTCAAGGA TCTTACCGCT
CGTCTTGAAA TTTTCACGAG TAGTAACCTT TTGCAAGAAG CCCCGCTTTT GAGAGTTCCT AGAATGGCGA

```
  >Xho2                     >HgiA1
  ∧                         ∧
  >BstY1            >ApaL1  |              >Hph1
  ∧                 ∧                      ∧
  |  6020    6030   6040    |  6050   6060 |  6070     6080
  *    *   *    *   *    * v*   *    *   *   *    *     *    *
```
GTTGAGATCC AGTTCGATGT AACCCACTCG TGCACCCAAC TGATCTTCAG CATCTTTTAC TTTCACCAGC
CAACTCTAGG TCAAGCTACA TTGGGTGAGC ACGTGGGTTG ACTAGAAGTC GTAGAAAATG AAAGTGGTCG

```
            >Hph1
            ∧
  6090      6100     6110     6120     6130     6140      6150
  *    *    *    *   *    *   *    *   *    *   *    *    *    *
```
GTTTCTGGGT GAGCAAAAAC AGGAAGGCAA AATGCCGCAA AAAAGGGAAT AAGGGCGACA CGGAAATGTT
CAAAGACCCA CTCGTTTTTG TCCTTCCGTT TTACGGCGTT TTTTCCCTTA TTCCCGCTGT GCCTTTACAA

```
                              >Sep1                       >BspH1
                              ∧                           ∧
  6160      6170     6180     6190     6200     6210      6220
  *    *    *    *   *    v*  *    *   *    *   *    *v   *    *
```
GAATACTCAT ACTCTTCCTT TTTCAATAT T ATTGAAGCAT TTATCAGGGT TATTGTCTCA TGAGCGGATA
CTTATGAGTA TGAGAAGGAA AAAGTTATAA TAACTTCGTA AATAGTCCCA ATAACAGAGT ACTCGCCTAT

```
  6230      6240     6250     6260     6270     6280      6290
  *    *    *    *   *    *   *    *   *    *   *    *    *    *
```
CATATTTGAA TGTATTTAGA AAAATAAACA AATAGGGGTT CCGCGCACAT TTCCCCGAAA AGTGCCACCT
GTATAAACTT ACATAAATCT TTT2ATTTGT TTATCCCCAAGGCGCGTGTA AAGGGGCTTT TCACGGTGGA

```
              >Aat2
  >Aha2       ∧                                           >Pss1
  ∧                                                       ∧
  >Acy1                                         >Eco0109I
  ∧                                             ∧         |
  >Hae2                >BspH1                   >Dra2
  ∧                    ∧                        ∧
  |   |  6300   6310 | 6320     6330     6340   6350     6360
  v   *    *   *   v* *    *   *    *   *    *  *   v*   *   *
```
GACGTCTAAG AAACCATTAT TATCATGACA TTAACCTATA AAAATAGGCG TATCACGAGG CCCTTTCGTC
CTGCAGATTC TTTGGTAATA ATAGTACTGT AATTGGATAT TTTTATCCGC ATAGTGCTCC GGGAAAGCAG

*
TTCAA
AAGTT zymes which do not cut LXSNRIIL2:

| Acc3 | Bgl2  | Cla1    | Hpa1 | Nru1  | SnaB1 |
| Apa1 | Bsm1  | Dra3    | Mlu1 | PflM1 | Spl1  |
| Asu2 | BspM2 | Eco47III| Mro1 | Sac2  | Sst2  |
| Ban3 | BstB1 | Esp1    | Not1 | Sal1  |       |

To generate the LXSN-RI-IL2 retroviral vector, 10 micrograms of pLXSN-RI-IL2 DNA was transfected into the ecotropic packaging cell line PE501 by standard calcium phosphate precipitation methods (Miller et al., Mol. Cell Biol. 6:2895, 1986). The transfected PE501 cell line was grown in DMEM medium with 10% FCS. The medium was changed after 24 hours and supernatant harvested 24 hours later to infect the amphotropic packaging cell line PA317 as described (Miller et al., Mol. Cell Biol. 6:2895, 1986 and Miller et al., BioTechniques 7:980, 1989). The infected PA317 cells were harvested by trypsinization 24 hours later and replated 1:20 in DMEM containing 10% FCS and the neomycin analogue G418 (400 µg/ml). The cells were grown at 37° C. in 7% $CO_2$ atmosphere. The selection medium was changed every 5 days until colonies appeared. On day 14, twenty colonies were selected, expanded and tested for viral production by standard methods (Xu et al., Virology 171:331-341, 1989). Briefly, supernatants were harvested from confluent culture dishes, passed through a 0.45 µm filter, diluted with DMEM with 10% FCS and utilized to infect NIH 3T3 cells in the presence of 8 µg/ml polybrene. After 24 hours, the infected NIH 3T3 cells were grown in culture medium that contained the neomycin analogue G418. After 12–14 days, the colonies were stained, counted and the viral titer calculated as described (Xu et al., Virology 171:331–341, 1989).

Colonies with the highest viral titers (>10⁴ infectious units/ml) were tested for IL-2 expression by Northern blot analyses. Colonies with the highest viral titers and documented IL-2 expression were cryopreserved and will be utilized as stock cultures to produce the LXSN-RI-IL2 retroviral vector trial.

EXAMPLE IV

Retroviral Vector Construction and Cytokine Expression

To increase IL-2 production by transduced cell lines, vectors were used containing different promoters to drive IL-2 expression, and a human IL-2 cDNA was directionally sub-cloned into the insulin secretory signal peptide (17). The IL-2 cDNA was directionally sub-cloned into the parental plasmids of the LXSN (LTR promoter) and LNCX (CMV promoter) vectors (gifts of Dr. A. D. Miller) (18). The newly constructed vectors (FIG. 1), designated as LXSN-IL2 and LNCX-IL2, were packaged in the PA317 cell line for production of retroviral supernatant. As a control, the high level expressing, double copy vector DC/TKIL-2 vector (thymidine kinase promoter) (a gift of Dr. E. Gilboa) was used for comparison.

These vectors were used to transduce a number of murine and human, primary and established cell lines. Pools of transduced cells were selected and expanded in DMEM medium, containing 10% fetal bovine serum (FBS) and 400 µg/ml of active G-418, a neomycin analogue. The results of expression studies in the MCR9 and Balb/c 3T3 cell lines are presented in Table 7.

TABLE 7

Comparison of IL-2 expression by fibroblasts transduced with different IL-2 vectors.

| Fibroblast | Vector | ng IL-2 per 10⁶ cells per day | Units IL-2 per 10⁶ cells per day |
|---|---|---|---|
| Murine | LNCX (Control) | 0.4 ± 50% | <1 |
|  | LNCX-IL2 | 33.7 ± 11% | 67 |
|  | LXSN-IL2 | 6.6 ± 6% | 13 |
|  | DC/TKIL-2 | 1.9 ± 5% | 4 |
| Human | LXSN (Control) | 0.7 ± 29% | 1 |
|  | LNCX-IL-2 | 159.5 ± 17% | 319 |
|  | LXSN-IL2 | 25.5 ± 15% | 51 |
|  | DC/TKIL-2 | 3.0 ± 10% | 6 |

EXAMPLE V

Fibroblast Culture and Conditions for Retroviral Transduction

The culture conditions for the growth of primary fibroblasts retroviral transduction were optimized. Primary fibroblasts were successfully cultured. The optimal conditions enable the growth of approximately 3–4×10⁶ primary fibroblasts from a 12 mm² skin biopsy in approximately 4–6 weeks. Retroviral infection, G418 selection, and expansion of the genetically modified fibroblasts takes an additional 4–6 weeks.

Exploring the conditions for genetic modification of primary fibroblasts suggests that optimal transduction may be obtained by the following procedure: The fibroblasts are synchronized in G1 phase by serum starvation, followed by stimulation with medium containing 15% fetal bovine serum 15 hours prior to transduction. The cells are then subjected to 2 cycles of retrovirus infection, each cycle lasting approximately 3 hours. The cells are refed with fresh media overnight, and then selection in G418 is initiated the next day. This method is capable of transducing 5–15% of the fibroblasts in a culture, depending on the multiplicity of infection.

This procedure was used to transduce a large number of primary and established fibroblasts. As an example, Table 8 compares the expression levels of IL-2 in fibroblast lines transduced with LXSN-IL2.

TABLE 8

Expression of IL-2 by fibroblasts transduced with LXSN-IL2.

| Fibroblast Line | Species | Origin | ng IL-2 per 10⁶ cells per day | Units IL-2 per 10⁶ cells per day |
|---|---|---|---|---|
| Balb/c 3T3 | Murine | Transformed | 6.6 ± 6% | 13 |
| MCR9 | Human | Embryonic | 25.5 ± 15% | 51 |
| NHDF 313 | Human | Skin | 25.0 ± 10% | 50 |
| GT1 | Human | Skin | 15.0 ± 5% | 30 |

These results indicate that the IL-2 expression levels in established, embryonic, and primary fibroblast cultures are similar. Comparison of these data with Table 7 suggest that IL-2 expression is affected more by factors such as different promoters than by the fibroblast line used. Similarly, changes in culture conditions can have important effects on IL-2 expression. Table 9 shows that transduced GT1 cells, a primary human fibroblast culture expressed 15-fold more IL-2 under 100 µg/ml G418 selection than under 25 µg/ml G418 selection. Several other primary fibroblast lines have also been transduced with our vectors and are currently growing under G418 selection.

TABLE 9

Effect of G418 concentration on IL-2 expression by GT1 cells transduced with LXSN-IL2.

| Selection dose of G418 | ng IL-2 secreted per 10⁶ cells per day* |
|---|---|
| 25 µg/ml | 1.0 ± 10% |
| 50 µg/ml | 3.0 ± 6% |
| 100 µg/ml | 15.0 ± 5% |

*After three weeks of G418 selection.

EXAMPLE VI

Comparison of IL-2 Expression Levels Induced Peripheral Blood Lymphocytes and Genetically Modified Fibroblasts In order to compare the production of IL-2 by genetically modified fibroblasts to that achieved by stimulating normal human peripheral blood lymphocytes (nPBL) in vitro, nPBL were isolated by Ficol-Paque density centrifugation, and cultured in the presence of allogeneic nPBL (mixed lymphocyte culture, MLC) or 2 µM calcium ionophore (CI) (A23187) free acid) plus 17 nM phorbol 12-myristate 13-acetate (PMA). The results of this experiment, present in Table 10, indicate that the level of IL-2 expression in the PMA/CI stimulated normal T cell population was 2 ng/10⁶ cells/24 hours. This is equivalent to IL-2 expression by Balb/c 3T3 fibroblasts transduced with DC/TKIL-2 (Table 7), our least productive vector. The level of IL-2 expression in the MLC was 130 pg/10⁶ cells/24 hours. This was lower than the PMA/CI stimulated culture, presumably because PMA/CI induced a nonspecific response while MLC resulted in specific Th stimulation. When the estimated percentage of antigen-specific Th in the MLC-stimulated population is taken into consideration, the level of IL-2 expression per stimulated T cell becomes equivalent for both methods.

TABLE 10

Levels of IL-2 secretion by different cells.

Figure 6:
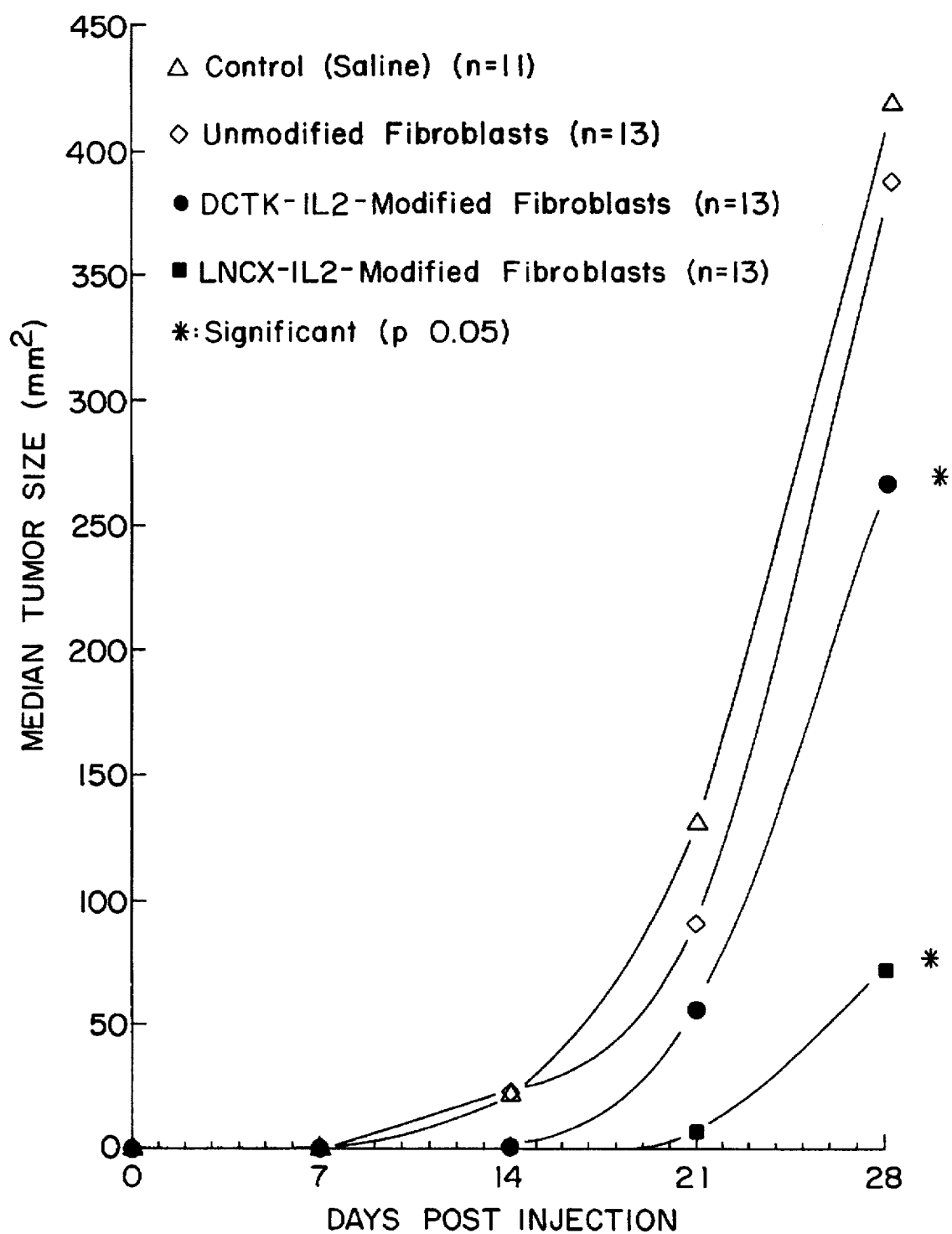
FIG. 6 shows the effect of IL-2 modified fibroblasts on tumor establishment and development using $2 \times 10^6$ fibroblasts mixed with $5 \times 10^4$ CT26 tumor cells concentrating on the rate of tumor growth.
Figure 7:
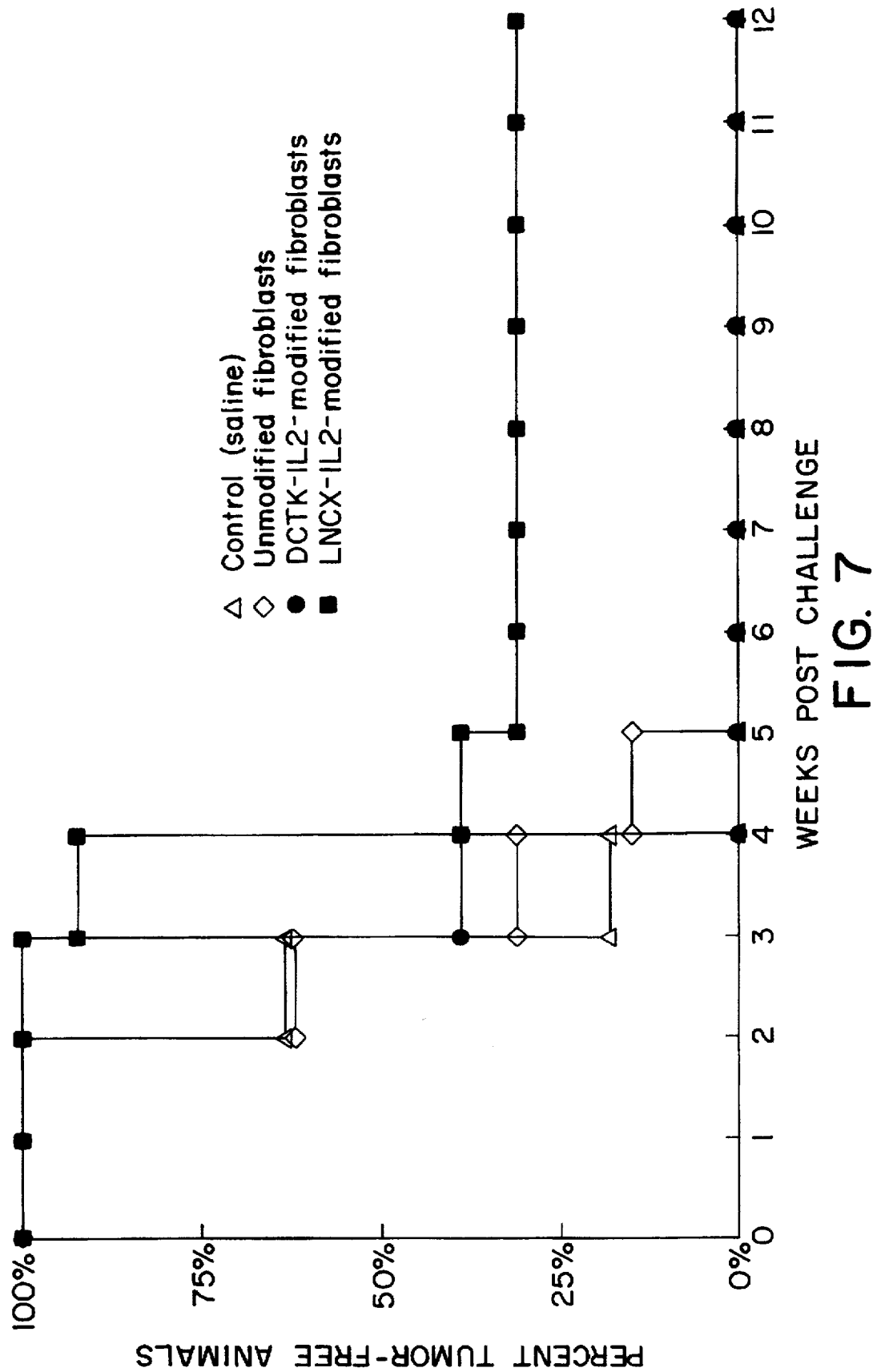
FIG. 7 shows the effect of IL-2 modified fibroblasts on tumor establishment and development using $2 \times 10^6$ fibroblasts mixed with $5 \times 10^4$ CT26 tumor cells concentrating on the time of tumor onset for the individual animal in each treatment group.

| Cells | pg IL-2 secreted per $10^6$ cells per day |
|---|---|
| Lymphocytes: | |
| Control (non-activated) | 5 ± 50% |
| PMA + Calcium Ionophore | 2,000 ± 6% |
| Mixed lymphocyte culture | 130 ± 90% |
| Transduced fibroblasts: | |
| MCR9-LXSN-IL2 | 24,000 ± 5% |
| MCR9-LNCX-IL2 | 162,000 ± 20% |
| MCR9-DC/TKIL-2 | 10,000 ± 6% | by different retroviral vectors to express IL-2. In the control arms injected with tumor cells only, or with tumor cells mixed with unmodified fibroblasts, 31 of 33 animals (94%) developed tumors by 4 weeks (FIGS. 6 and 7, Table 9). In contrast, 22 out of the 34 animals (65%) receiving fibroblast mediated cytokine gene therapy were tumor free at 3 weeks, and 5 animals (18%) remain tumor free after 12 weeks. Those animals that received fibroblast mediated IL-2 therapy and developed tumor were characterized by a delayed onset and rate of tumor growth.

TABLE 11

Effect of IL-2 modified fibroblasts on tumor establishment and development. $2 \times 10^6$ fibroblasts mixed with $5 \times 10^4$ CT26 tumor cells at time of injection.

| Fibroblasts mixed with tumor cells | Animal Number | | | | Tumor Size (mm$^2$) | | | | Median Tumor Size (mm$^2$) |
|---|---|---|---|---|---|---|---|---|---|
| | Total | Tumor-free | Tumor-bearing | Percent Tumor-free | 25–100 | 101–200 | 201–300 | >301 | |
| After 12 Weeks:* | | | | | | | | | |
| Control (no fibroblasts) | 11 | 0 | 11 | 0% | 1 | 0 | 1 | 9 | 420 ± 145 |
| Unmodified fibroblasts** | 13 | 2 | 11 | 15% | 1 | 0 | 1 | 7 | 389 ± 265 |
| DCTK-IL2 fibroblasts | 13 | 0 | 13 | 0% | 1 | 3 | 5 | 4 | 267 ± 168 |
| LNCX-IL2 fibroblasts | 13 | 5 | 8 | 39% | 5 | 2 | 0 | 1 | 72 ± 90 |

\* Mean tumor size is for 4 weeks, the last timepoint at which tumors were measured.
\*\*Two mice in this arm developed intraperitoneal tumors which were not measurable.

EXAMPLE VII

Fibroblast Mediated Cytokine Gene Therapy in Murine Tumor Models

Two experimental protocols were used to study the efficacy of fibroblast-mediated cytokine gene therapy on induction of anti-tumor immunity. The first protocol was designed to test the effects of genetically modified fibroblasts on tumor implantation, while the second protocol was designed to induce a systemic anti-tumor immunity. The results of each experiment are presented with two figures and one table. In the first figure, the rate of tumor growth for each treatment group is presented as the mean tumor size in the group over time. In the second figure, a Kaplan-Meier curve presents the time of tumor onset for the individual animals in each treatment group. The number of animals, the number and percentage of tumor free animals, and the tumor size distribution patterns for each experiment are presented in a table.

EXAMPLE VII

Effect of Fibroblast Mediated Cytokine Gene Therapy on Tumor Implantation

Mice were injected subcutaneously with mixtures of $5 \times 10^4$ CT26 cells and $2 \times 10^6$ fibroblasts genetically modified After 3 weeks the mean tumor size (measured as the product of the longest and widest tumor axes) in the control group of mice was 128 mm$^2$, compared to 68 and 7 mm$^2$ in groups of mice injected with tumor cells mixed with fibroblasts transduced with DC/TKIL-2 or LNCX-IL2, respectively. This resulted in a highly significant difference (corrected $x^2=18.69$, p=0.001) between the IL-2 treated animals compared to the mice treated with CT26 alone or CT26 mixed with unmodified fibroblasts. After four weeks the equivalent measurements were 373,300 and 72 mm$^2$ (Table 11). It is notable that LNCX-IL2, the highest expressing vector caused substantially greater inhibition of tumorigenicity than the lower expressing vector DC/TKIL-2. A multivariate non-parametric statistical procedure (19,20), utilized to evaluate differences in tumor growth, demonstrated that after 4 weeks the differences between the growth curves for the four groups presented in FIG. 2 were highly significant (p<0.001). Subsequent comparisons between the control arm and animals that received tumor cells mixed with IL-2 transduced fibroblasts revealed a significant difference (P<0.05). The differences between the animals injected with tumor cells alone, and those injected with tumor cells plus unmodified fibroblasts were not significant, while the differences between animals receiving low IL-2 expressing fibroblast, and those receiving high IL-2 expressing fibroblasts was significant (P=0.05).

Figure 8:
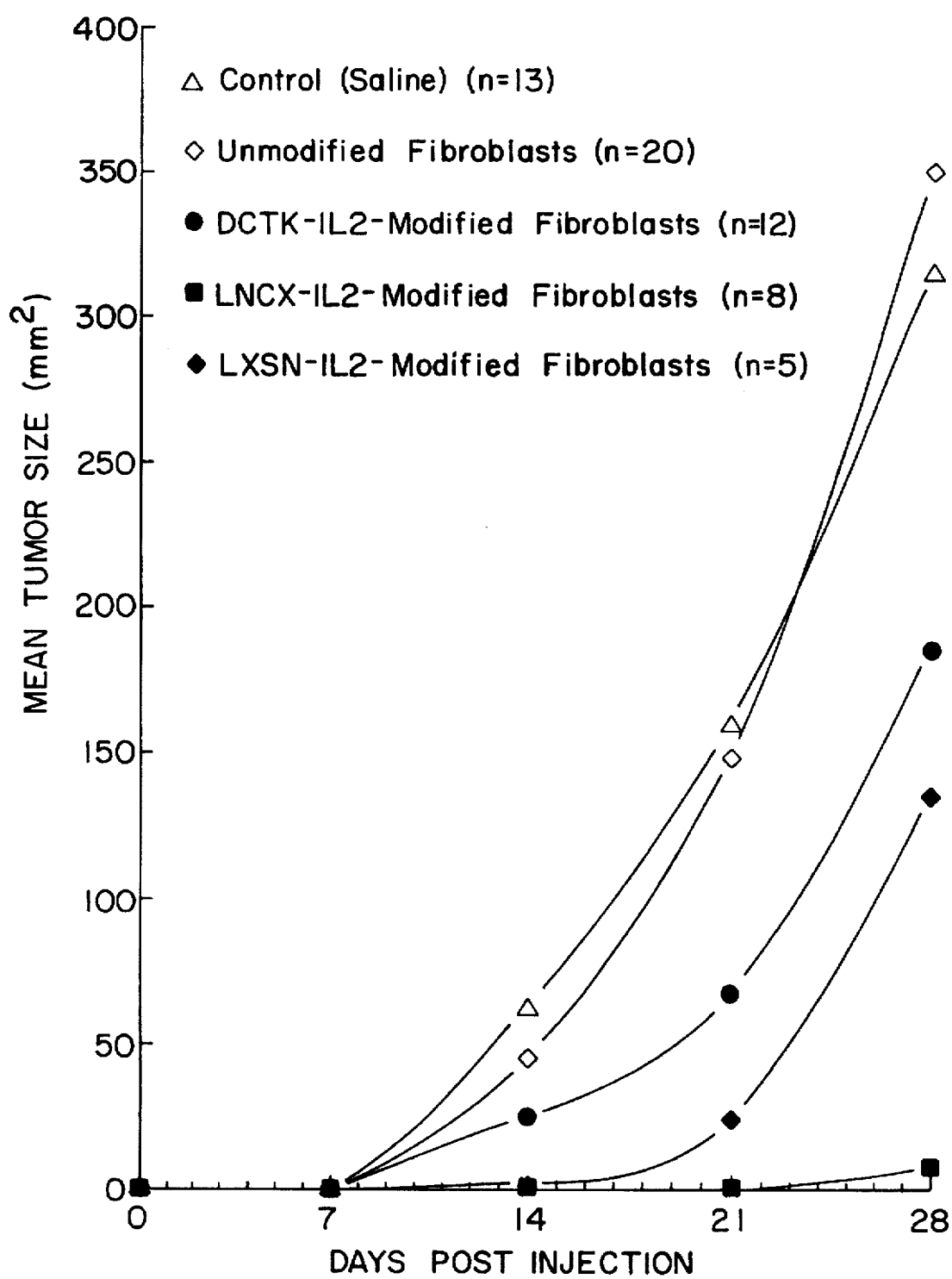
FIG. 8 shows the effect of IL-2 modified fibroblasts on tumor establishment and development using $2 \times 10^6$ fibroblasts mixed with $1 \times 10^5$ CT26 tumor cells concentrating on the rate of tumor growth.
Figure 9:
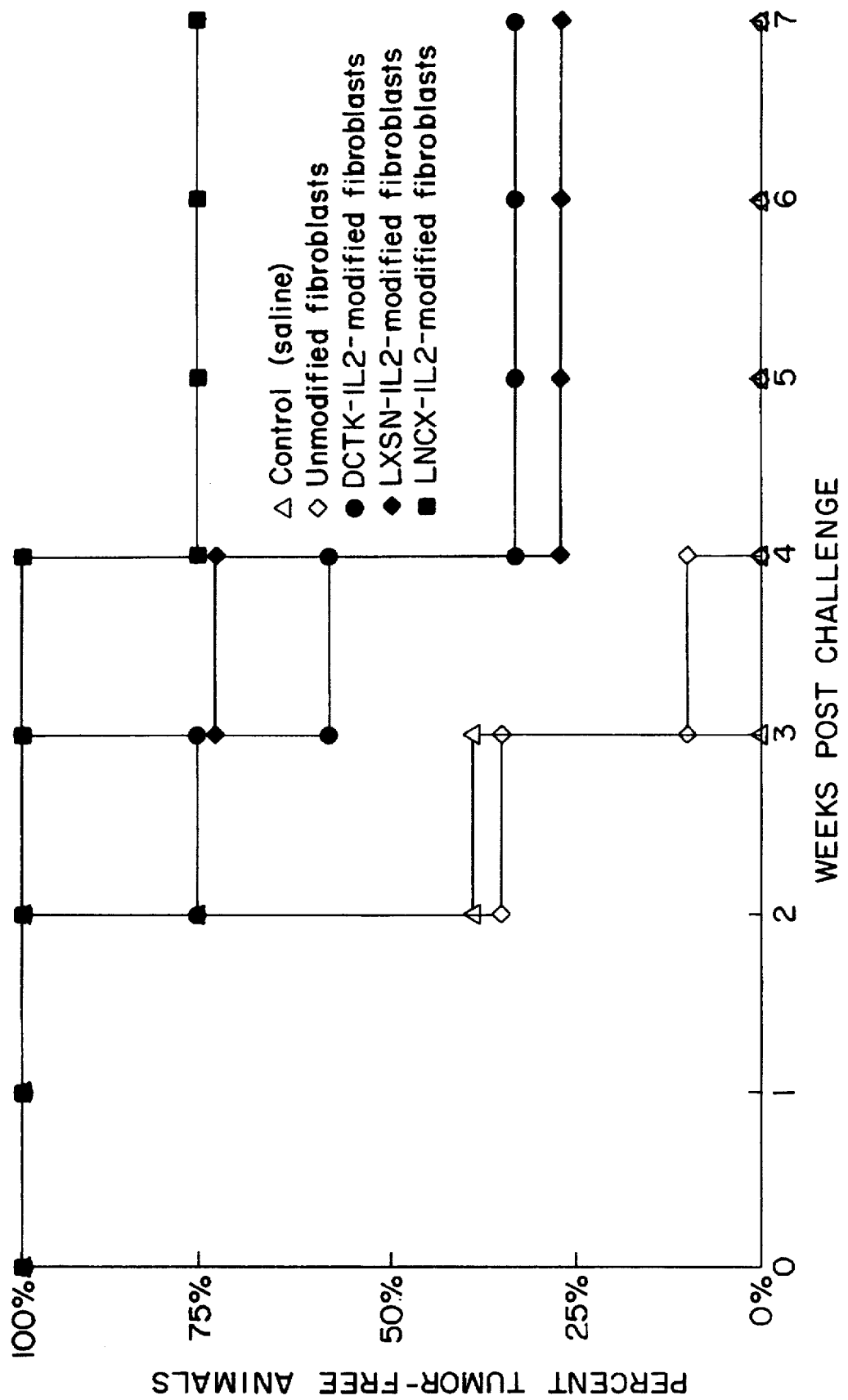
FIG. 9 shows the effect of IL-2 modified fibroblasts on tumor establishment and development using $2 \times 10^6$ fibroblasts mixed with $1 \times 10^5$ CT26 tumor cells concentrating on the time of tumor onset for the individual animal in each treatment group.

When mice were injected with $2 \times 10^6$ modified fibroblasts mixed with $1 \times 10^5$ live tumor cells the results became more striking (see FIGS. 8 and 9, and Table 12). All the control animals developed tumors after 4 weeks whereas 33% and 27% of the animals treated with fibroblasts modified with the DCTK-IL2 or LXSN-IL2 vectors (respectively) remain tumor free after 7 weeks (the experiment is ongoing). More dramatically, 75% of the animals treated with fibroblasts modified with the highest IL-2 producing vector, LNCX-IL2, remain tumor free after 7 weeks. These data clearly demonstrate the importance of an initial high dose of IL-2 to prevent tumor establishment.

arms. Data for animals treated under the same conditions with DCTK-IL2 modified fibroblasts in a separate experiment are included for comparison purposes. This comparison suggests that DCTK-IL2 modified tumor cells have an effect on tumor establishment similar to that of DCTK-IL2 modified fibroblasts.

TABLE 12

Effect of IL-2 modified fibroblasts on tumor establishment and development.
$2 \times 10^6$ fibroblasts mixed with $1 \times 10^5$ CT26 tumor cells at time of injection.

| Fibroblasts mixed with tumor cells | Animal Number | | | | Tumor Size ($mm^2$) | | | | Mean Tumor Size ($mm^2$) |
|---|---|---|---|---|---|---|---|---|---|
| | Total | Tumor-free | Tumor-bearing | Percent Tumor-free | 25–100 | 101–200 | 201–300 | >301 | |
| After 6 Weeks:* | | | | | | | | | |
| Control (no fibroblasts)** | 13 | 0 | 13 | 0% | 0 | 5 | 2 | 5 | 315 ± 197 |
| Unmodified fibroblasts** | 20 | 0 | 20 | 0% | 0 | 2 | 3 | 14 | 350 ± 100 |
| DCTK-IL2 fibroblasts | 12 | 4 | 8 | 33% | 0 | 1 | 4 | 3 | 185 ± 141 |
| LXSN-IL2 fibroblasts*** | 15 | 4 | 11 | 27% | 0 | 5 | 1 | 2 | 135 ± 121 |
| LNCX-IL2 fibroblasts | 8 | 6 | 2 | 75% | 2 | 0 | 0 | 0 | 8 ± 14 |

* Mean tumor size is for 4 weeks, the last timepoint at which tumors were measured.
**One mouse in each of these arms developed an intraperitoneal tumor which was not measurable.
***Three mice in this arm developed intraperitoneal tumors which were not measurable.

As an additional control, mice were injected with CT26 cells genetically modified to express IL-2 (results not shown). Injection of up to $1\times10^6$ IL-2 expressing tumor cells

TABLE 13

Effect of IL-2 modified cells on tumor establishment and developement.
$2 \times 10^6$ DCTK-IL2-modified CT26 tumor cells mixed with $1 \times 10^5$ CT26 cells compared to $2 \times 10^6$ DCTK-IL2-modified fibroblasts mixed with $1 \times 10^5$ CT26.

| Cells mixed with tumor cells | Animal Number | | | | Tumor Size ($mm^2$) | | | | Mean Tumor Size ($mm^2$) |
|---|---|---|---|---|---|---|---|---|---|
| | Total | Tumor-free | Tumor-bearing | Percent Tumor-free | 25–100 | 101–200 | 201–300 | >301 | |
| After 22 Weeks:* | | | | | | | | | |
| Control (no fibroblasts) | 5 | 0 | 5 | 0% | 0 | 0 | 0 | 5 | 620 ± 190 |
| Unmodified fibroblasts | 5 | 0 | 5 | 0% | 0 | 0 | 0 | 5 | 587 ± 69 |
| DCTK-IL2-modified CT26 cells | 10 | 1 | 9 | 10% | 1 | 0 | 2 | 5 | 303 ± 179 |
| DCTK-IL2-modified fibroblasts | 8 | 2 | 6 | 25% | 0 | 1 | 2 | 3 | 214 ± 158 |

Figure 10:
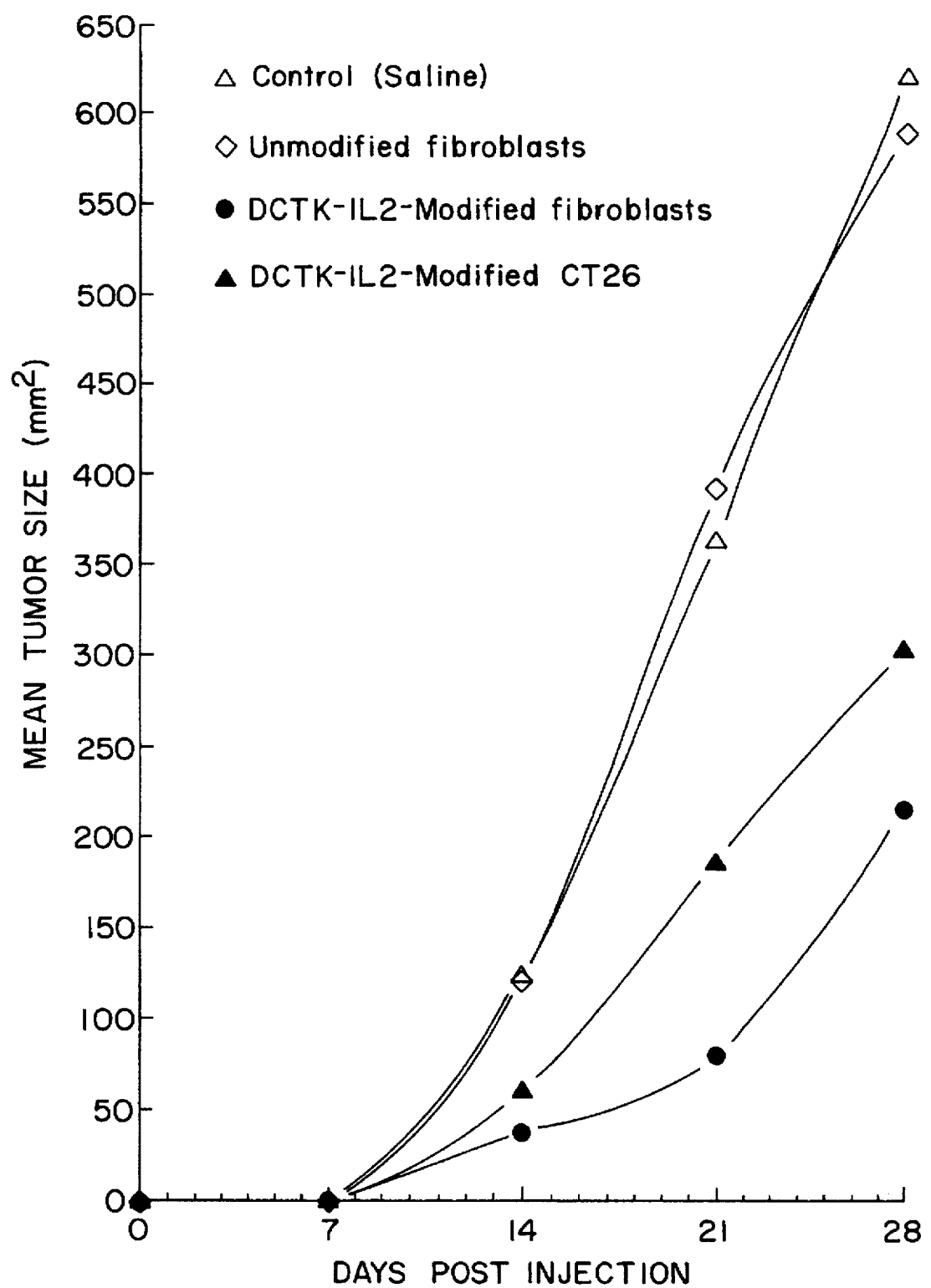
FIG. 10 shows the effect of IL-2 modified cells on tumor establishment and development using $2 \times 10^6$ DCTK-IL2-modified CT26 tumor cells mixed with $1 \times 10^5$ unmodified CT26 compared to $2 \times 10^6$ DCTK-IL2-modified fibroblasts mixed with $1 \times 10^5$ CT26 concentrating on the rate of tumor growth.
Figure 11:
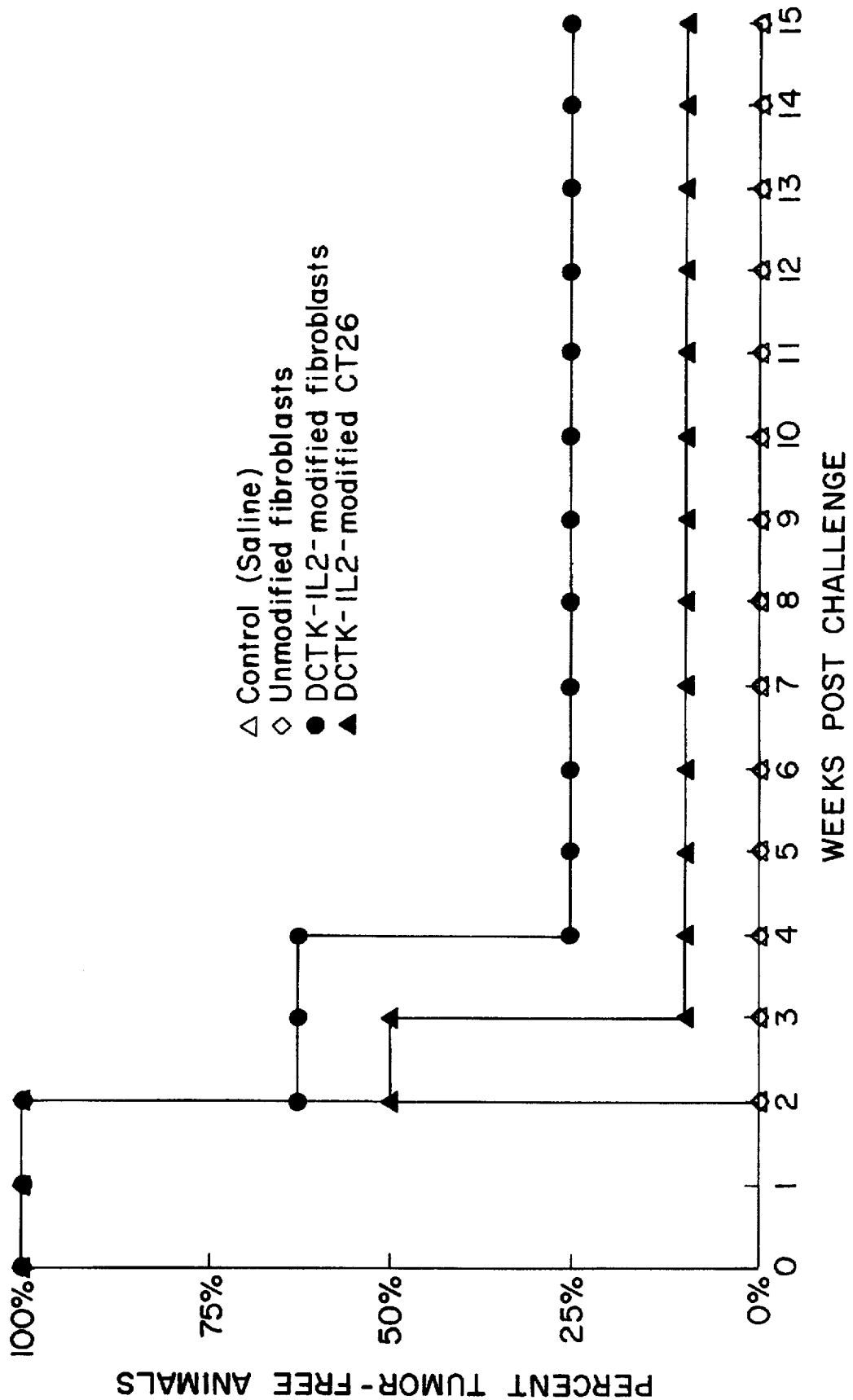
FIG. 11 shows the effect of IL-2 modified cells on tumor establishment and development using $2 \times 10^6$ DCTK-IL2-modified CT26 tumor cells mixed with $1 \times 10^5$ unmodified CT26 compared to $2 \times 10^6$ DCTK-IL2-modified fibroblasts mixed with $1 \times 10^5$ CT26 concentrating on the time of tumor onset for the individual animal in each treatment group.

*Mean tumor size is for 4 weeks, the last timepoint at which tumors were measured.

into Balb/c mice failed to produce tumors. Injection of higher numbers however, resulted in some animals developing tumors with delayed onset. These data confirm the results reported in the literature (1). In order to compare the efficacy of IL-2 producing fibroblasts to IL-2 producing tumor cells, we mixed $2\times10^6$ CT26 tumor cells modified with the DCTK-IL2 vector with $1\times10^5$ unmodified tumor cells. FIGS. 10 and 11, and Table 13 show that DCTK-IL2 modified tumor cells are somewhat effective in preventing tumor development. Four weeks after injection, the mean tumor size for the treatment arm is 303 $mm^2$, compared to 620 $mm^2$ for the control arm. After 22 weeks, one animal (10%) remains tumor free, compared to none in the control EXAMPLE VII(b)

Figure 12:
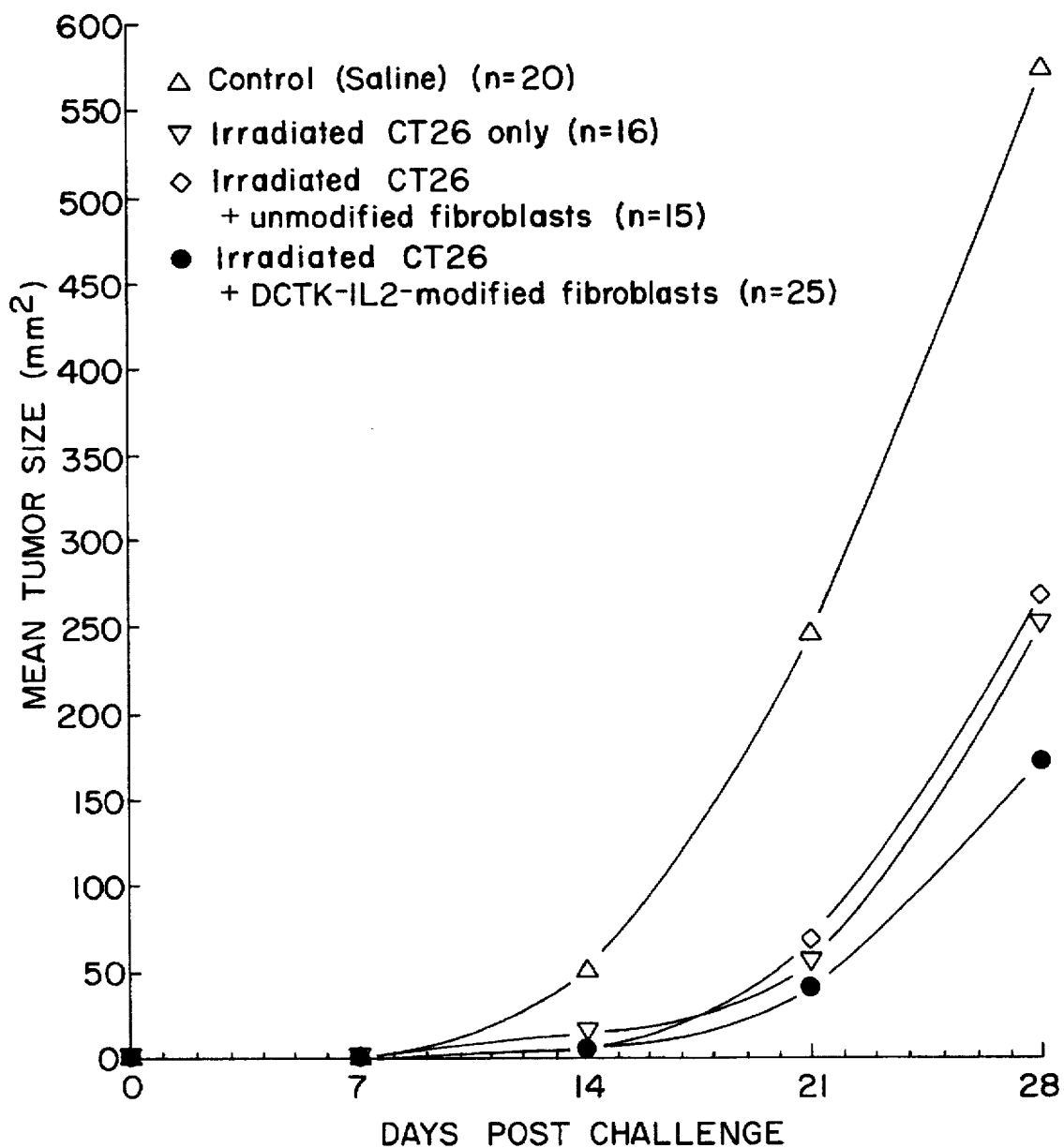
FIG. 12 shows the effect of IL-2 modified fibroblasts on induction of systemic anti-tumor immunity and the rate of tumor growth. Mice were immunized with $2 \times 10^6$ fibroblasts mixed with $2.5 \times 10^5$ irradiated CT26 tumor cells 7 days prior to challenge with $5 \times 10^4$ fresh tumor cells.
Figure 13:
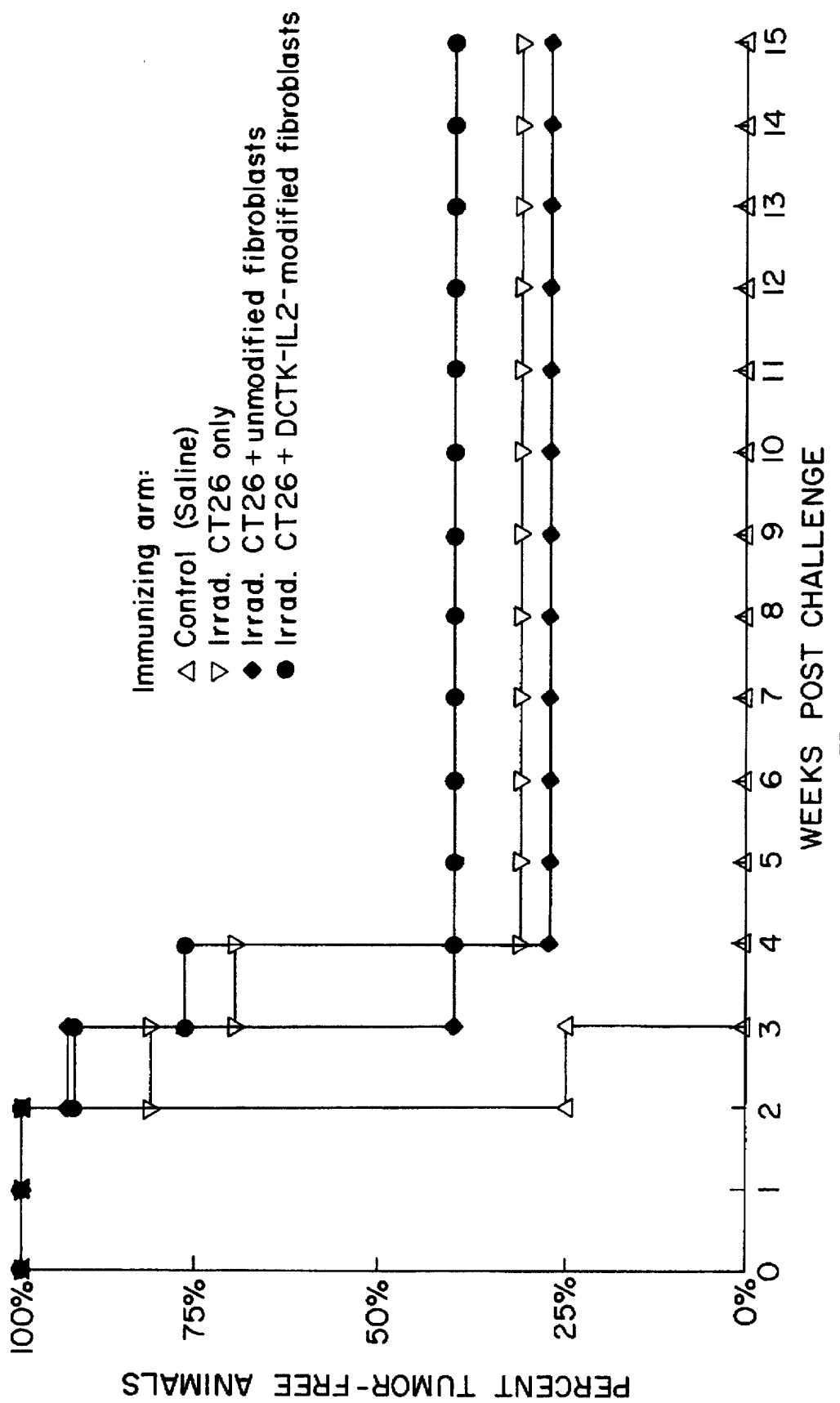
FIG. 13 shows the effect of IL-2 modified fibroblasts on induction of systemic anti-tumor immunity and the time of tumor onset for the individual animal in each treatment group. Mice were immunized with $2 \times 10^6$ fibroblasts mixed with $2.5 \times 10^5$ irradiated CT26 tumor cells 7 days prior to challenge with $5 \times 10^4$ fresh tumor cells.

Effect of Fibroblast Mediate Cytokine Gene Therapy on Systemic Anti-tumor Immunity Groups of Balb/c mice were immunized with $2.5\times10^5$ irradiated tumor cells either alone or mixed with $2\times10^6$ transduced or unmodified fibroblasts, and challenged one week later with $5\times10^4$ live tumor cells in the opposite flank. These results (FIGS. 12 and 13, and Table 14) demonstrate that immunization with irradiated tumor cells and transduced fibroblasts protect some animals against a live tumor challenge, but that the protection is only slightly better than that achieved by immunization with irradiated tumor cells alone or irradiated tumor cells mixed with unmodified fibroblasts.

size for the group at four weeks was 86 mm². The number of tumor free animals in the group treated with LXSN-IL2 modified fibroblasts was similar to the control groups,

TABLE 14

Effect of Il-2 modified fibroblasts on induction of sytemic anti-tumor immunity.
Mice immunized with 2 × 10⁶ fibroblasts mixed with 2.5 × 10⁵
irradiated CT26 tumor cells 7 days prior to challenge with 5 × 10⁴ fresh tumor cells.

| Fibroblasts mixed with irradiated tumor cells | Animal Number | | | Percent Tumor-free | Tumor Size (mm²) | | | | Mean Tumor Size (mm²) |
|---|---|---|---|---|---|---|---|---|---|
| | Total | Tumor-free | Tumor-bearing | | 25–100 | 101–200 | 201–300 | >301 | |
| After 22 Weeks:* | | | | | | | | | |
| Control (saline) | 20 | 0 | 20 | 0% | 0 | 0 | 1 | 19 | 574 ± 160 |
| Irradiated CT26 only** | 16 | 5 | 11 | 31% | 2 | 1 | 2 | 5 | 250 ± 277 |
| Irradiated CT26 mixed with unmodified fibroblasts | 15 | 4 | 11 | 27% | 0 | 1 | 3 | 7 | 266 ± 199 |
| DCTK-IL2 fibroblasts** | 25 | 10 | 15 | 40% | 4 | 1 | 1 | 8 | 172 ± 194 |

*Mean tumor size is for 4 weeks, the last timepoint at which tumors were measured.
** One mouse in each of these arms developed an intraperitoneal tumor which was not measurable.

Figure 14:
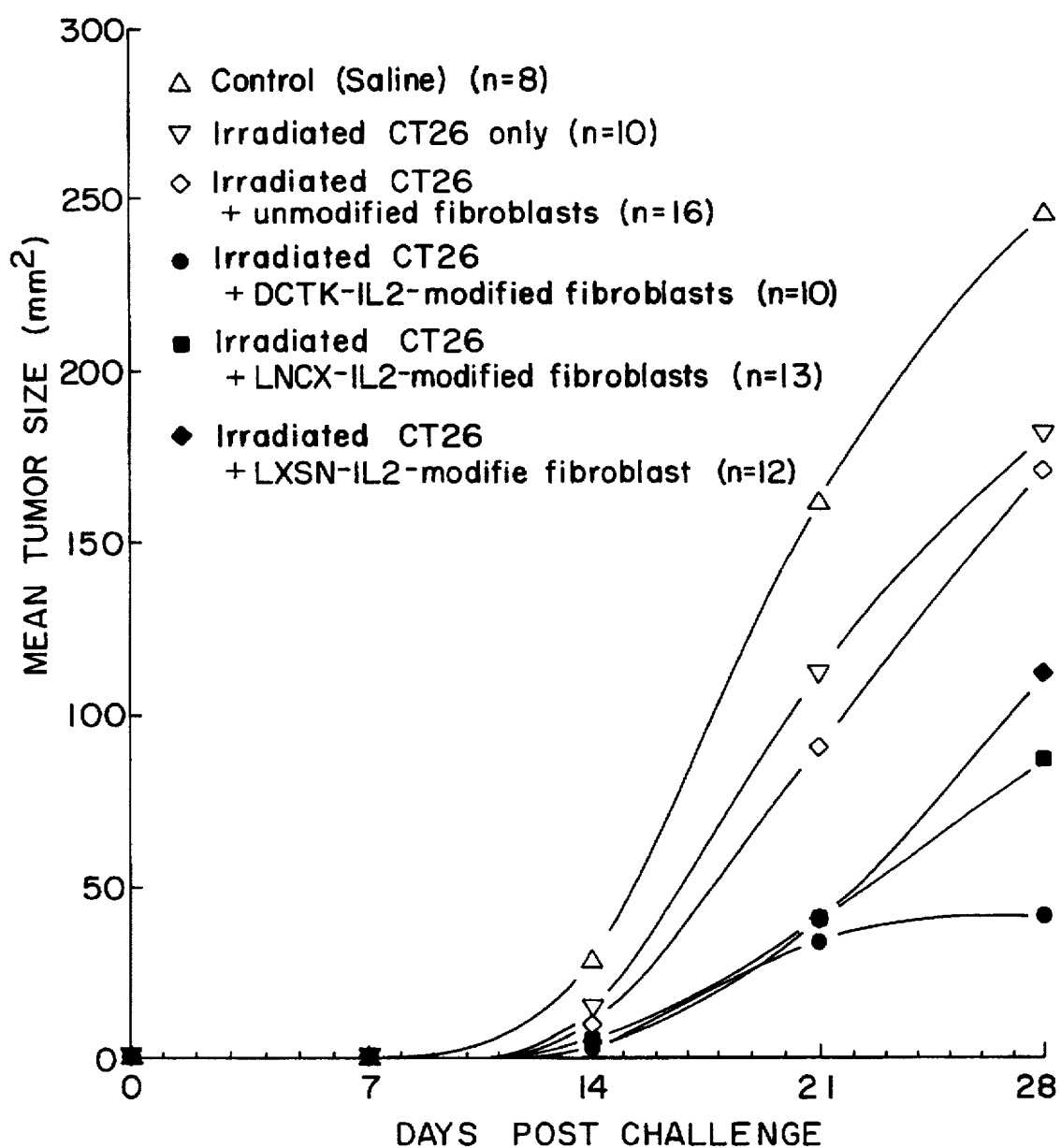
FIG. 14 shows the effect of IL-2 modified fibroblasts on induction of systemic anti-tumor immunity and the rate of tumor growth. Mice were immunized with $2 \times 10^6$ fibroblasts mixed with $2.5 \times 10^5$ irradiated CT26 tumor cells 14 days prior to challenge with $5 \times 10^4$ fresh tumor cells.

In a second protocol similar to the one described above, animals were challenged with fresh tumor cells two weeks following immunization with irradiated tumor cells mixed with fibroblasts. The results, shown in FIGS. 14 and 15, and in Table 15, demonstrate that DCTK-IL2 modified fibroblasts mixed with irradiated tumor cells confers superior protection to subsequent tumor challenge than irradiated tumor cells alone, irradiated tumor cells mixed with unmodified fibroblasts, or irradiated tumor cells mixed with LNCX-modified fibroblasts. After 7 weeks, seven of ten animals (70%) treated with DCTK-IL2 modified fibroblasts remain tumor free compared to only one third of the control animals. At four weeks, the mean tumor size of this group was 41 mm², compared to 180, 170, and 140 mm² for the three control groups. Animals treated with LNCX-IL2 modified fibroblasts were also protected against subsequent tumor challenge, but the results were less striking. In this group, 54% of the animals remain tumor free and the mean tumor although the tumors were slightly delayed in their onset. A multivariate non-parametric statistical procedure (19, 20), utilized to evaluate differences in tumor onset, demonstrated that the differences for the six arms presented in FIG. 15 were significant (p=0.012). It further showed that the saline control arm and the arms that received irradiated tumor cells alone or mixed with unmodified or LNCX vector modified fibroblasts formed a statistical group. A second, distinct statistical group was formed by the three arms that received IL-2 vector modified fibroblasts mixed with irradiated tumor cells. Subsequent comparisons between the saline injected control arm and animals that received tumor cells mixed with IL2 transduced fibroblasts revealed a significant difference for all vectors (p<0.05).

TABLE 15

Effect of IL-2 modified fibroblasts on induction of sytemic anti-tumor immunity.
Mice immunized with 2 × 10⁶ fibroblasts mixed with 2.5 × 10⁵
irradiated CT26 tumor cells 14 days prior to challenge with 5 × 10⁴ fresh tumor cells.

| Immunization by fibroblasts mixed with irradiated tumor cells | Animal Number | | | Percent Tumor-free | Tumor Size (mm²) | | | | Mean Tumor Size (mm²) |
|---|---|---|---|---|---|---|---|---|---|
| | Total | Tumor-free | Tumor-bearing | | 25–100 | 101–200 | 201–300 | >301 | |
| After 7 Weeks:* | | | | | | | | | |
| Control (saline)** | 8 | 1 | 7 | 13% | 0 | 2 | 1 | 3 | 245 ± 173 |
| Irradiated CT26 only | 10 | 3 | 7 | 30% | 0 | 2 | 4 | 1 | 180 ± 155 |
| Irradiated CT26 mixed with unmodified fibroblasts | 6 | 2 | 4 | 33% | 0 | 2 | 1 | 1 | 170 ± 160 |
| Irradiated CT26 mixed with LNCX-modified fibroblasts | 10 | 3 | 7 | 30% | 3 | 0 | 1 | 3 | 140 ± 142 |
| Irradiated CT26 mixed with LNCX-IL2-modified fibroblasts | 13 | 7 | 6 | 54% | 1 | 3 | 1 | 1 | 86 ± 112 |
| Irradiated CT26 mixed with LXSN-IL2-modified fibroblasts | 12 | 4 | 8 | 33% | 5 | 0 | 2 | 1 | 111 ± 145 |
| Irradiated CT26 mixed with DCTX-IL2-modified fibroblasts | 10 | 7 | 3 | 70% | 1 | 2 | 0 | 0 | 41 ± 75 |

*Mean tumor size is for 4 weeks, the last timepoint at which tumors were measured.
**One mouse in this arm developed an intraperitoneal tumor which was not measurable.

These results demonstrate the feasibility of using genetically modified fibroblasts as a means of delivering cytokine gene therapy. In all experiments, the LNCX-L2 vector proved superior in preventing tumor establishment while the DCTK-IL2 vector was better in the induction of systemic protection against subsequent tumor challenges. These contrasting effects, although somewhat surprising, can be explained by the observation that the CMV promoter is turned off in vivo five days after implantation while the TK promoter remains active for a longer period of time. The implication of this finding is that to apply this method of gene therapy successfully we have to use promoters that result in high level, sustained expression of IL-2 in vivo in the transduced fibroblasts.

The data obtained from this research effort has important implications for all cytokines that have either direct or indirect anti-tumor effects. Furthermore, this data suggests that anti-tumor efficacy is IL-2 dose dependent. Hence, construction of vectors which result in higher levels of cytokine secretion will be a significant advance toward the application of this method of gene therapy.

Reference numbers in parenthesis in the above examples correspond to the following list of references and are incorporated herein by reference.

References

1. Gabrilove, J. L. et al., Monogr. J. Natl. Cancer Inst. 10:73–7 (1990).

2. Kelso, A., Current Opinion in Immunology, 2:215–25 (1989).

3. Borden, E. C. et al., Cancer, 65:800–14 (1990).

4. Rosenberg, S. A. et al., Ann. Intern. Med., 108:853–864 (1988).

5. Lotze, M. T. et al., JAMA, 256:3117–3124 (1986).

6. Pizza, G. et al., Lymphokine Research, 7:45–8 (1988).

7. Sarna, G. et al., Journal of Biological Response Modifiers, 9:81–6 (1990).

8. Gandolfi, L. et al., Hepato-Gastroenterology, 36:352–6 (1989).

9. Bubenik, J. et al., Immunol. Letters, 19:279–82 (1988).

10. Bubenik et al., Immunol. Letters, 23:287–292 (1990).

11. Fearon, E. R. et al., Cell, 60:387–403 (1990).

12. Gansbacher, B. et al., J. Exp. Med., 172:1217–1224 (1990).

13. Watanabe, Y. et al., Proc. Natl. Acad. Sci., 86:9456–9460 (1989).

14. Tepper, R. I. et al., Cell, 57:503–512 (1989).

15. Kriegler, M., Gene Transfer and Expression: A Laboratory Manual, Stockton Press (1990).

16. Rosenberg, S. A. et al., N. Eng. J. Med., 370 (1990).

17. Cornetta, K. et al., Prog. Nucl. Acid Res. Mol. Biol., 36:311–22 (1989).

18. Hoover, H. C. et al., Cancer Res., 44:1671–76 (1984).

19. Sobol et al. New Eng. J. Med. 316:1111–1117 (1987).

20. Li Xu, et al., Virology, 171:331–341 (1989).

Although the invention has been described with reference to the presently-preferred embodiment, it should be understood that various modifications can be made without departing from the spirit of the invention. Accordingly, the invention is limited only by the following claims.

---

We claim:

1. A method of inhibiting or preventing the growth of tumor cells in a patient comprising the stimulation of that patient's immune response against the tumor cells by administering to said patient at a site other than an active tumor site a composition comprising tumor antigens and cytokine-expressing cells genetically modified to express a cytokine gene product, wherein said cytokine-expressing cells are not tumor cells, and wherein said administering stimulates a systemic active immune response in said patient, and wherein said systemic active immune response results in inhibition of growth of said tumor cells.

2. The method of claim 1 wherein tumor cells previously isolated from said patient provide the tumor antigens.

3. The method of claim 1 wherein the cytokine gene product is selected from the group consisting of interleukin-1, interleukin-2, interleukin-3, interleukin-4, interleukin-5, interleukin-6, and gamma-interferon.

4. The method of claim 1 wherein the cytokine gene product is interleukin-2.

5. The method of claim 1, wherein said cytokine-expressing cells are genetically modified to express a cytokine gene product by recombinant methods.

6. The method of claim 5 wherein the cytokine gene is present in an expression vector.

7. The method of claim 6 wherein said expression vector additionally contains a suicide gene.

8. The method of claim 5 wherein the cytokine-expressing cells are generated from fibroblasts and antigen-presenting cells.

9. A method for enhancing a patient's systemic active immune response to a tumor, comprising the steps of:
 a. isolating fibroblasts from said patient;
 b. culturing said fibroblasts in vitro;
 c. transducing said fibroblasts with a retroviral expression vector containing the gene coding for IL-2, wherein said IL-2 is expressed and secreted by said transduced fibroblasts;
 d. isolating tumor cells from said patient;
 e. preparing a single-cell suspension of the tumor cells;
 f. treating the tumor cells with an agent which inhibits the ability of the tumor cells to proliferate; and
 g. administering to said patient said treated tumor cells and said fibroblasts, which express IL-2 at a level sufficient to enhance the systemic active immune response in said patient but low enough to avoid substantial systemic toxicity, and wherein said treated tumor cells and said fibroblasts are at a site other than an active tumor site.

10. The method of claim 9 wherein said fibroblasts are further modified to express a suicide gene.

11. A composition for increasing a patient's immune response to tumor antigens comprising tumor antigens and cytokine-expressing cells genetically modified to express a cytokine gene product, wherein said cytokine-expressing cells are not tumor cells.

12. The composition of claim 11 wherein the cytokine gene product is selected from the group consisting of interleukin-1, interleukin-2, interleukin-3, interleukin-4, interleukin-5, interleukin-6, and gamma interferon.

13. The composition of claim 11 wherein the cytokine gene product is interleukin-2.

14. The composition of claim 11 wherein said cytokine gene product is expressed at a level sufficient to stimulate the immune response in said patient but low enough to avoid substantial systemic toxicities.

15. The method of claim 9 wherein said retroviral expression vector has a promotor causing sustained secretion of IL-2.

16. The method of claim 15 wherein said retroviral expression vector causes the secretion of about two nanograms to about 160 nanograms of IL-2 per $10^6$ cells per day.

17. The method of claim 10 wherein said suicide gene is the gene coding for herpes simplex virus thymidine kinase.

18. The method of claim 10 wherein the suicide function of said suicide gene is activated after stimulation of the patient's immune system.

19. A method of inhibiting or preventing the growth of carcinoma tumor cells in a patient comprising the stimulation of that patient's immune response against the carcinoma tumor cells by administering to said patient at a site other than an active tumor site a composition comprising carcinoma tumor antigens and cytokine-expressing cells genetically modified to express a cytokine gene product, wherein said cytokine-expressing cells are not tumor cells, and wherein said administering stimulates a systemic active immune response in said patient, and wherein said systemic active immune response results in inhibition of growth of said carcinoma tumor cells.

20. The method of claim 19, wherein said carcinoma tumor cell antigens are colorectal tumor cells.

21. The method of claim 20, wherein said cytokine gene product is IL-2.

22. A composition for increasing a patient's immune response to carcinoma tumor cells, comprising carcinoma tumor cell antigens and cytokine-expressing cells genetically modified to express a cytokine gene product, wherein said cytokine-expressing cells are not tumor cells.

23. The composition of claim 22, wherein said carcinoma tumor cell antigens are colorectal tumor cells.

24. The composition of claim 23, wherein said cytokine gene product is IL-2.

* * * * *